US012735495B2

(12) United States Patent
Chen et al.

(10) Patent No.: US 12,735,495 B2
(45) Date of Patent: Sep. 15, 2026

(54) ANTIBODIES BINDING IL4R AND USES THEREOF

(71) Applicant: CHIA TAI TIANQING PHARMACEUTICAL GROUP CO., LTD., Lianyungang (CN)

(72) Inventors: Mingjiu Chen, Nanjing (CN); Wei Tan, Nanjing (CN); Cathy Xiaoyan Zhong, Nanjing (CN); Mark Zhiqing Ma, Nanjing (CN); Shukai Xia, Nanjing (CN); Zhengping Zhang, Lianyungang (CN); Hongjiang Xu, Lianyungang (CN); Zhijian Lu, Lianyungang (CN)

(73) Assignee: CHIA TAI TIANQING PHARMACEUTICAL GROUP CO., LTD., Jiangsu (CN)

( * ) Notice: Subject to any disclaimer, the term of this patent is extended or adjusted under 35 U.S.C. 154(b) by 976 days.

(21) Appl. No.: 17/800,580

(22) PCT Filed: Feb. 25, 2021

(86) PCT No.: PCT/CN2021/077784

§ 371 (c)(1),
(2) Date: Aug. 18, 2022

(87) PCT Pub. No.: WO2021/170020

PCT Pub. Date: Sep. 2, 2021

(65) Prior Publication Data

US 2023/0105029 A1 Apr. 6, 2023

Related U.S. Application Data

(60) Provisional application No. 62/982,521, filed on Feb. 27, 2020.

(51) Int. Cl.

| | |
|---|---|
| ***C07K 16/28*** | (2006.01) |
| ***A61P 35/00*** | (2006.01) |
| ***A61P 37/00*** | (2006.01) |
| *A61K 39/00* | (2006.01) |

(52) U.S. Cl.

CPC .......... *C07K 16/2866* (2013.01); *A61P 35/00* (2018.01); *A61P 37/00* (2018.01); *A61K 2039/505* (2013.01); *C07K 2317/24* (2013.01); *C07K 2317/565* (2013.01); *C07K 2317/92* (2013.01)

(58) Field of Classification Search

CPC .............. A61K 31/7088; A61K 33/243; A61K 39/001102; A61K 39/001129; A61K 39/3955; A61K 31/713; A61K 2039/505; A61K 45/06; A61K 39/39; A61P 35/00; A61P 35/02; A61P 37/00; A61P 37/08; C12N 15/11; C07K 14/705; C07K 16/2818; C07K 16/2875; C07K 16/2827; C07K 16/2866; C07K 2317/24; C07K 2317/565; C07K 2317/92; C07K 2317/33; C07K 2317/76; C07K 2317/94; C07K 2317/73

See application file for complete search history.

(56) References Cited

U.S. PATENT DOCUMENTS

| | | | | |
|---|---|---|---|---|
| 7,638,606 | B2 | 12/2009 | Carter et al. | |
| 7,872,113 | B2 | 1/2011 | Carter et al. | |
| 8,980,273 | B1 * | 3/2015 | Clube | C12N 9/6424 424/143.1 |
| 8,986,691 | B1 | 3/2015 | Clube | |
| 2007/0071675 | A1 | 3/2007 | Wu et al. | |
| 2011/0008326 | A1 | 1/2011 | Hill et al. | |
| 2012/0135010 | A1 | 5/2012 | Stevens et al. | |
| 2017/0281769 | A1 | 10/2017 | Eriksson et al. | |
| 2024/0092920 | A1 | 3/2024 | Chen et al. | |

FOREIGN PATENT DOCUMENTS

| | | | |
|---|---|---|---|
| CN | 1886426 | A | 12/2006 |
| CN | 106604744 | A | 4/2017 |
| CN | 108409860 | | 8/2018 |
| CN | 110540590 | | 12/2019 |
| EA | 011302 | | 2/2009 |
| WO | WO 2001077342 | | 10/2001 |
| WO | WO 2009081201 | | 7/2009 |
| WO | WO 2010053751 | | 5/2010 |

(Continued)

OTHER PUBLICATIONS

African Journal of Biotechnology, 10(79):18294-18302, 2011 (Year: 2011).*

(Continued)

*Primary Examiner* — Nelson B Moseley, II
*Assistant Examiner* — Josephine K Darpolor
(74) *Attorney, Agent, or Firm* — Fish & Richardson P.C.

(57) ABSTRACT

An isolated monoclonal antibody that specifically binds human IL4Rα, or an antigen-binding portion thereof. A nucleic acid molecule encoding the antibody or the antigen-binding portion thereof, an expression vector, a host cell and a method for expressing the antibody or the antigen-binding portion thereof are also provided. The present disclosure further provides a bispecific molecule, an oncolytic virus and a pharmaceutical composition comprising the antibody or the antigen-binding portion thereof, as well as a treatment method using an Anti-IL4Rα antibody or the antigen-binding portion thereof of the disclosure.

22 Claims, 17 Drawing Sheets

Specification includes a Sequence Listing.

(56) References Cited

FOREIGN PATENT DOCUMENTS

WO WO 2010070346 6/2010

OTHER PUBLICATIONS

Annu. Rev. Biophys. Biophys. Chem., 16: 139-159, 1987 (Year: 1987).*
J. Immunol. Methods, 251(1-2): 137-149, 2001 (Year: 2001).*
Shen et al., "Single variable domain-IgG fusion: a novel recombinant approach to Fc domain-containing bispecific antibodies," The Journal of Biological Chemistry, Apr. 2006, 281(16):10706-10714.
Torres et al., "The immunoglobulin constant region contributes to affinity and specificity," Trends in Immunology, Feb. 2008, 29(2):91-97.
Bankaitis et al., "Targeting IL4/IL4R for the treatment of epithelial cancer metastasis," Clin. Exp. Metastasis, Dec. 2015, 32(8):847-56.
International Search Report and Written Opinion in International Appln. No. PCT/CN2021/077784, mailed on Jun. 11, 2021, 14 pages.

* cited by examiner

| | B1D2F7D3B5 | Dupilumab |
|---|---|---|
| EC50 | 0.0644 | 0.02845 |

| | B8G11F2B7G5E8 | B9D1D11F8D8 | Dupilumab |
|---|---|---|---|
| EC50 | 0.03934 | 0.07034 | 0.02281 |

| | Mouse C2C1A1A1 | Mouse C2B2F7B7 | Dupilumab |
|---|---|---|---|
| EC50 | 0.07586 | 0.1288 | 0.04789 |

| | Mouse B1D2F7D3B5 | Dupilumab |
|---|---|---|
| EC50 | 0.2464 | 0.134 |

| | Mouse B8G11F2B7G5E8 | Dupilumab |
|---|---|---|
| EC50 | 0.2509 | 0.1282 |

| | Mouse B9D1D11F8D8 | Dupilumab |
|---|---|---|
| EC50 | 0.2209 | 0.2544 |

| | Mouse C2C1A1A1 | Mouse C2B2F7B7 | Dupilumab |
|---|---|---|---|
| EC50 | 0.159 | 0.1831 | 0.08156 |

| | Mouse B8G11F2B7G5E8 | Mouse C2C1A1A1 | Mouse C2B2F7B7 | Dupilumab |
|---|---|---|---|---|
| EC50 | 0.291 | 0.329 | 108.2 | 0.9544 |

| | Mouse B1D2F7D3B5 | Mouse B8G11F2B7G5E8 | Mouse B9D1D11F8D8 | Dupilumab |
|---|---|---|---|---|
| IC50 | 1.796 | 0.81 | 2.881 | 0.6821 |

| | Mouse C2C1A1A1 | Mouse C2B2F7B7 | Dupilumab |
|---|---|---|---|
| IC50 | 0.8124 | 0.7263 | 0.2692 |

| | Mouse B1D2F7D3B5 | Mouse B8G11F2B7G5E8 | Mouse B9D1D11F8D8 | Dupilumab |
|---|---|---|---|---|
| IC50 | 0.02397 | 0.01715 | 0.02089 | 0.0235 |

| | Mouse C2C1A1A1 | Mouse C2B2F7B7 | Dupilumab |
|---|---|---|---|
| IC50 | 0.03826 | 0.7161 | 0.01579 |

| | Mouse B1D2F7D3B5 | Mouse B8G11F2B7G5E8 | Dupilumab |
|---|---|---|---|
| IC50 | 0.7873 | 0.8042 | 0.3017 |

| | Mouse B9D1D11F8D8 | Dupilumab |
|---|---|---|
| IC50 | 0.7478 | 0.313 |

| | Mouse C2C1A1A1 | Mouse C2B2F7B7 | Dupilumab |
|---|---|---|---|
| IC50 | 0.4398 | 0.3967 | 0.2203 |

| | Mouse B1D2F7D3B5 | Mouse B8G11F2B7G5E8 |
|---|---|---|
| IC50 | 0.1739 | 0.2332 |

| Mouse B9D1D11F8D8 | Mouse C2B2F7B7 | Mouse C2C1A1A1 | Dupilumab |
|---|---|---|---|
| 0.2331 | 0.1745 | ~ 0.1583 | 0.2795 |

| | Mouse B1D2F7D3B5 | Mouse B8G11F2B7G5E8 |
|---|---|---|
| IC50 | 0.4834 | 0.4693 |

| Mouse B9D1D11F8D8 | Mouse C2B2F7B7 | Mouse C2C1A1A1 | Dupilumab |
|---|---|---|---|
| 0.3634 | 0.3066 | 0.2266 | 0.5328 |

| | Mouse C2C1A1A1 | Chimeric C2C1A1A1 |
|---|---|---|
| EC50 | 0.02617 | 0.05485 |

| Mouse B8G11F2B7G5E8 | Chimeric B8G11F2B7G5E8 | Dupilumab |
|---|---|---|
| 0.1432 | 0.2749 | 0.04849 |

| | Mouse C2C1A1A1 | Chimeric C2C1A1A1 |
|---|---|---|
| EC50 | 0.3071 | 0.6305 |

| Mouse B8G11F2B7G5E8 | Chimeric B8G11F2B7G5E8 | Dupilumab |
|---|---|---|
| 0.4124 | 0.7753 | 0.4623 |

| | Mouse C2C1A1A1 | Chimeric C2C1A1A1 |
|---|---|---|
| IC50 | 1.891 | 3.12 |

| Mouse B8G11F2B7G5E8 | Chimeric B8G11F2B7G5E8 | Dupilumab |
|---|---|---|
| 1.638 | 1.823 | 2.061 |

| | Mouse B8G11F2B7G5E8 | Chimeric B8G11F2B7G5E8 |
|---|---|---|
| IC50 | 0.256 | 0.2594 |

| Mouse C2C1A1A1 | Chimeric C2C1A1A1 | Dupilumab |
|---|---|---|
| 0.193 | 0.2665 | 0.3701 |

| | Mouse B8G11F2B7G5E8 | Chimeric B8G11F2B7G5E8 |
|---|---|---|
| IC50 | 0.6008 | 0.7593 |

| Mouse C2C1A1A1 | Chimeric C2C1A1A1 | Dupilumab |
|---|---|---|
| 0.2742 | 0.5578 | 0.4849 |

| | Mouse B8G11F2B7G5E8 | Chimeric B8G11F2B7G5E8 | huB8G11F2B7G5E8-V2 |
|---|---|---|---|
| EC50 | 0.2128 | 0.3186 | 0.2738 |

| huB8G11F2B7G5E8-V4 | huB8G11F2B7G5E8-V14 | Dupilumab |
|---|---|---|
| 0.2746 | 0.237 | 0.05048 |

| | Chimeric C2C1A1A1 | huC2C1A1A1-V15 | huC2C1A1A1-V14 | Dupilumab |
|---|---|---|---|---|
| EC50 | 0.05415 | 0.04743 | 0.06158 | 0.05167 |

| | Mouse B8G11F2B7G5E8 | Chimeric B8G11F2B7G5E8 | huB8G11F2B7G5E8-V2 |
|---|---|---|---|
| EC50 | 0.4998 | 1.06 | 914.1 |

| huB8G11F2B7G5E8-V4 | huB8G11F2B7G5E8-V14 | Dupilumab |
|---|---|---|
| 7.122 | 137.4 | 3.335 |

| | Chimeric C2C1A1A1 | huC2C1A1A1-V15 | huC2C1A1A1-V14 | Dupilumab |
|---|---|---|---|---|
| EC50 | 0.6031 | 0.5173 | 0.6773 | 0.6742 |

| | Mouse B8G11F2B7G5E8 | Chimeric B8G11F2B7G5E8 | huAbB8G11F2B7G5E8-V2 |
|---|---|---|---|
| EC50 | 0.8728 | 1.012 | 0.7992 |

| huB8G11F2B7G5E8-V4 | huB8G11F2B7G5E8-V14 | Dupilumab |
|---|---|---|
| 0.7258 | 1.058 | 1.838 |

| | Mouse C2C1A1A1 | Chimeric C2C1A1A1 | huC2C1A1A1-V15 | huC2C1A1A1-V14 | Dupilumab |
|---|---|---|---|---|---|
| EC50 | 0.5744 | 0.6232 | 0.4122 | 0.5546 | 1.715 |

| | Mouse B8G11F2B7G5E8 | Chimeric B8G11F2B7G5E8 | huB8G11F2B7G5E8-V2 |
|---|---|---|---|
| EC50 | 0.3251 | 0.4421 | 0.426 |

| huB8G11F2B7G5E8-V4 | huB8G11F2B7G5E8-V14 | Dupilumab |
|---|---|---|
| 0.4145 | 0.5166 | 0.526 |

| | Chimeric C2C1A1A1 | huC2C1A1A1-V15 | huC2C1A1A1-V14 | Dupilumab |
|---|---|---|---|---|
| EC50 | 0.3259 | 0.3109 | 0.3901 | 0.397 |

| | Mouse B8G11F2B7G5E8 | Chimeric B8G11F2B7G5E8 | huB8G11F2B7G5E8-V2 |
|---|---|---|---|
| IC50 | 0.5003 | 0.3642 | 0.5385 |

| huB8G11F2B7G5E8-V4 | huB8G11F2B7G5E8-V14 | Dupilumab |
|---|---|---|
| 0.513 | 0.6012 | 0.5052 |

| | Chimeric C2C1A1A1 | huC2C1A1A1-V15 | huC2C1A1A1-V14 | Dupilumab |
|---|---|---|---|---|
| IC50 | 0.4824 | 0.5016 | 0.5782 | 0.4211 |

| | Mouse B8G11F2B7G5E8 | Chimeric B8G11F2B7G5E8 | huB8G11F2B7G5E8-V2 |
|---|---|---|---|
| IC50 | 0.9999 | 1.415 | 1.004 |

| huB8G11F2B7G5E8-V4 | huB8G11F2B7G5E8-V14 | Dupilumab |
|---|---|---|
| 0.8246 | 1.02 | 1.561 |

| | Chimeric C2C1A1A1 | huC2C1A1A1-V15 | huC2C1A1A1-V14 | Dupilumab |
|---|---|---|---|---|
| IC50 | 2.459 | 2.031 | 2.168 | 1.741 |

| | Chimeric B8G11F2B7G5E8 | huB8G11F2B7G5E8-V2 |
|---|---|---|
| IC50 | 1.517 | 1.204 |

| huB8G11F2B7G5E8-V4 | huB8G11F2B7G5E8-V14 | Dupilumab |
|---|---|---|
| 1.235 | 0.7631 | 0.1315 |

| | Chimeric C2C1A1A1 | huC2C1A1A1-V15 | huC2C1A1A1-V14 | Dupilumab |
|---|---|---|---|---|
| IC50 | 0.1719 | 0.1588 | 0.1711 | 0.1893 |

| | Chimeric C2C1A1A1 | huC2C1A1A1-V15 | huC2C1A1A1-V14 | Chimeric B8G11F2B7G5E8 |
|---|---|---|---|---|
| IC50 | 0.2626 | 0.6093 | 0.6411 | 0.4465 |

| huB8G11F2B7G5E8-V14 | huB8G11F2B7G5E8-V2 | huB8G11F2B7G5E8-V4 | Dupilumab |
|---|---|---|---|
| 0.257 | 0.4036 | 0.2984 | 0.7007 |

| | Chimeric C2C1A1A1 | huC2C1A1A1-V15 | huC2C1A1A1-V14 | Chimeric B8G11F2B7G5E8 |
|---|---|---|---|---|
| IC50 | 0.3913 | 0.6012 | 0.7344 | 0.5033 |

| huB8G11F2B7G5E8-V14 | huB8G11F2B7G5E8-V2 | huB8G11F2B7G5E8-V4 | Dupilumab |
|---|---|---|---|
| 0.6624 | 0.626 | 0.808 | 0.8422 |

ANTIBODIES BINDING IL4R AND USES THEREOF

RELATED APPLICATIONS AND INCORPORATION BY REFERENCE

This application is a U.S. National Phase application under 35 U.S.C. § 371 of International Patent Application No. PCT/CN2021/077784 filed Feb. 25, 2021, which claims priority to U.S. provisional application No. 62/982,521 filed Feb. 27, 2020.

The foregoing application, and all documents cited therein or during its prosecution ("appln cited documents") and all documents cited or referenced herein (including without limitation all literature documents, patents, published patent applications cited herein) ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference. Any Genbank sequences mentioned in this disclosure are incorporated by reference with the Genbank sequence to be that of the earliest effective filing date of this disclosure.

FIELD OF THE INVENTION

The present disclosure relates generally to an isolated monoclonal antibody, particularly a mouse, chimeric or humanized monoclonal antibody, or the antigen-binding portion thereof, that binds to human IL4R or more specifically human IL4Rα, with high affinity and functionality. A nucleic acid molecule encoding the antibody or the antigen-binding portion thereof, an expression vector, a host cell and a method for expressing the antibody or the antigen-binding portion thereof are also provided. The present disclosure further provides a bispecific molecule, an immunoconjugate, a chimeric antigen receptor, an oncolytic virus, and a pharmaceutical composition comprising the antibody or the antigen-binding portion thereof, as well as a treatment method using the anti-IL4Rα antibody or antigen-binding portion thereof of the disclosure.

BACKGROUND OF THE INVENTION

The type 2 inflammation related allergic disorders, such as atopic dermatitis, anaphylaxis, allergic rhinitis, and allergic asthma, afflict more then 3 billion people around the world, and the incidence continues to rise. According to the hygiene hypothesis, the high incidence is partly due to the reduced exposure to infections as the living standards advance, making the immune system deal more with certain otherwise harmless allergens (Stephen J. Galli et al., (2008) *Nature* 454 (7203): 445-454). Two factors central to type 2 immunity are interleukin-4 (IL-4) and IL-13. They are required to drive most of the key hallmarks associated with type 2 inflammation, such as immunoglobulin E production, and innate cell recruitment to inflammantion sites (Gruning G et al., (1998) *Science* 282:2261-2263; Rankin J A et al., (1996) *Proc Natl Acad Sci USA* 93:7821-7825; Wills-Karp M et al., (1998) *Science* 282:2258-2261).

IL-4 and IL-13 are adjacent to one another on chromosome 5 in humans, and share may regulatory elements. In T helper 2 (TH2) cells, both coordinate and non-coordinate expression of these two cytokines are observed (Katherine Bao et al., (2015) *Cytokine* 75 (1): 25-37). The two cytokines bind cell surface receptors to regulate cellular functions and activate transcriptional machinery. In specific, IL-4 first binds to IL-4Rα chain with picomolar affinity, and recruits IL-2Rγ γc chain to form type I receptor complex, or alternatively IL-13Rα1 to form type II receptor complex. The level or availability of IL-2Rγ γc and IL-13Rα1 determines which one to be recruited in receptor complex formation. It has been discovered that non-hematopoietic cells express no to low levels of IL-2Rγ γc and higher amounts of IL-13Rα1, while the opposite is found in lymphocytes. Myeloid cells fall in between these two categories of cells. The formation of type II IL-4 receptor complex may also be initiated with the binding of IL-13 to IL-13Rα1 chain with nanomollar affinity, resulting in further recruitment of the IL-4Rα chain. In addition to the type II IL-4 receptor, IL-13 also binds IL-13Rα2 with picomolar affinity, which functions as a decoy receptor (Irina G. Luzina et al., (2012) J Leukoc Biol 92 (4): 753-764). Once the IL-4 receptor complexes are assembled, intracellular signaling molecules are activated, wherein STAT6 and IRS signaling are responsive to the type I IL-4 receptor activation while type II IL-4 receptor is unable to activate IRS significantly (Heller N M et al., (2008) *Sci Signal* 1 (51): ra17-ra17). The STAT6 signaling is important in TH2 cell differentiation and IL-4 production, and IRS molecules activate signaling pathways including PI3K and mTOR (Gadani S P et al., (2012) *J Immunol* 189:4213-4219).

Researches have suggested that excess IL-4/IL-13 signaling might cause allergic diseases, and therefore several therapeutic antibodies have been developed to modify IL-4 and IL-13 mediated signalings. For example, Leprikizumab, Anrukinzumab and Tralokinumab bind IL-13, and Pascolizumab targets IL-4. Dupilumab and Pitrakinra are IL-4Rα antagonists, wherein Pitrakinra upon binding to IL-4Rα blocks both type I and type II IL-4 receptors (Antoniu S A (2010) *Curr Opin Investig Drugs* 11:1286-1294). Moreover, a STAT6 inhibitor has been found to inhibit prostate cancer cell growth, suggesting that targeting IL-4/IL-13 may benefit cancer treatment (Nappo G et al., (2017) *Oncogenesis* 2017, 6 (5): e342). Therefore, more antibodies targeting IL-4, IL-13 and their receptors, especially IL-4Rα, with more desired therapeutic properties are desired.

SUMMARY OF THE INVENTION

The present disclosure provides an isolated monoclonal antibody, for example, a mouse, human, chimeric or humanized monoclonal antibody, or an antigen-binding portion thereof, that binds to IL4Rα (e.g., the human IL4Rα) and has comparable or higher binding affinity/capacity to human and/or monkey IL4Rα, and comparable or higher blocking activity on IL4Rα-IL4/IL13-IL13Rα1 interaction and the corresponding intracellular signal transduction, as compared to prior art anti-IL4Rα antibodies such as Dupilumab.

The antibody or antigen-binding portion of the disclosure can be used for a variety of applications, including detection of the IL4Rα protein, and treatment and prevention of IL4, IL13 or IL4R associated diseases, such as allergic diseases and cancers.

Accordingly, in one aspect, the disclosure pertains to an isolated monoclonal antibody (e.g., a mouse, chimeric or humanized antibody), or an antigen-binding portion thereof, that binds IL4Rα, having a heavy chain variable region that comprises a CDR1 region, a CDR2 region and a CDR3 region, wherein the CDR1 region, the CDR2 region and the CDR3 region comprise amino acid sequences having at least 85%, 86%, 87%, 88%, 89%, 90%, 91%, 92%, 93%, 94%, 95%, 96%, 97%, 98%, 99% or 100% identity to (1) SEQ ID NOs: 1, 5 and 10, respectively; (2) SEQ ID NOs: 1, 6 and 11, respectively; (3) SEQ ID NOs: 2, 7 and 12, respectively; (4) SEQ ID NOs: 3, 8 and 13, respectively; (5) SEQ ID NOs: 4, 8 and 13, respectively; or (6) SEQ ID NOs: 3, 9 and 14, respectively.

In one aspect, an isolated monoclonal antibody, or an antigen-binding portion thereof, of the present disclosure comprises a heavy chain variable region comprising an amino acid sequence having at least 85%, 86%, 87%, 88%, 89%, 90%, 91%, 92%, 93%, 94%, 95%, 96%, 97%, 98%, 99% or 100% identity to SEQ ID NOs: 32, 33 (X1=W, X2=S; X1=L, X2=A; X1=W, X2=A), 34, 38, 40, 41 (X1=A, X2=K, X3=V, X4=H; X1=V, X2=K, X3=V, X4=H; X1=A, X2=Q, X3=V, X4=H; X1=A, X2=K, X3=M, X4=H; X1=A, X2=K, X3=V, X4=Y; X1=V, X2=K, X3=M, X4=H), 42 (X1=R, X2=A, X3=S, X4=N; X1=K, X2=V, X3=S, X4=N; X1=K, X2=A, X3=T, X4=N; X1=K, X2=A, X3=S, X4=D; X1=R, X2=V, X3=T, X4=N), 43, 44, 47, 49, 51 or 53, wherein the antibody or antigen-binding portion thereof binds to IL4Rα. The amino acid sequence of SEQ ID NO: 32 may be encoded by the nucleotide sequences of SEQ ID NOs: 59 or 60. The amino acid sequence of SEQ ID NO: 40 may be encoded by the nucleotide sequences of SEQ ID NOs: 65 or 66. The amino acid sequences of SEQ ID NOs: 33 (X1=W, X2=A) and 41 (X1=V, X2=K, X3=M, X4=H) may be encoded by the nucleotide sequences of SEQ ID NOs: 61 and 67, respectively.

In one aspect, an isolated monoclonal antibody, or an antigen-binding portion thereof, of the present disclosure, that binds IL4Rα, comprises a light chain variable region that comprises a CDR1 region, a CDR2 region and a CDR3 region, wherein the CDR1 region, the CDR2 region, and the CDR3 region comprise amino acid sequences having at least 85%, 86%, 87%, 88%, 89%, 90%, 91%, 92%, 93%, 94%, 95%, 96%, 97%, 98%, 99% or 100% identity to (1) SEQ ID NOs: 15, 22 and 26, respectively; (2) SEQ ID NOs: 16, 22 and 27, respectively; (3) SEQ ID NOs: 17, 23 and 28, respectively; (4) SEQ ID NOs: 18, 24 and 29, respectively; (5) SEQ ID NOs: 19, 24 and 30, respectively; (6) SEQ ID NOs: 20, 25 and 31, respectively; or (7) SEQ ID NOs: 21, 25 and 31, respectively.

In one aspect, an isolated monoclonal antibody, or an antigen-binding portion thereof, of the present disclosure comprises a light chain variable region comprising an amino acid sequence having at least 85%, 86%, 87%, 88%, 89%, 90%, 91%, 92%, 93%, 94%, 95%, 96%, 97%, 98%, 99% or 100% identity to SEQ ID NOs: 35, 36 (X1=L, X2=I; X1=F, X2=V; X1=F, X2=I), 37, 39, 45, 46, 48, 50, 52 or 54, wherein the antibody or antigen-binding portion thereof binds to IL4Rα. The amino acid sequence of SEQ ID NO: 35 may be encoded by the nucleotide sequences of SEQ ID NOs: 62 or 63. The amino acid sequence of SEQ ID NO: 45 may be encoded by the nucleotide sequences of SEQ ID NOs: 68 or 69. The amino acid sequences of SEQ ID NO: 36 (X1=F, X2=V) and 46 may be encoded by the nucleotide sequences of SEQ ID NO: 64 and 70, respectively.

In one aspect, an isolated monoclonal antibody, or an antigen-binding portion thereof, of the present disclosure comprises a heavy chain variable region and a light chain variable region each comprising a CDR1 region, a CDR2 region and a CDR3 region, wherein the heavy chain variable region CDR1, CDR2 and CDR3, and the light chain variable region CDR1, CDR2 and CDR3 comprise amino acid sequences having at least 85%, 86%, 87%, 88%, 89%, 90%, 91%, 92%, 93%, 94%, 95%, 96%, 97%, 98%, 99% or 100% identity to (1) SEQ ID NOs: 1, 5, 10, 15, 22 and 26, respectively; (2) SEQ ID NOs: 1, 6, 11, 16, 22 and 27, respectively; (3) SEQ ID NOs: 2, 7, 12, 17, 23 and 28, respectively; (4) SEQ ID NOs: 3, 8, 13, 18, 24 and 29, respectively; (5) SEQ ID NOs: 4, 8, 13, 19, 24 and 30, respectively; (6) SEQ ID NOs: 3, 9, 14, 20, 25 and 31, respectively; or (7) SEQ ID NOs: 3, 9, 14, 21, 25 and 31, respectively, wherein the antibody or antigen-binding portion thereof binds to IL4Rα.

In one embodiment, an isolated monoclonal antibody, or the antigen-binding portion thereof, of the present disclosure comprises a heavy chain variable region and a light chain variable region, the heavy chain variable region and the light chain variable region comprising amino acid sequences having at least 85%, 86%, 87%, 88%, 89%, 90%, 91%, 92%, 93%, 94%, 95%, 96%, 97%, 98%, 99% or 100% identity to (1) SEQ ID NOs: 32 and 35, respectively; (2) SEQ ID NOs: 33 (X1=W, X2=S) and 36 (X1=L, X2=I; X1=F, X2=V; X1=F, X2=I), respectively; (3) SEQ ID NOs: 33 (X1=W, X2=S) and 37, respectively; (4) SEQ ID NOs: 34 and 36 (X1=L, X2=I; X1=F, X2=V; X1=F, X2=I), respectively; (5) SEQ ID NOs: 34 and 37, respectively; (6) SEQ ID NOs: 33 (X1=L, X2=A) and 36 (X1=L, X2=I; X1=F, X2=V; X1=F, X2=I), respectively; (7) SEQ ID NOs: 33 (X1=L, X2=A) and 37, respectively; (8) SEQ ID NOs: 33 (X1=W, X2=A) and 36 (X1=L, X2=I; X1=F, X2=V; X1=F, X2=I), respectively; (9) SEQ ID NOs: 33 (X1-W, X2-A) and 37, respectively; (10) SEQ ID NOs: 38 and 39, respectively; (11) SEQ ID NOs: 40 and 45, respectively; (12) SEQ ID NOs: 41 (X1-A, X2=K, X3=V, X4=H; X1=V, X2=K, X3=V, X4=H; X1=A, X2=Q, X3=V, X4=H; X1=A, X2=K, X3=M, X4=H; X1=A, X2=K, X3=V, X4=Y; X1=V, X2=K, X3=M, X4=H) and 46, respectively; (13) SEQ ID NOs: 42 (X1=R, X2=A, X3=S, X4=N; X1=K, X2=V, X3=S, X4=N; X1=K, X2=A, X3=T, X4=N; X1=K, X2=A, X3=S, X4=D; X1=R, X2=V, X3=T, X4=N) and 46, respectively; (14) SEQ ID NOs: 43 and 46, respectively; (15) SEQ ID NOs: 44 and 46, respectively; (16) SEQ ID NOs: 47 and 48, respectively; (17) SEQ ID NOs: 49 and 50, respectively; (18) SEQ ID NOs: 51 and 52, respectively; or (19) SEQ ID NOs: 53 and 54, respectively, wherein the antibody or antigen-binding portion thereof binds to IL4Rα.

In one embodiment, an isolated monoclonal antibody, or the antigen-binding portion thereof, of the present disclosure comprises a heavy chain and a light chain linked by disulfite bonds, the heavy chain comprising a heavy chain variable region and a heavy chain constant region, the light chain comprising a light chain variable region and a light chain constant region, wherein the C terminus of the heavy chain variable region is linked to the N terminus of the heavy chain constant region, and the C terminus of the light chain variable region is linked to the N terminus of the light chain constant region, wherein the heavy chain variable region and the light chain variable region comprise amino acid sequences described above, and the antibody or antigen-binding portion thereof binds to IL4Rα. The heavy chain constant region may be human IgG4 constant region having an amino acid sequence set forth in e.g., SEQ ID NO.: 55, and the light chain constant region may be human kappa constant region having an amino acid sequences set forth in e.g., SEQ ID NO.: 56. The amino acid sequences set forth in SEQ ID NOs: 55 and 56 may be encoded by the nucleotide sequences of SEQ ID NOs: 71 and 72, respectively.

The antibody of the present disclosure in some embodiments comprises or consists of two heavy chains and two light chains, wherein each heavy chain comprises the heavy chain constant region, heavy chain variable region or CDR sequences mentioned above, and each light chain comprises the light chain constant region, light chain variable region or CDR sequences mentioned above, wherein the antibody binds to IL4Rα. The antibody of the disclosure can be a full-length antibody, for example, of an IgG1, IgG2 or IgG4 isotype, preferably an IgG4 isotype with weak ADCC activity. The light chain constant region may be a kappa constant region. The antibody of the present disclosure in other embodiments may be a single chain variable fragment (scFv) antibody, or antibody fragments, such as Fab or $F(ab')_2$ fragments.

The antibody, or antigen-binding portion thereof, of the present disclosure has comparable, if not higher, binding affinity/capacity to human IL4Rα and/or monkey IL4Rα, and comparable, if not higher blocking activity on IL4Rα-IL4/IL13-IL13α1 interaction and the corresponding intracellular signal transduction, as compared to the prior art anti-IL4Rα antibodies such as Dupilumab.

The disclosure also provides a bispecific molecule comprising an antibody, or antigen-binding portion thereof, of the disclosure, linked to a second functional moiety (e.g., a second antibody) having a different binding specificity than said antibody, or antigen-binding portion thereof. The disclosure also provides an immunoconjugate, such as an antibody-drug conjugate, comprising an antibody of the disclosure, or antigen-binding portion thereof, linked to a therapeutic agent, such as a cytotoxin. In another aspect, the antibody or an antigen binding portions thereof of the present disclosure can be made into part of a chimeric antigen receptor (CAR). Also provided is an immune cell comprising the antigen chimeric receptor, such as a T cell. The antibody or an antigen binding portions thereof of the present disclosure can also be encoded by or used in conjunction with an oncolytic virus.

Compositions comprising the antibody, or antigen-binding portion thereof, or immunoconjugate, bispecific molecule, oncolytic virus, CAR or CAR-T cell of the disclosure, and a pharmaceutically acceptable carrier, are also provided. In some embodiments, the pharmaceutical composition may further contain an anti-allergic agent or an anti-tumor agent.

Nucleic acid molecules encoding the antibodies, or antigen-binding portions thereof, of the disclosure are also encompassed by the disclosure, as well as expression vectors comprising such nucleic acids and host cells comprising such expression vectors. A method for preparing an anti-IL4Rα antibody or an antigen-binding portion thereof using the host cell comprising the expression vector is also provided, comprising steps of (i) expressing the antibody in the host cell and (ii) isolating the antibody from the host cell or its cell culture.

In another aspect, the disclosure provides a method of reducing IL4/IL13 signaling. IL4 signals through a receptor comprising IL-4Rα and γC, whereas IL13 signaling involves a receptor comprising IL-4Rα and IL13 Rα1. Non-limiting examples of IL4/IL13 signaling include activation and/or proliferations of B cells, eosinophils, macrophages (e.g., alternatively activated macrophages), fibroblast proliferation and smooth muscle proliferation such as airway smooth muscle cell proliferation.

In yet another aspect, the disclosure provides a method for treating a disease associated with excessive IL4/IL13 signaling, comprising administering to a subject a therapeutically effective amount of the antibody, or antigen-binding portion thereof, of the present disclosure.

The disease may be an allergic disease. The allergic disease may be atopic dermatitis, anaphylaxis, allergic rhinitis, or allergic asthma. In some embodiments, the method for treating the allergic disease may comprises administering a composition, a bispecific molecule, or an antibody-encoding or antibody-bearing oncolytic virus of the disclosure, or alternatively a nucleic acid molecule or a vector capable of expressing the same in the subject. The method may also comprises administering an anti-allergic agent. The anti-allergic agent may be an antihistamine agent, corticosteroid, an agonist of beta-adrenergic receptors, an agent targeting cyc-LTs, or an agent targeting IgE.

The disease may be a tumor disease. The tumor may be a solid tumor or a non-solid tumor. In some embodiments, the tumor is prostate cancer. In some embodiments, the method comprises administering a composition, a bispecific molecule, an immunoconjugate such as an antibody-drug conjugate, a CAR-T cell, or an antibody-encoding or antibody-bearing oncolytic virus of the disclosure, or alternatively a nucleic acid molecule or a vector capable of expressing the same in the subject. In some embodiments, at least one additional anti-cancer antibody can be administered with the antibody, or an antigen-binding portion thereof, of the disclosure, such as an anti-VISTA antibody, an anti-PD-1 antibody, an anti-PD-L1 antibody, an anti-LAG-3 antibody, an anti-CTLA-4 antibody, an anti-TIM 3 antibody, an anti-STAT3 antibody, and/or an anti-ROR1 antibody. In yet another embodiment, an antibody, or an antigen-binding portion thereof, of the disclosure is administered with a cytokine (e.g., IL-2, IL-21, and/or GM-CSF), or a costimulatory antibody (e.g., an anti-CD137 and/or anti-GITR antibody). The antibodies of the present disclosure can be, for example, mouse, human, chimeric or humanized antibodies.

In yet another aspect, the disclosure provides a method for reducing type 2 immunity, comprising administering to a subject a therapeutically effective amount of the antibody, or antigen-binding portion thereof, of the present disclosure. In some embodiments, the method comprises administering a composition, a bispecific molecule, or an antibody-encoding or antibody-bearing oncolytic virus of the disclosure, or alternatively a nucleic acid molecule or a vector capable of expressing the same in the subject.

In yet another aspect, the disclosure provides diagnostic methods, compositions and kits. In an embodiment, an antibody of the disclosure is used to determine the presence and expression of IL4Rα in a cell or tissue and to determine prognosis and appropriate treatment and followup.

Other features and advantages of the instant disclosure will be apparent from the following detailed description and examples, which should not be construed as limiting. The contents of all references, Genbank entries, patents and published patent applications cited throughout this application are expressly incorporated herein by reference.

Figure 1A:
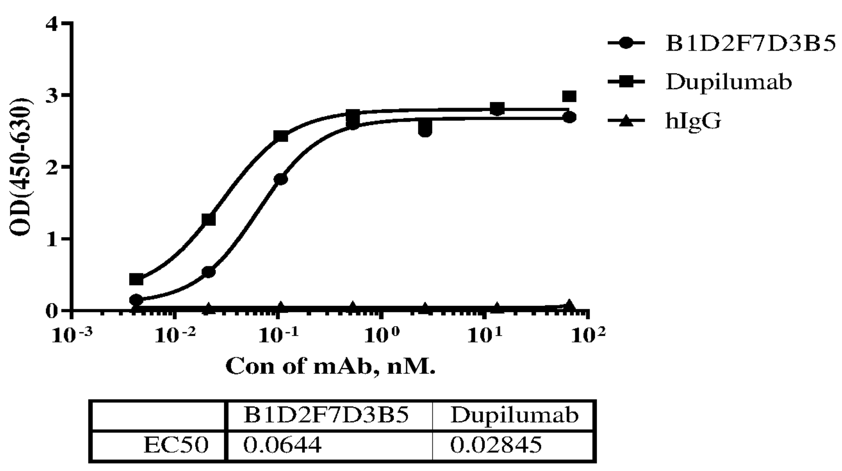
FIGS. 1A-1C show the binding capacity of mouse antibodies B1D2F7D3B5 (A), B8G11F2B7G5E8 and B9D1D11F8D8 (B), C2C1A1A1 and C2B2F7B7 (C) to human IL4Rα.
Figure 1B:
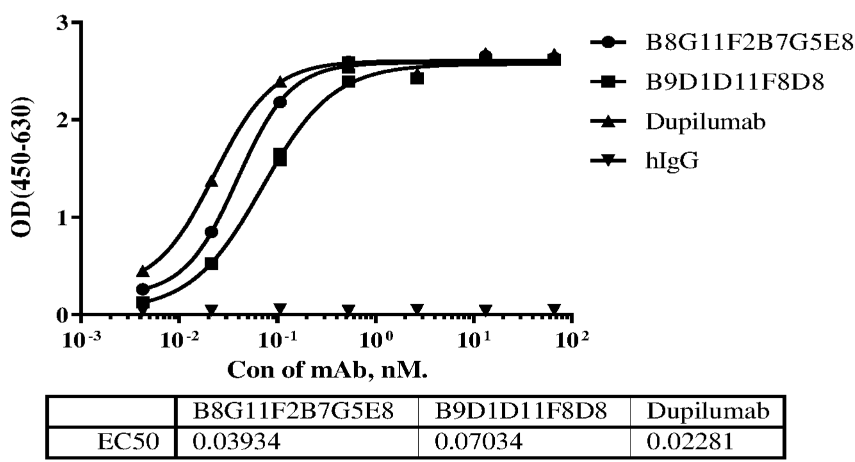
Figure 1C:
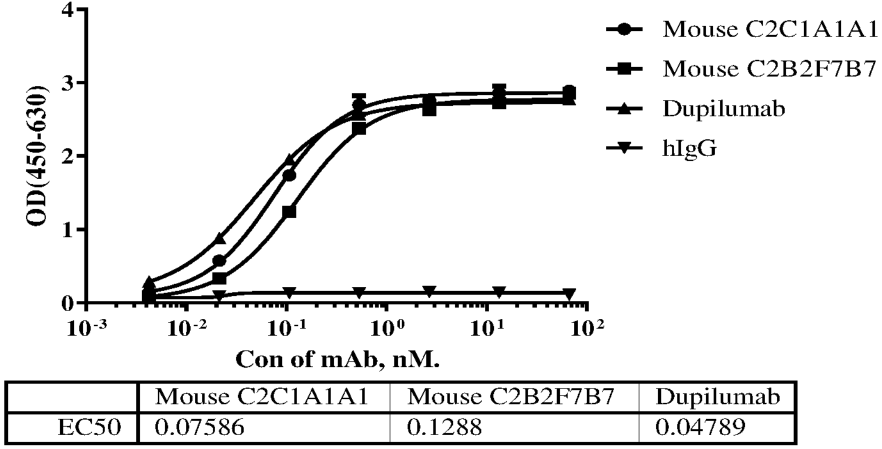
Figure 2A:
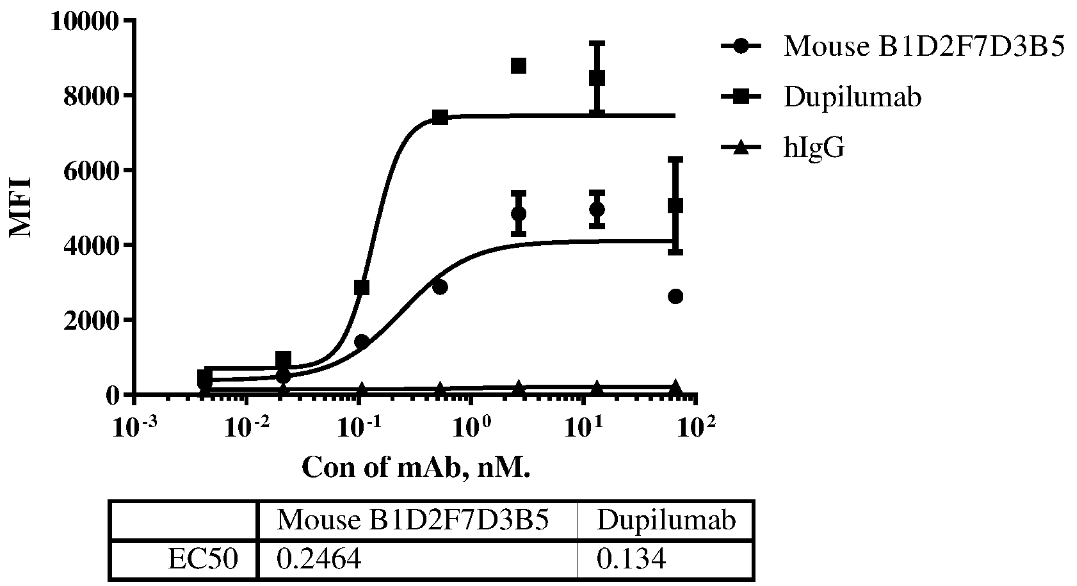
FIGS. 2A-2D show the binding capacity of mouse antibodies B1D2F7D3B5 (A), B8G11F2B7G5E8 (B), B9D1D11F8D8 (C), C2C1A1A1 and C2B2F7B7 (D) to cell surface human IL4Rα.
Figure 2B:
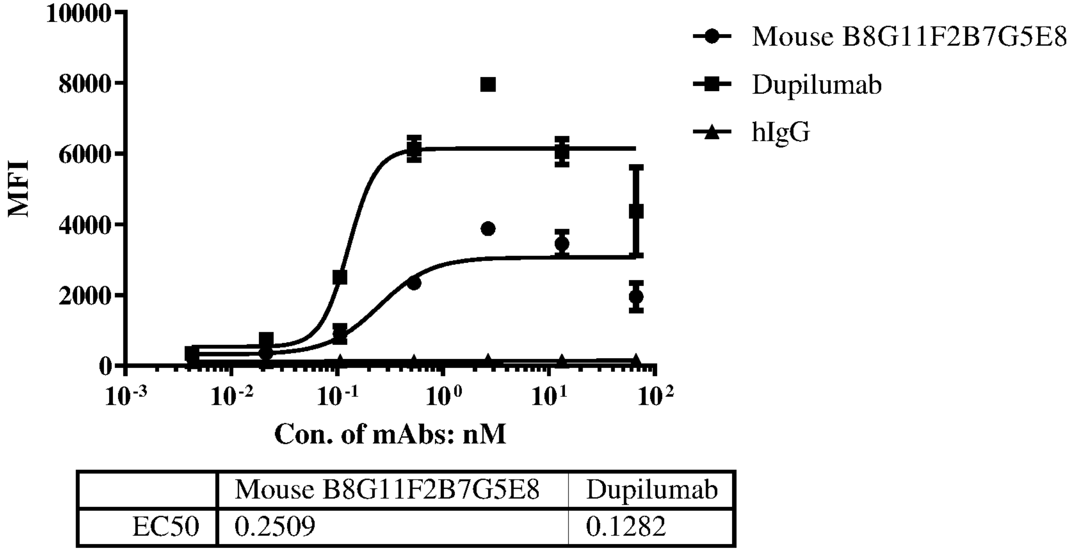
Figure 2C:
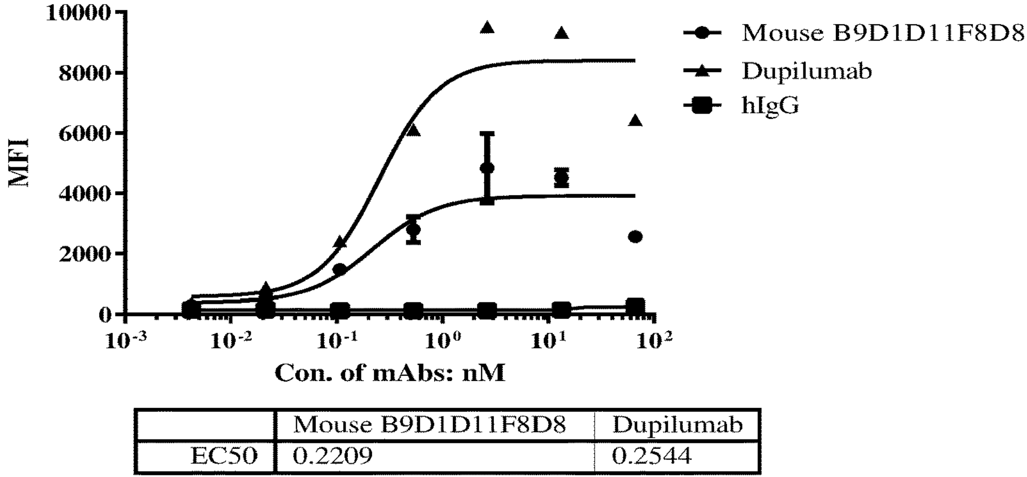
Figure 2D:
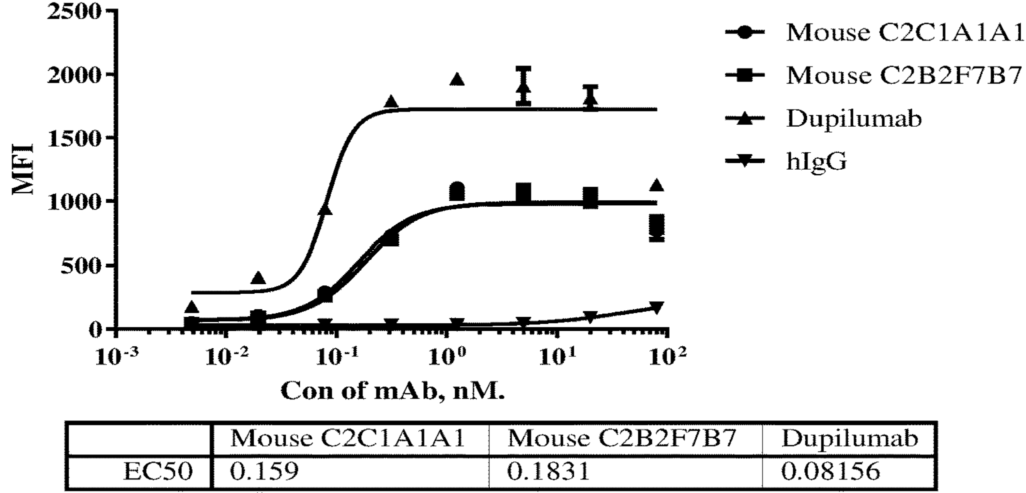
Figure 3:
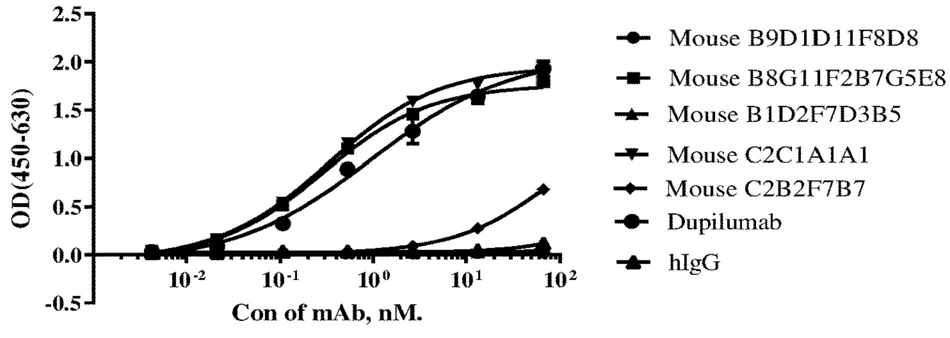
FIG. 3 shows the binding capacity of mouse antibodies B1D2F7D3B5, B8G11F2B7G5E8, B9D1D11F8D8, C2C1A1A1 and C2B2F7B7 to cynomolgus IL4Rα.

The following detailed description, given by way of example, but not intended to limit the disclosure solely to the specific embodiments described, may best be understood in conjunction with the accompanying drawings.

DETAILED DESCRIPTION OF THE INVENTION

To ensure that the present disclosure may be more readily understood, certain terms are first defined. Additional definitions are set forth throughout the detailed description.

The term "IL4Rα" refers to interleukin 4 receptor subunit alpha. The term "IL4Rα" comprises variants, isoforms, homologs, orthologs and paralogs. For example, an antibody specific for a human IL4Rα protein may, in certain cases, cross-react with an IL4Rα protein from a species other than human, such as monkey. In other embodiments, an antibody specific for a human IL4Rα protein may be completely specific for the human IL4Rα protein and exhibit no cross-reactivity to other species or of other types, or may cross-react with IL4Rα from certain other species but not all other species.

The term "human IL4Rα" refers to an IL4Rα protein having an amino acid sequence from a human, such as the amino acid sequence of human IL4Rα having a Genbank accession number of NP_001244335.1. The terms "cynomolgus monkey IL4Rα" and "marmoset monkey IL4Rα" refer to the IL4Rα sequences having e.g. amino acid sequences having Genbank Accession Nos. EHH60265.1 and NP_001244161.1, respectively.

The term "antibody" as referred to herein includes whole antibodies and any antigen binding fragment (i.e., "antigen-binding portion") or single chains thereof. Whole antibodies are glycoproteins comprising two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, refers to one or more fragments of an antibody that retain the ability to specifically bind to an antigen (e.g., an IL4Rα protein). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a $F(ab')_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; (vi) an isolated complementarity determining region (CDR); and (viii) a nanobody, a heavy chain variable region containing a single variable domain and two constant domains. Furthermore, although the two domains of the Fv fragment, $V_L$ and $V_H$, are coded by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., (1988) *Science* 242:423-426; and Huston et al., (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds an IL4Rα protein is substantially free of antibodies that specifically bind antigens other than IL4Rα proteins). An isolated antibody that specifically binds a human IL4Rα protein may, however, have cross-reactivity to other antigens, such as IL4Rα proteins from other species. Moreover, an isolated antibody can be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "mouse antibody", as used herein, is intended to include antibodies having variable regions in which both the framework and CDR regions are derived from mouse germline immunoglobulin sequences. Furthermore, if the antibody contains a constant region, the constant region also is derived from mouse germline immunoglobulin sequences. The mouse antibodies of the disclosure can include amino acid residues not encoded by mouse germline immunoglobulin sequences (e.g., mutations introduced by random or site-specific mutagenesis in vitro or by somatic mutation in vivo). However, the term "mouse antibody", as used herein, is not intended to include antibodies in which CDR sequences derived from the germline of another mammalian species have been grafted onto mouse framework sequences.

The term "chimeric antibody" refers to an antibody made by combining genetic material from a nonhuman source with genetic material from a human being. Or more generally, a chimetic antibody is an antibody having genetic material from a certain species with genetic material from another species.

The term "humanized antibody", as used herein, refers to an antibody from non-human species whose protein sequences have been modified to increase similarity to antibody variants produced naturally in humans.

The term "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

As used herein, an antibody that "specifically binds to human IL4Rα" is intended to refer to an antibody that binds to human IL4Rα protein (and possibly an IL4Rα protein from one or more non-human species) but does not substantially bind to non-IL4Rα proteins. Preferably, the antibody binds to human IL4Rα protein with "high affinity", namely with a $K_D$ of $5.0\times10^{-8}$ M or less, more preferably $1.0\times10^{-8}$ M or less, and more preferably $7.0\times10^{-9}$ M or less.

The term "does not substantially bind" to a protein or cells, as used herein, means does not bind or does not bind with a high affinity to the protein or cells, i.e. binds to the protein or cells with a $K_D$ of $1.0\times10^{-6}$ M or more, more preferably $1.0\times10^{-5}$ M or more, more preferably $1.0\times10^{-4}$ M or more, more preferably $1.0\times10^{-3}$ M or more, even more preferably $1.0\times10^{-2}$ M or more.

The term "high affinity" for an IgG antibody refers to an antibody having a $K_D$ of $1.0\times10^{-6}$ M or less, more preferably $5.0\times10^{-8}$ M or less, even more preferably $1.0\times10^{-8}$ M or less, even more preferably $7.0\times10^{-9}$ M or less and even more preferably $1.0\times10^{-9}$ M or less for a target antigen. However, "high affinity" binding can vary for other antibody isotypes. For example, "high affinity" binding for an IgM isotype refers to an antibody having a $K_D$ of $10^{-6}$ M or less, more preferably $10^{-7}$ M or less, even more preferably $10^{-8}$ M or less.

The term "$K_{assoc}$" or "$K_a$", as used herein, is intended to refer to the association rate of a particular antibody-antigen interaction, whereas the term "$K_{dis}$" or "$K_d$", as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore™ system.

The term "$EC_{50}$", also known as half maximal effective concentration, refers to the concentration of an antibody which induces a response halfway between the baseline and maximum after a specified exposure time.

The term "$IC_{50}$", also known as half maximal inhibitory concentration, refers to the concentration of an antibody which inhibits a specific biological or biochemical function by 50% relative to the absence of the antibody.

The term "subject" includes any human or nonhuman animal. The term "nonhuman animal" includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses.

The term "therapeutically effective amount" means an amount of the antibody of the present disclosure sufficient to prevent or ameliorate the symptoms associated with a disease or condition (such as a cancer) and/or lessen the severity of the disease or condition. A therapeutically effective amount is understood to be in context to the condition being treated, where the actual effective amount is readily discerned by those of skill in the art.

The term "identity" as used in the present disclosure refers to sequence similarity between two polynucleotide sequences or between two polypeptides. Sequence comparisons and percent identity determination between the two sequences can be performed by default settings of the BLASTN/BLASTP algorithm available on the National Center For Biotechnology Institute website.

Various aspects of the disclosure are described in further detail in the following subsections.

Anti-IL4Rα Antibodies Having Increased Binding Affinity to human IL4Rα and Better IL4/IL13 Signaling Blocking Activity The antibody, or the antigen-binding portion thereof, of the disclosure specifically binds to human IL4Rα with comparable, if not better, binding affinity/capacity as compared to previously described anti-IL4Rα antibodies, such as Dupilumab.

The antibody, or the antigen-binding portion thereof, of the disclosure blocks IL4Rα binding to IL4 or IL13-IL13Rα1, and therefore blocks the corresponding intracellular signal transduction, with comparable or higher activity, as compared to previously described anti-IL4Rα antibodies, such as Dupilumab.

Preferred antibodies of the disclosure are humanized monoclonal antibodies. Additionally or alternatively, the antibodies can be, for example, chimeric monoclonal antibodies.

Monoclonal Anti-IL4Rα Antibodies

The antibody of the disclosure is the monoclonal antibody structurally and chemically characterized as described below and in the following Examples. The amino acid sequence ID numbers of the heavy/light chain variable regions of the antibodies are summarized in Table 1 below, some antibodies sharing the same $V_H$ or $V_L$. The heavy chain constant region for the antibodies may be human IgG4 heavy chain constant region having an amino acid sequence set forth in, e.g., SEQ ID NO: 55, and the light chain constant region for the antibodies may be human kappa constant region having an amino acid sequence set forth in, e.g., SEQ ID NO: 56.

TABLE 1

Amino acid sequence ID numbers of heavy/light chain variable regions

| Antibody ID | VH-CDR1 | VH-CDR2 | VH-CDR3 | VH | VL-CDR1 | VL-CDR2 | VL-CDR3 | VL |
|---|---|---|---|---|---|---|---|---|
| C2C1A1A1 | 1 | 5 | 10 | 32 | 15 | 22 | 26 | 35 |
| huC2C1A1A1-V1 | | | | 33, X1 = W, X2 = S | | | | 36, X1 = L, X2 = I |
| huC2C1A1A1-V2 | | | | 33, X1 = W, X2 = S | | | | 37 |
| huC2C1A1A1-V3 | | | | 33, X1 = W, X2 = S | | | | 36, X1 = F, X2 = V |
| huC2C1A1A1-V4 | | | | 33, X1 = W, X2 = S | | | | 36, X1 = F, X2 = I |
| huC2C1A1A1-V5 | | | | 34 | | | | 36, X1 = L, X2 = I |
| huC2C1A1A1-V6 | | | | 34 | | | | 37 |
| huC2C1A1A1-V7 | | | | 34 | | | | 36, X1 = F, X2 = V |
| huC2C1A1A1-V8 | | | | 34 | | | | 36, X1 = F, X2 = I |
| huC2C1A1A1-V9 | | | | 33, X1 = L, X2 = A | | | | 36, X1 = L, X2 = I |
| huC2C1A1A1-V10 | | | | 33, X1 = L, X2 = A | | | | 37 |
| huC2C1A1A1-V11 | | | | 33, X1 = L, X2 = A | | | | 36, X1 = F, X2 = V |
| huC2C1A1A1-V12 | | | | 33, X1 = L, X2 = A | | | | 36, X1 = F, X2 = I |
| huC2C1A1A1-V13 | | | | 33, X1 = W, X2 = A | | | | 36, X1 = L, X2 = I |
| huC2C1A1A1-V14 | | | | 33, X1 = W, X2 = A | | | | 37 |
| huC2C1A1A1-V15 | | | | 33, X1 = W, X2 = A | | | | 36, X1 = F, X2 = V |
| huC2C1A1A1-V16 | | | | 33, X1 = W, X2 = A | | | | 36, X1 = F, X2 = I |
| C2B2F7B7 | 1 | 6 | 11 | 38 | 16 | 22 | 27 | 39 |
| B8G11F2B7G5E8 | 2 | 7 | 12 | 40 | 17 | 23 | 28 | 45 |
| huBSG11F2B7G5E8-V1 | | | | 41, X1 = A, X2 = K, X3 = V, X4 = H | | | | 46 |
| huBSG11F2B7G5E8-V2 | | | | 41, X1 = V, X2 = K, X3 = V, X4 = H | | | | 46 |
| huBSG11F2B7G5E8-V3 | | | | 41, X1 = A, X2 = Q, X3 = V, X4 = H | | | | 46 |
| huBSG11F2B7G5E8-V4 | | | | 41, X1 = A, X2 = K, X3 = M, X4 = H | | | | 46 |
| huBSG11F2B7G5E8-V5 | | | | 42, X1 = R, X2 = A, X3 = S, X4 = N | | | | 46 |
| huBSG11F2B7G5E8-V6 | | | | 42, X1 = K, X2 = V, X3 = S, X4 = N | | | | 46 |
| huBSG11F2B7G5E8-V7 | | | | 42, X1 = K, X2 = A, X3 = T, X4 = N | | | | 46 |
| huBSG11F2B7G5E8-V8 | 2 | 7 | 12 | 42, X1 = K, X2 = A, X3 = S, X4 = D | 17 | 23 | 28 | 46 |
| huBSG11F2B7G5E8-V9 | | | | 41, X1 = A, X2 = K, X3 = V, X4 = Y | | | | 46 |
| huBSG11F2B7G5E8-V10 | | | | 42, X1 = R, X2 = V, X3 = T, X4 = N | | | | 46 |

TABLE 1-continued

| Amino acid sequence ID numbers of heavy/light chain variable regions | | | | | | | | |
|---|---|---|---|---|---|---|---|---|
| Antibody ID | VH-CDR1 | VH-CDR2 | VH-CDR3 | VH | VL-CDR1 | VL-CDR2 | VL-CDR3 | VL |
| huBSG11F2B7G5E8-V11 | | | | 43 | | | | 46 |
| huBSG11F2B7G5E8-V13 | | | | 44 | | | | 46 |
| huBSG11F2B7G5E8-V14 | | | | 41, X1 = V, X2 = K, X3 = M, X4 = H | | | | 46 |
| B8D10G7G6E4 | 3 | 8 | 13 | 47 | 18 | 24 | 29 | 48 |
| B9A7C9A4H5 | 4 | 8 | 13 | 49 | 19 | 24 | 30 | 50 |
| B9D1D11F8D8 | 3 | 9 | 14 | 51 | 20 | 25 | 31 | 52 |
| B1D2F7D3B5 | 3 | 9 | 14 | 53 | 21 | 25 | 31 | 54 |

The heavy chain variable region CDRs and the light chain variable region CDRs in Table 1 have been defined by the Kabat numbering system. However, as is well known in the art, CDR regions can also be determined by other systems such as Chothia, and IMGT, AbM, or Contact numbering system/method, based on heavy chain/light chain variable region sequences.

The $V_H$ and $V_L$ sequences (or CDR sequences) of other Anti-IL4Rα antibodies which bind to human IL4Rα can be "mixed and matched" with the $V_H$ and $V_L$ sequences (or CDR sequences) of the anti-IL4Rα antibody of the present disclosure. Preferably, when $V_H$ and $V_L$ chains (or the CDRs within such chains) are mixed and matched, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence.

Accordingly, in one embodiment, an antibody of the disclosure, or an antigen binding portion thereof, comprises:

(a) a heavy chain variable region comprising an amino acid sequence listed above in Table 1; and (b) a light chain variable region comprising an amino acid sequence listed above in Table 1, or the $V_L$ of another Anti-IL4Rα antibody, wherein the antibody specifically binds human IL4Rα.

In another embodiment, an antibody of the disclosure, or an antigen binding portion thereof, comprises:

(a) the CDR1, CDR2, and CDR3 regions of the heavy chain variable region listed above in Table 1; and (b) the CDR1, CDR2, and CDR3 regions of the light chain variable region listed above in Table 1 or the CDRs of another anti-IL4Rα antibody, wherein the antibody specifically binds human IL4Rα.

In yet another embodiment, the antibody, or antigen binding portion thereof, includes the heavy chain variable CDR2 region of anti-IL4Rα antibody combined with CDRs of other antibodies which bind human IL4Rα, e.g., CDR1 and/or CDR3 from the heavy chain variable region, and/or CDR1, CDR2, and/or CDR3 from the light chain variable region of a different anti-IL4Rα antibody.

In addition, it is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, e.g., Klimka et al., *British J. of Cancer* 83 (2): 252-260 (2000); Beiboer et al., *J. Mol. Biol.* 296:833-849 (2000); Rader et al., *Proc. Natl. Acad. Sci. U.S.A.* 95:$8910^{-8915}$ (1998); Barbas et al., *J. Am. Chem. Soc.* 116:2161-2162 (1994); Barbas et al., *Proc. Natl. Acad. Sci. U.S.A.* 92:2529-2533 (1995); Ditzel et al., *J. Immunol.* 157:739-749 (1996); Berezov et al., *BIAjournal* 8: *Scientific Review* 8 (2001); Igarashi et al., *J. Biochem* (Tokyo) 117:452-7 (1995); Bourgeois et al., *J. Virol* 72:807-10 (1998); Levi et al., *Proc. Natl. Acad. Sci. U.S.A.* 90:4374-8 (1993); Polymenis and Stoller, *J. Immunol.* 152: 5218-5329 (1994) and Xu and Davis, *Immunity* 13:37-45 (2000). See also, U.S. Pat. Nos. 6,951,646; 6,914,128; 6,090,382; 6,818,216; 6,156,313; 6,827,925; 5,833,943; 5,762,905 and 5,760,185. Each of these references is hereby incorporated by reference in its entirety.

Accordingly, in another embodiment, antibodies of the disclosure comprise the CDR2 of the heavy chain variable region of the anti-IL4Rα antibody and at least the CDR3 of the heavy and/or light chain variable region of the anti-IL4Rα antibody, or the CDR3 of the heavy and/or light chain variable region of another anti-IL4Rα antibody, wherein the antibody is capable of specifically binding to human IL4Rα. These antibodies preferably (a) compete for binding with IL4Rα; (b) retain the functional characteristics; (c) bind to the same epitope; and/or (d) have a similar binding affinity as the anti-IL4Rα antibody of the present disclosure. In yet another embodiment, the antibodies further may comprise the CDR2 of the light chain variable region of the anti-IL4Rα antibody, or the CDR2 of the light chain variable region of another anti-IL4Rα antibody, wherein the antibody is capable of specifically binding to human IL4Rα. In another embodiment, the antibodies of the disclosure further may include the CDR1 of the heavy and/or light chain variable region of the anti-IL4Rα antibody, or the CDR1 of the heavy and/or light chain variable region of another anti-IL4Rα antibody, wherein the antibody is capable of specifically binding to human IL4Rα.

Conservative Modifications

In another embodiment, an antibody of the disclosure comprises a heavy and/or light chain variable region sequences of CDR1, CDR2 and CDR3 sequences which differ from those of the anti-IL4Rα antibodies of the present disclosure by one or more conservative modifications. It is understood in the art that certain conservative sequence modification can be made which do not remove antigen binding. See, e.g., Brummell et al., (1993) *Biochem* 32:1180-8; de Wildt et al., (1997) *Prot. Eng.* 10:835-41; Komissarov et al., (1997) *J. Biol. Chem.* 272:26864-26870; Hall et al., (1992) *J. Immunol.* 149:1605-12; Kelley and O'Connell (1993) *Biochem.* 32:6862-35; Adib-Conquy et al., (1998) *Int. Immunol.* 10:341-6 and Beers et al., (2000) *Clin. Can. Res.* 6:2835-43.

Accordingly, in one embodiment, the antibody comprises a heavy chain variable region comprising CDR1, CDR2, and CDR3 sequences and/or a light chain variable region comprising CDR1, CDR2, and CDR3 sequences, wherein:

(a) the heavy chain variable region CDR1 sequence comprises a sequence listed in Table 1 above, and/or conservative modifications thereof; and/or (b) the heavy chain variable region CDR2 sequence comprises a sequence listed in Table 1 above, and/or conservative modifications thereof; and/or (c) the heavy chain variable region CDR3 sequence comprises a sequence listed in Table 1 above, and/or conservative modifications thereof; and/or (d) the light chain variable region CDR1, and/or CDR2, and/or CDR3 sequences comprise the sequence(s) listed in Table 1 above; and/or conservative modifications thereof; and (e) the antibody specifically binds human IL4Rα.

The antibody of the present disclosure possesses one or more of the following functional properties described above, such as high affinity binding to human IL4Rα, and blocking activity on IL4Rα-IL4 or IL4Rα-IL13-IL13Rα1 binding.

In various embodiments, the antibody can be, for example, a mouse, human, humanized or chimeric antibody.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the disclosure by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the disclosure can be replaced with other amino acid residues from the same side chain family and the altered antibody can be tested for retained function (i.e., the functions set forth above) using the functional assays described herein.

Engineered and Modified Antibodies

Antibodies of the disclosure can be prepared using an antibody having one or more of the $V_H/V_L$ sequences of the anti-IL4Rα antibody of the present disclosure as starting material to engineer a modified antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

In certain embodiments, CDR grafting can be used to engineer variable regions of antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann et al., (1998) *Nature* 332:323-327; Jones et al., (1986) *Nature* 321:522-525; Queen et al., (1989) *Proc. Natl. Acad*. See also U.S.A. 86:10029-10033; U.S. Pat. Nos. 5,225,539; 5,530,101; 5,585,089; 5,693,762 and 6,180,370).

Accordingly, another embodiment of the disclosure pertains to an isolated monoclonal antibody, or antigen binding portion thereof, comprising a heavy chain variable region comprising CDR1, CDR2, and CDR3 sequences comprising the sequences of the present disclosure, as described above, and/or a light chain variable region comprising CDR1, CDR2, and CDR3 sequences comprising the sequences of the present disclosure, as described above. While these antibodies contain the $V_H$ and $V_L$ CDR sequences of the monoclonal antibody of the present disclosure, they can contain different framework sequences.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat et al., (1991), cited supra; Tomlinson et al., (1992) *J. Mol. Biol.* 227:776-798; and Cox et al., (1994) *Eur. J. Immunol.* 24:827-836; the contents of each of which are expressly incorporated herein by reference. As another example, the germline DNA sequences for human heavy and light chain variable region genes can be found in the Genbank database. For example, the following heavy chain germline sequences found in the HCo7 HuMAb mouse are available in the accompanying Genbank Accession Nos.: 1-69 (NG—0010109, NT—024637 & BC070333), 3-33 (NG—0010109 & NT—024637) and 3-7 (NG—0010109 & NT—024637). As another example, the following heavy chain germline sequences found in the HCo12 HuMAb mouse are available in the accompanying Genbank Accession Nos.: 1-69 (NG—0010109, NT—024637 & BC070333), 5-51 (NG—0010109 & NT—024637), 4-34 (NG—0010109 & NT—024637), 3-30.3 (CAJ556644) & 3-23 (AJ406678).

Antibody protein sequences are compared against a compiled protein sequence database using one of the sequence similarity searching methods called the Gapped BLAST (Altschul et al., (1997), supra), which is well known to those skilled in the art.

Preferred framework sequences for use in the antibodies of the disclosure are those that are structurally similar to the framework sequences used by antibodies of the disclosure. The $V_H$ CDR1, CDR2, and CDR3 sequences can be grafted onto framework regions that have the identical sequence as that found in the germline immunoglobulin gene from which the framework sequence derives, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370).

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as known in the art. Preferably conservative modifications (as known in the art) are introduced. The mutations can be amino acid substitutions, additions or deletions, but are preferably substitutions. Moreover, typically no more than one, two, three, four or five residues within a CDR region are altered.

Accordingly, in another embodiment, the disclosure provides isolated anti-IL4Rα monoclonal antibodies, or antigen binding portions thereof, comprising a heavy chain variable region comprising: (a) a $V_H$ CDR1 region comprising the sequence of the present disclosure, or an amino acid sequence having one, two, three, four or five amino acid substitutions, deletions or additions; (b) a $V_H$ CDR2 region comprising the sequence of the present disclosure, or an amino acid sequence having one, two, three, four or five amino acid substitutions, deletions or additions; (c) a $V_H$ CDR3 region comprising the sequence of the present disclosure, or an amino acid sequence having one, two, three, four or five amino acid substitutions, deletions or additions; (d) a $V_L$ CDR1 region comprising the sequence of the present disclosure, or an amino acid sequence having one, two, three, four or five amino acid substitutions, deletions or additions; (e) a $V_L$ CDR2 region comprising the sequence of the present disclosure, or an amino acid sequence having one, two, three, four or five amino acid substitutions, deletions or additions; and (f) a $V_L$ CDR3 region comprising the sequence of the present disclosure, or an amino acid sequence having one, two, three, four or five amino acid substitutions, deletions or additions.

Engineered antibodies of the disclosure include those in which modifications have been made to framework residues within $V_H$ and/or $V_L$, e.g. to improve the properties of the antibody. Typically, such framework modifications are made to decrease the immunogenicity of the antibody. For example, one approach is to "backmutate" one or more framework residues to the corresponding germline sequence. More specifically, an antibody that has undergone somatic mutation can contain framework residues that differ from the germline sequence from which the antibody is derived. Such residues can be identified by comparing the antibody framework sequences to the germline sequences from which the antibody is derived.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043.

In addition, or as an alternative to modifications made within the framework or CDR regions, antibodies of the disclosure can be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the disclosure can be chemically modified (e.g., one or more chemical moieties can be attached to the antibody) or be modified to alter its glycosylation, again to alter one or more functional properties of the antibody.

In one embodiment, the CHI-hinge region is modified in such that the number of cysteine residues in the hinge region is altered, e.g., increased or decreased. This approach is described further in U.S. Pat. No. 5,677,425. The number of cysteine residues in the CHI-hinge region is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the $C_{H2}$-$C_{H3}$ domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745.

In still another embodiment, the glycosylation of an antibody is modified. For example, a glycosylated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. See, e.g., U.S. Pat. Nos. 5,714,350 and 6,350,861.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase or reduce the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the disclosure to thereby produce an antibody with altered glycosylation. For example, the cell lines Ms704, Ms705, and Ms709 lack the fucosyltransferase gene, FUT8 (a (1,6)-fucosyltransferase), such that antibodies expressed in the Ms704, Ms705, and Ms709 cell lines lack fucose on their carbohydrates. The Ms704, Ms705, and Ms709 FUT8−/−cell lines were created by the targeted disruption of the FUT8 gene in CHO/DG44 cells using two replacement vectors (see U.S. Patent Publication No. 20040110704 and Yamane-Ohnuki et al., (2004) Biotechnol Bioeng 87:614-22). As another example, EP 1,176,195 describes a cell line with a functionally disrupted FUT8 gene, which encodes a fucosyl transferase, such that antibodies expressed in such a cell line exhibit hypofucosylation by reducing or eliminating the α-1,6 bond-related enzyme. EP 1,176,195 also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 describes a variant CHO cell line, Lec13 cells, with reduced ability to attach fucose to Asn(297)-linked carbohydrates, also resulting in hypofucosylation of antibodies expressed in that host cell (see also Shields et al., (2002) J. Biol. Chem. 277:26733-26740). Antibodies with a modified glycosylation profile can also be produced in chicken eggs, as described in PCT Publication WO 06/089231. Alternatively, antibodies with a modified glycosylation profile can be produced in plant cells, such as Lemna. Methods for production of antibodies in a plant system are disclosed in the U.S. patent application corresponding to Alston & Bird LLP 60/836,998, filed on Aug. 11, 2006. The fucose residues of the antibody can be cleaved off using a fucosidase enzyme; e.g., the fucosidase α-L-fucosidase removes fucosyl residues from antibodies (Tarentino et al., (1975) *Biochem.* 14:5516-23).

Another modification of the antibodies herein that is contemplated by this disclosure is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono ($C_1$-$C_{10}$) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the disclosure. See, e.g., EP 0 154 316 and EP 0 401 384.

Antibody's Physical Properties

Antibodies of the disclosure can be characterized by their various physical properties, to detect and/or differentiate different classes thereof.

For example, antibodies can contain one or more glycosylation sites in either the light or heavy chain variable region. Such glycosylation sites may result in increased immunogenicity of the antibody or an alteration of the pK of the antibody due to altered antigen binding (Marshall et al (1972) *Annu Rev Biochem* 41:673-702; Gala and Morrison (2004) *J Immunol* 172:5489-94; Wallick et al (1988) *J Exp Med* 168:1099-109; Spiro (2002) *Glycobiology* 12: 43R-56R; Parekh et al (1985) *Nature* 316:452-7; Mimura et al., (2000) *Mol Immunol* 37:697-706). Glycosylation has been known to occur at motifs containing an N-X-S/T sequence. In some instances, it is preferred to have an anti-IL4Rα antibody that does not contain variable region glycosylation. This can be achieved either by selecting antibodies that do not contain the glycosylation motif in the variable region or by mutating residues within the glycosylation region.

In a preferred embodiment, the antibodies do not contain asparagine isomerism sites. The deamidation of asparagine may occur on N-G or D-G sequences and result in the creation of an isoaspartic acid residue that introduces a link into the polypeptide chain and decreases its stability (isoaspartic acid effect).

Each antibody will have a unique isoelectric point (pI), which generally falls in the pH range between 6 and 9.5. The pI for an IgG1 antibody typically falls within the pH range of 7-9.5 and the pI for an IgG4 antibody typically falls within the pH range of 6-8. There is speculation that antibodies with a pI outside the normal range may have some unfolding and instability under in vivo conditions. Thus, it is preferred to have an anti-IL4Rα antibody that contains a pI value that falls in the normal range. This can be achieved either by selecting antibodies with a pI in the normal range or by mutating charged surface residues.

Nucleic Acid Molecules Encoding Antibodies of the Disclosure

In another aspect, the disclosure provides nucleic acid molecules that encode heavy and/or light chain variable regions, or CDRs, of the antibodies of the disclosure. The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques. A nucleic acid of the disclosure can be, e.g., DNA or RNA and may or may not contain intronic sequences. In a preferred embodiment, the nucleic acid is a cDNA molecule.

Nucleic acids of the disclosure can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), a nucleic acid encoding such antibodies can be recovered from the gene library.

Preferred nucleic acids molecules of the disclosure include those encoding the $V_H$ and $V_L$ sequences of the IL4Rα monoclonal antibody or the CDRs. Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VA region can be converted to a full-length heavy chain gene by operatively linking the $V_H$-encoding DNA to another DNA molecule encoding heavy chain constant regions (CHI, $C_{H2}$ and $C_{H3}$). The sequences of human heavy chain constant region genes are known in the art and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the $V_H$-encoding DNA can be operatively linked to another DNA molecule encoding only the heavy chain CHI constant region.

The isolated DNA encoding the $V_L$ region can be converted to a full-length light chain gene (as well as a Fab light chain gene) by operatively linking the $V_L$-encoding DNA to another DNA molecule encoding the light chain constant region, $C_L$. The sequences of human light chain constant region genes are known in the art and DNA fragments encompassing these regions can be obtained by standard PCR amplification. In preferred embodiments, the light chain constant region can be a kappa or lambda constant region.

To create a scFv gene, the $V_H$- and $V_L$-encoding DNA fragments are operatively linked to another fragment encoding a flexible linker, e.g., encoding the amino acid sequence (Gly4-Ser) 3, such that the $V_H$ and $V_L$ sequences can be expressed as a contiguous single-chain protein, with the $V_L$ and $V_H$ regions joined by the flexible linker (see e.g., Bird et al., (1988) *Science* 242:423-426; Huston et al., (1988) *Proc. Natl. Acad. Sci. USA* 85:5879-5883; McCafferty et al., (1990) *Nature* 348:552-554).

Production of Monoclonal Antibodies of the Disclosure

Monoclonal antibodies (mAbs) of the present disclosure can be produced using the well-known somatic cell hybridization (hybridoma) technique of Kohler and Milstein (1975) *Nature* 256:495. Other embodiments for producing monoclonal antibodies include viral or oncogenic transformation of B lymphocytes and phage display techniques. Chimeric or humanized antibodies are also well known in the art. See e.g., U.S. Pat. Nos. 4,816,567; 5,225,539; 5,530,101; 5,585,089; 5,693,762 and 6,180,370, the contents of which are specifically incorporated herein by reference in their entirety.

Generation of Transfectomas Producing Monoclonal Antibodies of the Disclosure

Antibodies of the disclosure also can be produced in a host cell transfectoma using, for example, a combination of recombinant DNA techniques and gene transfection methods as is well known in the art (e.g., Morrison, S. (1985) *Science* 229:1202). In one embodiment, DNA encoding partial or full-length light and heavy chains obtained by standard molecular biology techniques is inserted into one or more expression vectors such that the genes are operatively linked to transcriptional and translational regulatory sequences. In this context, the term "operatively linked" is intended to mean that an antibody gene is ligated into a vector such that transcriptional and translational control sequences within the vector serve their intended function of regulating the transcription and translation of the antibody gene.

The term "regulatory sequence" is intended to include promoters, enhancers and other expression control elements (e.g., polyadenylation signals) that control the transcription or translation of the antibody genes. Such regulatory sequences are described, e.g., in Goeddel (Gene Expression Technology. Methods in Enzymology 185, Academic Press, San Diego, Calif. (1990)). Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, e.g., the adenovirus major late promoter (AdMLP) and polyoma. Alternatively, nonviral regulatory sequences can be used, such as the ubiquitin promoter or β-globin promoter. Still further, regulatory elements composed of sequences from different sources, such as the SRa promoter system, which contains sequences from the SV40 early promoter and the long terminal repeat of human T cell leukemia virus type 1 (Takebe et al., (1988) *Mol. Cell. Biol.* 8:466-472). The expression vector and expression control sequences are chosen to be compatible with the expression host cell used.

The antibody light chain gene and the antibody heavy chain gene can be inserted into the same or separate expression vectors. In preferred embodiments, the variable regions are used to create full-length antibody genes of any antibody isotype by inserting them into expression vectors already encoding heavy chain constant and light chain constant regions of the desired isotype such that the $V_H$ segment is operatively linked to the CH segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the disclosure in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody.

Preferred mammalian host cells for expressing the recombinant antibodies of the disclosure include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *J. Mol. Biol.* 159:601-621), NSO myeloma cells, COS cells and SP2 cells. In particular for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Bispecific Molecules

In another aspect, the present disclosure features bispecific molecules comprising one or more antibodies of the disclosure linked to at least one other functional molecule, e.g., another peptide or protein (e.g., another antibody or ligand for a receptor) to generate a bispecific molecule that binds to at least two different binding sites or target molecules. Thus, as used herein, "bispecific molecule" includes molecules that have three or more specificities.

In an embodiment, a bispecific molecule has, in addition to an anti-Fc binding specificity and an anti-IL4Rα binding specificity, a third specificity.

Bispecific molecules may be in many different formats and sizes. At one end of the size spectrum, a bispecific molecule retains the traditional antibody format, except that, instead of having two binding arms of identical specificity, it has two binding arms each having a different specificity. At the other extreme are bispecific molecules consisting of two single-chain antibody fragments (scFv's) linked by a peptide chain, a so-called Bs(scFv) 2 construct. Intermediate-sized bispecific molecules include two different F(ab) fragments linked by a peptidyl linker. Bispecific molecules of these and other formats can be prepared by genetic engineering, somatic hybridization, or chemical methods. See, e.g., Kufer et al, cited supra; Cao and Suresh, *Bioconjugate Chemistry,* 9 (6), 635-644 (1998); and van Spriel et al., *Immunology Today,* 21 (8), 391-397 (2000), and the references cited therein.

Immunoconjugates

Antibodies of the disclosure can be conjugated to a therapeutic agent to form an immunoconjugate such as an antibody-drug conjugate (ADC). Suitable therapeutic agents include cytotoxins, alkylating agents, DNA minor groove binders, DNA intercalators, DNA crosslinkers, histone deacetylase inhibitors, nuclear export inhibitors, proteasome inhibitors, topoisomerase I or II inhibitors, heat shock protein inhibitors, tyrosine kinase inhibitors, antibiotics, and anti-mitotic agents. In the ADC, the antibody and therapeutic agent preferably are conjugated via a linker cleavable such as a peptidyl, disulfide, or hydrazone linker. More preferably, the linker is a peptidyl linker such as Val-Cit, Ala-Val, Val-Ala-Val, Lys-Lys, Pro-Val-Gly-Val-Val, Ala-Asn-Val, Val-Leu-Lys, Ala-Ala-Asn, Cit-Cit, Val-Lys, Lys, Cit, Ser, or Glu. The ADCs can be prepared as described in U.S. Pat. Nos. 7,087,600; 6,989,452; and 7,129,261; PCT Publications WO 02/096910; WO 07/038,658; WO 07/051,081; WO 07/059,404; WO 08/083,312; and WO 08/103,693; U.S. Patent Publications 20060024317; 20060004081; and 20060247295; the disclosures of which are incorporated herein by reference.

Antibody-Encoding or Antibody-Bearing Oncolytic Virus

An oncolytic virus preferentially infects and kills cancer cells. Antibodies of the present disclosure can be used in conjunction with oncolytic viruses. Alternatively, oncolytic viruses encoding antibodies of the present disclosure can be introduced into human body.

Chimeric Antigen Receptor

Also provided herein are a chimeric antigen receptor (CAR) containing an anti-IL4Rα scFv, the anti-IL4Rα scFv comprising CDRs and heavy/light chain variable regions described herein.

The anti-IL4Rα CAR may comprise (a) an extracellular antigen binding domain comprising an anti-IL4Rα scFv; (b) a transmembrane domain; and (c) an intracellular signaling domain.

The CAR may contain a signal peptide at the N-terminus of the extracellular antigen binding domain that directs the nascent receptor into the endoplasmic reticulum, and a hinge peptide at the N-terminus of the extracellular antigen binding domain that makes the receptor more available for binding. The CAR preferably comprises, at the intracellular signaling domain, a primary intracellular signaling domain and one or more co-stimulatory signaling domains. The mainly used and most effective primary intracellular signaling domain is CD3-zeta cytoplasmic domain which contains ITAMs, the phosphorylation of which results in T cell activation. The co-stimutory signaling domain may be derived from the co-stimulatory proteins such as CD28, CD137 and OX40.

The CARs may further add factors that enhance T cell expansion, persistence, and anti-tumor activity, such as cytokines, and co-stimulatory ligands.

Also provided are engineered immune effector cells, comprising the CAR provided herein. In some embodiments, the immune effector cell is a T cell, an NK cell, a peripheral blood mononuclear cell (PBMC), a hematopoietic stem cell, a pluripotent stem cell, or an embryonic stem cell. In some embodiments, the immune effector cell is a T cell.

Pharmaceutical Compositions

In another aspect, the present disclosure provides a pharmaceutical composition comprising one or more antibodies ((or antigen-binding portion thereof, or the bispecifics, CAR-T cells, oncolytic viruses, immunoconjugates) of the present disclosure formulated together with a pharmaceutically acceptable carrier. The antibodies (or antigen-binding portion thereof, or the bispecifics, CAR-T cells, oncolytic viruses, immunoconjugates) can be dosed sperapartely when the composition contains more than one antibody (or antigen-binding portion thereof, or the bispecifics, CAR-T cells, oncolytic viruses, immunoconjugates). The composition may optionally contain one or more additional pharmaceutically active ingredients, such as another antibody or a drug, such as an anti-tumor drug or an anti-allergic agent.

The pharmaceutical composition can comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients are taught in Gennaro, ed., Remington: *The Science and Practice of Pharmacy,* 20th Ed. (Lippincott Williams & Wilkins 2003), the disclosure of which is incorporated herein by reference.

Preferably, the pharmaceutical composition is suitable for intravenous, intramuscular, subcutaneous, parenteral, spinal or epidermal administration (e.g., by injection or infusion). Depending on the route of administration, the active ingredient can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, an antibody of the disclosure can be administered via a non-parenteral route, such as a topical, epidermal or mucosal route of administration, e.g., intranasally, orally, vaginally, rectally, sublingually or topically.

Pharmaceutical compositions can be in the form of sterile aqueous solutions or dispersions. They can also be formulated in a microemulsion, liposome, or other ordered structure suitable to high drug concentration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01% to about ninety-nine percent of active ingredient, preferably from about 0.1% to about 70%, most preferably from about 1% to about 30% of active ingredient in combination with a pharmaceutically acceptable carrier.

Dosage regimens are adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active ingredient calculated to produce the desired therapeutic effect in association with the required pharmaceutical carrier. Alternatively, antibody can be administered as a sustained release formulation, in which case less frequent administration is required.

For administration of the composition, the dosage may range from about 0.0001 to 100 mg/kg, and more usually 0.01 to 5 mg/kg, of the host body weight. For example, dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-IL4Rα antibody of the disclosure include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks. In some methods, dosage is adjusted to achieve a plasma antibody concentration of about 1-1000 μg/ml and in some methods about 25-300 μg/ml.

A "therapeutically effective dosage" of an anti-IL4Rα antibody, or the antigen-binding portion thereof, or the bispecifics, CAR-T cells, oncolytic viruses, immunoconjugates of the disclosure preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective dosage" preferably inhibits tumor growth by at least about 20%, more preferably by at least about 40%, even more preferably by at least about 60%, and still more preferably by at least about 80% relative to untreated subjects. A therapeutically effective amount of a therapeutic antibody can decrease tumor size, or otherwise ameliorate symptoms in a subject, which is typically a human or can be another mammal.

The pharmaceutical composition can be a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., Sustained and Controlled Release Drug Delivery Systems, J. R. Robinson, ed., Marcel Dekker, Inc., New York, 1978.

Therapeutic compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparatuses (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the monoclonal antibodies of the disclosure can be formulated to ensure proper distribution in vivo. For example, to ensure that the therapeutic antibody of the disclosure cross the blood-brain barrier, they can be formulated in liposomes, which may additionally comprise targeting moieties to enhance selective transport to specific cells or organs. See, e.g. U.S. Pat. Nos. 4,522,811; 5,374,548; 5,416,016; and 5,399,331; V. V. Ranade (1989) *J. Clin. Pharmacol.* 29:685; Umezawa et al., (1988) *Biochem. Biophys. Res. Commun.* 153:1038; Bloeman et al., (1995) *FEBS Lett.* 357:140; M. Owais et al., (1995) *Antimicrob. Agents Chemother.* 39:180; Briscoe et al., (1995) *Am. J. Physiol.* 1233:134; Schreier et al., (1994) *J. Biol. Chem.* 269:9090; Keinanen and Laukkanen (1994) *FEBS Lett.* 346:123; and Killion and Fidler (1994) *Immunomethods* 4:273.

Uses and Methods of the Disclosure

The composition comprising the antibodies or the antigen-binding portion thereof, or the bispecifics, CAR-T cells, oncolytic viruses, immunoconjugates of the present disclosure have numerous in vitro and in vivo utilities involving, for example, treatment of allergic diseases with excessive IL4 and/or IL13 signaling.

Given the ability of anti-IL4Rα antibodies of the disclosure to block IL4Rα binding with IL4 or IL13-IL13Rα1 to reduce type 2 immunity, the disclosure provides methods for treating type 2 immunity related allergic diseases, comprising administering to the subject the composition of the disclosure. The allergic diseases may be atopic dermatitis, anaphylaxis, allergic rhinitis, or allergic asthma.

In another respect, as the IL4 or IL13 signaling activates STAT6 molecules and an STAT6 inhibitor has been found to inhibit cancer cell growth, the disclosure provides a method for inhibiting growth of tumor cells in a subject comprising administering to the subject the composition of the disclosure such that growth of the tumor is inhibited in the subject. Non-limiting examples of tumors that can be treated by antibodies of the disclosure include, but not limited to, melanoma, lung cancer, kidney cancer, prostate cancer, cervical cancer, colorectal cancer, gastric cancer, pancreatic cancer, varian cancer and urothelial cancer.

In another aspect, the disclosure provides a method for reducing or inhibiting activation of cells responsive to IL-4 or IL-13. In some embodiments, inhibiting activation comprises inhibiting cytokine production or secretion. In some embodiments, inhibiting activation comprises inhibiting proliferation. Cells responsive to IL-4 through stimulation of hybrid IL-4Rα/γC receptors include, without limitation, B cells, eosinophils, and macrophages. Cells responsive to IL-13 through stimulation of hybrid IL-4Rα/IL-3Rα1 receptors include, without limitation, fibroblasts and smooth muscle cells. Thus, in an embodiment, the disclosure provides a method of inhibiting smooth muscle cell proliferation. In another embodiment, the invention provides a method of inhibiting fibroblast proliferation.

In yet another aspect, the disclosure provides diagnostic methods, compositions and kits. In an embodiment, an antibody of the disclosure is used to determine the presence and expression of IL4Rα in a cell or tissue. In an embodiment, the diagnostic indicates prognosis and/or directs treatment and/or follow-up treatment. For example, IL4Rα overexpression in human bladder cancer is observed to correlate with the pathological grade and stage of the disease. In an embodiment, an antibody of the disclosure is used to diagnose the grade and stage of bladder cancer. High expression of IL-4Rα is observed to be correlated with increased recurrence or oral cancer. In an embodiment, an antibody of the disclosure is employed in an oral cancer diagnostic kit or method to determine prognosis and appropriate treatment and followup. Tumor expression of IL-4Rα is inversely correlated with survival in patients undergoing surgical resection for epithelial malignant pleural mesothelioma (MPM). In an embodiment, an antibody of the disclosure is employed in a diagnostic kit or method to determine prognosis and appropriate treatment and/or followup of MPM.

Combination Therapy

In one aspect, the disclosure provides combination therapy in which the anti-IL4Rα antibodies, or antigen-binding portion thereof, or the bispecifics, oncolytic viruses of the present disclosure are co-administered with one or more additional agents that are effective in alleviating type 2 immunity related allergic symptoms. Such agents may be antihistamines that target $H_1$ histamine receptor, clinically used for allergic rhinitis treatment, or corticosteroids, agonists of beta-adrenergic receptors and drugs targeting cyc-LTs, which are clinically for asthma treatment. Omalizumab, an anti-IgE antibody, may be also used with the antibodies or antigen-binding portion thereof, or the bispecifics, oncolytic viruses of the present disclosure for treatment of allergic diseases. In certain embodiments, the subject is human.

In another aspect, the disclosure provides methods of combination therapy in which the anti-IL4Rα antibodies, or antigen-binding portion thereof, or the bispecifics, CAR-T cells, oncolytic viruses, immunoconjugates of the present disclosure are co-administered with one or more additional antibodies that are effective in inhibiting tumor growth in a subject. In one embodiment, the disclosure provides a method for inhibiting tumor growth in a subject comprising administering to the subject an anti-IL4Rα antibody (or antigen-binding portion thereof, or bispecific molecules, oncolytic virus, CAR-T cells, immunoconjugates) and one or more additional antibodies, such as an anti-OX40 antibody, an anti-TIM-3 antibody, an anti-CD137 antibody, an anti-GITR antibody, an anti-LAG-3 antibody, an anti-PD-L1 antibody, and anti-PD-1 antibody. In certain embodiments, the subject is human. The IL4Rα pathway blockade can also be further combined with standard cancer treatments. For example, IL4Rα pathway blockade can be combined with LAG-3 and/or PD-1 blockade and also chemotherapeutic regimes. For example, a chemotherapeutic agent can be administered with the Anti-IL4Rα antibodies, which may be a cytotoxic agent. For example, epitubicin, oxaliplatin, and 5-FU are administered to patients receiving Anti-IL4Rα therapy. Optionally, the combination of anti-IL4Rα and one or more additional antibodies (e.g., anti-LAG-3 and/or anti-PD-1 antibodies) can be further combined with an immunogenic agent, such as cancerous cells, purified tumor antigens (including recombinant proteins, peptides, and carbohydrate molecules), and cells transfected with genes encoding immune stimulating cytokines (He et al., (2004) *J. Immunol.* 173:4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF. Other therapies that may be combined with Anti-IL4Rα antibody includes, but not limited to, interleukin-2 (IL-2) administration, radiation, surgery, or hormone deprivation.

The combination of therapeutic agents discussed herein can be administered concurrently as a single composition in a pharmaceutically acceptable carrier, or concurrently as separate compositions with each agent in a pharmaceutically acceptable carrier. In another embodiment, the combination of therapeutic agents can be administered sequentially.

Furthermore, if more than one dose of the combination therapy is administered sequentially, the order of the sequential administration can be reversed or kept in the same order at each time point of administration, sequential administrations can be combined with concurrent administrations, or any combination thereof.

The present disclosure is further illustrated by the following examples, which should not be construed as further limiting. The contents of all figures and all references, Genbank sequences, patents and published patent applications cited throughout this application are expressly incorporated herein by reference.

EXAMPLES

Example 1 Generation of Mouse Anti-IL4Rα Monoclonal Antibodies Using Hybridoma Technology Immunization Mice were immunized according to the method as described in E Harlow, D. Lane, Antibody: A Laboratory Manual, Cold Spring Harbor Laboratory Press, Cold Spring Harbor, N.Y., 1998. Recombinant human IL4Rα-his protein (Sino biological inc., Cat #10402-H08H) was used as the immunogen, and in house made human IL4Rα-his protein (amino acid sequence set forth in SEQ ID NO: 57) was used for determining anti-sera titer and for screening hybridomas secreting antigen-specific antibodies. Immunizing dosages contained 20 μg human IL4Rα-his protein/mouse/injection for both primary and boost immunizations. To increase immune response, the complete Freud's adjuvant and incomplete Freud's adjuvant (Sigma, St. Louis, Mo., USA) were used respectively for primary and boost immunizations. Briefly, adjuvant-antigen mixture was prepared by first gently mixing the adjuvant in a vial using a vortex. The desired amount of adjuvant was transferred to an autoclaved 1.5 mL micro-centrifuge tube. The antigen was prepared in PBS or saline with concentration ranging from 0.2-0.3 mg/ml. The calculated amount of antigen was then added to the micro-centrifuge tube with the adjuvant, and the resulting mixture was mixed by gently vortexing for 2 minutes to generate water-in-oil emulsions. The adjuvant-antigen emulsion was then drawn into the proper syringe for animal injection. A total of 20 μg of antigen was injected in a volume of 150-200 μl. Each animal was immunized, and then boosted for 2 to 3 times depending on the anti-sera titer. Animals with good titers were given a final boost by intraperitoneal injection before fusion.

Hybridoma Fusion and Screening

Cells of murine myeloma cell line (SP2/0-Ag14, ATCC #CRL-1581) were cultured to reach the log phase stage right before fusion. Spleen cells from immunized mice were prepared sterilely and fused with myeloma cells according to the method as described in Kohler G, and Milstein C, "Continuous cultures of fused cells secreting antibody of predefined specificity," Nature, 256:495-497 (1975). Fused "hybrid cells" were subsequently dispensed into 96-well plates in DMEM/20% FCS/HAT medium. Surviving hybridoma colonies were observed under the microscope seven to ten days post fusion. After two weeks, the supernatant from each well was subjected to ELISA-based screening using recombinant human IL4Rα-his protein. Briefly, ELISA plates were coated with 60 μl of human IL4Rα-his (2.0 μg/ml in PBS) overnight at 4° C. Plates were washed 4 times with PBST and blocked with 200 μl blocking buffer (5% w/v non-fatty milk in PBST). Diluted hybridoma supernatant (60 μl) was added to each well and incubated at 37° C. for 40 minutes. Plates were then washed 4 times, HRP-goat anti-mouse-IgG (Jackson Immuno research, Cat #115-036-071) was used for detection, and binding ODs were observed at 450 nm. Positive hybridoma secreting antibody that binds to human IL4Rα-his protein were then selected and transferred to 24-well plates. Hybridoma clones producing antibodies that showed high specific human IL4Rα binding and IL4Rα-IL4 or IL4Rα-13Rα1-IL13 blocking activities were subcloned by limiting dilution to ensure the clonality of the cell line, and then monoclonal antibodies were purified. Briefly, Protein A sepharose column (from bestchrom (Shanghai) Biosciences, Cat #AA0273) was washed using PBS buffer in 5 to 10 column volumes. Cell supernatants were passed through the columns, and then the columns were washed using PBS buffer until the absorbance for protein reached the baseline. The columns were eluted with elution buffer (0.1 M Glycine-HCl, pH 2.7), and immediately collected into 1.5 ml tubes with neutralizing buffer (1 M Tris-HCl, pH 9.0). Fractions containing immunoglobulins were pooled and dialyzed in PBS overnight at 4° C. Subsequently, the in vitro functional activities of purified monoclonal antibodies were characterized as follows.

Example 2 Binding Affinity Determination of Mouse Anti-IL4Rα Monoclonal Antibodies Using BIACORE Surface Plasmon Resonance The purified anti-IL4Rα mouse monoclonal antibodies (mAbs) generated in Example 1 were characterized for binding affinity and binding kinetics by Biacore T200 system (GE healthcare, Pittsburgh, PA, USA).

Briefly, goat anti-mouse IgG (GE healthcare, Cat #BR100838, Mouse Antibody Capture Kit) was covalently linked to a CM5 chip (carboxy methyl dextran coated chip) via primary amines, using a standard amine coupling kit provided by Biacore (GE healthcare, Pittsburgh, PA, USA). Un-reacted moieties on the biosensor surface were blocked with ethanolamine. Then, purified anti-IL4Rα antibodies of the disclosure at the concentration of 66.67 nM and an anti-IL4Rα benchmark (Dupilumab®, also referred to as BM) at 10 μg/ml, were flowed onto the chip at a flow rate of 10 μL/min. Then, serially diluted recombinant human IL4Rα-his (in house made, amino acid sequence set forth in SEQ ID NO: 57), cynomolgus monkey IL4Rα-his protein (Sino biological inc., Cat #90897-C08H), or marmoset monkey IL4Rα-his protein (Custom made by Sino biological inc., also referred to as cal-IL4Rα-his, amino acid sequence set forth in SEQ ID NO: 58) in HBS EP buffer (provided by Biacore) was flowed onto the chip at a flow rate of 30 μL/min. The antigen-antibody association kinetics was followed for 2 minutes and the dissociation kinetics was followed for 10 minutes. The association and dissociation curves were fit to a 1:1 Langmuir binding model using BIA evaluation software. The $K_D$, $K_a$ and $K_d$ values were determined and summarized in Table 2 below.

TABLE 2

Binding affinity of mouse anti-IL4Rα antibodies

| | Kinetics on Biacore | | | | |
|---|---|---|---|---|---|
| | Human IL4Rα | | | Cynomolgus IL4Rα | Cal-IL4Rα |
| Mouse mAb ID# | $K_a$ ($M^{-1}s^{-1}$) | $K_d$ ($s^{-1}$) | $K_D$ (M) | $K_D$ (M) | $K_D$ (M) |
| B1D2F7D3B5 | 4.27E+05 | 2.66E−04 | 6.23E−10 | * | * |
| B8G11F2B7G5E8 | 1.97E+05 | 2.93E−04 | 1.49E−09 | * | * |
| B9D1D11F8D8 | 4.18E+05 | 2.74E−04 | 6.55E−10 | * | * |
| C2C1A1A1 | 2.90E+05 | 1.16E−05 | 4.01E−11 | * | * |
| C2B2F7B7 | 2.51E+05 | 1.39E−04 | 5.54E−10 | * | * |
| Benchmark | 2.22E+05 | 3.77E−05 | 1.70E−10 | * | * |

* Not tested.

All the mouse antibodies of the disclosure specifically bound to human IL4Rα, and most of them showed comparable or higher binding affinity as compared to the benchmark.

Example 3 IL4Rα Binding Activity of Mouse Anti-IL4Rα Antibodies

The binding activity of mouse anti-IL4Rα antibodies of the disclosure to IL4Rα was determined by Capture ELISA, Flow Cytometry (FACS) and indirect ELISA.

3.1 Capture ELISA

Briefly, 96-well plates were coated with 2 μg/ml goat anti-mouse IgG Fcγ fragment specific (Jackson Immuno Research, Cat #115-005-008) in PBS, 100 μl/well, overnight at 4° C. Plates were washed once with wash buffer (PBS+0.05% w/v Tween-20, PBST) and then blocked with 200 μl/well blocking buffer (5% w/v non-fatty milk in PBST) for 2 hours at 37° C. Plates were washed again and incubated with 100 μl/well serially diluted anti-IL4Rα antibodies of the disclosure, the benchmark or negative control hIgG (human immunoglobulin (pH4) for intravenous injection, Hualan Biological Engineering Inc.) (5-fold dilution in 2.5% w/v non-fatty milk in PBST, starting at 66.7 nM) for 40 minutes at 37° C., and then washed 4 times again. Plates containing captured anti-IL4Rα antibodies were incubated with biotin-labeled human IL4Rα-his protein (in house made with SEQ ID NO: 57, 0.14 nM in 2.5% w/v non-fatty milk in PBST, 100 μl/well) for 40 minutes at 37° C., washed 4 times, and incubated with streptavidin conjugated HRP (1:10000 dilution in PBST, Jackson Immuno Research, Cat #016-030-084, 100 μl/well) for 40 minutes at 37° C. After a final wash, plates were incubated with 100 μl/well ELISA substrate TMB (Innoreagents, Cat #TMB-S-002). The reaction was stopped in 10 minutes at 25° C. with 50 μl/well 1M H2S04, and the absorbance was read at 450 nm. Data was analyzed using Graphpad Prism software and $EC_{50}$ values were reported.

3.2 Cell Based Binding FACS

The binding activity of the mouse anti-IL4Rα antibodies to IL4Rα expressed on 293F-IL4Rα cell surface was tested by flow cytometry (FACS). Briefly, 293F cells (Thermofisher Inc., Cat #11625019) were transfected with a pCMV-T-P plasmid construct with the nucleotide encoding human IL4Rα (amino acid residues 1-825 of uniprot #P24394-1) between EcoRI and XbaI, and a stable cell pool named 293F-IL4Rα was chosen for subsequent cell based binding and cell based ligand blocking FACS assays. The 293F-IL4Rα cells were harvested from cell culture flasks, washed twice and resuspended in phosphate buffered saline (PBS) containing 2% v/v Fetal Bovine Serum (FACS buffer). Then, $2\times10^5$ cells per well in 96 well-plates were incubated in 100 μL of the anti-IL4Rα antibodies or controls of various concentrations (starting at 80 nM with a 4-fold serial dilution) in FACS buffer for 40 minutes on ice. Cells were washed twice with FACS buffer, and added with 100 μL/well R-Phycoerythrin AffiniPure F(ab')$_2$ Fragment Goat Anti-Mouse IgG (H+L) (1:1000 dilution in FACS buffer, Jackson Immunoresearch, Cat #115-116-146). Following an incubation of 40 minutes at 4° C. in dark, cells were washed three times and resuspended in FACS buffer. Fluorescence was measured using a Becton Dickinson FACS Canto II-HTS equipment. Data was analyzed using Graphpad Prism software and $EC_{50}$ values were reported.

3.3 Indirect ELISA

The anti-IL4Rα antibodies' cross-reaction with cynomolgus IL4Rα proteins or cal-IL4Rα-his proteins were measured. Briefly, 96-well micro plates were coated with 2 μg/ml cynomolgus IL4Rα-his protein (Sino biological inc., Cat #90897-C08H) or 0.2 μg/ml cal-IL4Rα-his protein (Custom made by Sino biological inc., Cat #BAX2) in carbonate/bicarbonate buffer (pH 9.6), 100 μl/well, for 2 hours at 37° C. ELISA plates were washed once with wash buffer (PBS+0.05% w/v Tween-20, PBST) and then blocked with 200 μl/well blocking buffer (5% w/v non-fatty milk in PBST) for 2 hours at 37° C. Plates were washed again and incubated with 100 μl/well serially diluted anti-IL4Rα antibodies of the disclosure or controls (0.004-66.7 nM, 5-fold serial dilution in 2.5% w/v non-fatty milk in PBST, starting at 66.7 nM) for 40 minutes at 37° C. ELISA plates were washed 4 times and incubated with Peroxidase AffiniPure Goat Anti-Mouse IgG, Fcγ Fragment Specific (1:5000 dilution in PBST buffer, Jackson Immunoresearch, Cat #115-035-071, 100 μl/well) for 40 minutes at 37° C. After a final wash, plates were incubated with 100 μl/well TMB (Innoreagents). The reaction was stopped 3-10 minutes later at 25° C. with 50 μl/well 1M $H2SO_4$, and the absorbance was read at 450 nm. Data was analyzed using Graphpad Prism software and ECso values were reported.

The results of the three assays were shown in Table 3 and FIGS. 1A-1C, 2A-2D and 3.

It can be seen that the mouse anti-IL4Rα antibodies of the disclosure specifically bound human IL4Rα with high binding capacity, and some of them bound to monkey IL4Rα proteins with higher binding activity than the benchmark.

TABLE 3

Binding Activity of mouse anti-IL4Rα antibodies

| Mouse mAb ID# | Binding Capture ELISA ($EC_{50}$, nM) | Cell binding FACS ($EC_{50}$, nM) | Cyno-cross indirect ELISA ($EC_{50}$, nM) | Cal-cross indirect ELISA ($EC_{50}$, nM) |
|---|---|---|---|---|
| B1D2F7D3B5 | 0.06 | 0.25 | No binding | * |
| B8G11F2B7G5E8 | 0.04 | 0.25 | 0.29 | * |
| B9D1D11F8D8 | 0.07 | 0.22 | No binding | * |
| C2C1A1A1 | 0.08 | 0.16 | 0.33 | * |
| C2B2F7B7 | 0.13 | 0.18 | 108.2 | * |
| Benchmark | 0.05 | 0.08 | 0.95 | * |

* Not tested yet.

Example 4 Blocking Activity of Mouse Anti-IL4Rα Antibodies on IL4Rα-Benchmark or IL4Rα-IL4 Interaction 4.1 Ligand Blocking ELISA The activity of the anti-IL4Rα antibodies of the disclosure to block IL4-IL4Rα interaction was measured in a competitive ELISA assay. Briefly, 100 μl human IL4Rα-his proteins (prepared in-house with SEQ ID NO: 57) were coated on 96-well micro plates at 2 μg/mL in PBS overnight at 4° C. The next day, plates were washed with wash buffer (PBS+0.05% w/v Tween-20, PBST), and blocked with 5% w/v non-fatty milk in PBST for 2 hours at 37° C. Plates were then washed again using wash buffer.

Serially diluted anti-IL4Rα antibodies or the controls (starting at 80 nM with a 4-fold serial dilution) in 2.5% w/v non-fatty milk in PBST, 100 μl per well, were added to the IL4Rα bound plates, and incubated with the human IL4Rα-his proteins at 37° C. for 40 minutes. Plates were washed 4 times using wash buffer, and then added and incubated for 40 minutes at 37° C. with 100 μl/well of 0.56 nM biotin-labeled human IL4 protein (Sino biological inc., Cat #11846-HNAE). Plates were washed again using wash buffer. Thereafter, the plates were added with 100 μl/well of streptavidin conjugated HRP (1:10000 dilution in PBST buffer, Jackson Immunoresearch, Cat #016-030-084) and incubated for 40 minutes at 37° C. Plates were washed again using wash buffer. Finally, TMB was added and the reaction was stopped using 1M $H_2SO_4$, and the absorbance was read at 450 nm. Data was analyzed using Graphpad Prism software and $IC_{50}$ values were reported.

4.2 Benchmark Blocking ELISA

The ability of the anti-IL4Rα antibodies of the disclosure to block benchmark-human IL4Rα binding was measured in a competitive ELISA assay. Briefly, the benchmark was coated on 96-well micro plates at 2 μg/mL in PBS, 100 μl per well, and incubated overnight at 4° C. The next day, plates were washed with wash buffer (PBS+0.05% w/v Tween-20, PBST), and blocked with 5% w/v non-fatty milk in PBST for 2 hours at 37° C. During plate blocking, the anti-IL4Rα antibodies of the disclosure or controls were diluted with biotin labeled human IL4Rα-his proteins (prepared in-house with SEQ ID NO: 57, 0.55 nM in 2.5% w/v non-fatty milk in PBST), starting at 100 nM with a 4-fold serial dilution, and incubated at 25° C. for 40 minutes. After plate washing, the antibody/IL4Rα-his mixtures were added to benchmark coated plates, 100 μl per well. After incubation at 37° C. for 40 minutes, plates were washed using wash buffer. Then the plates were added and incubated with 100 μl/well streptavidin conjugated HRP for 40 minutes at 37° C. to detect biotin-labeled human IL4Rα-his bound to plates. Plates were washed again using wash buffer. Finally, TMB was added and the reaction was stopped using 1M $H_2SO_4$, and the absorbance was read at 450 nm. Data was analyzed using Graphpad Prism software and $IC_{50}$ values were reported.

4.3 Cell-Based Ligand-Blocking FACS

The activity of the anti-IL4Rα antibodies to block IL4 protein binding to cell surface IL4Rα was evaluated by Flow Cytometry (FACS), using the 293F-IL4Rα cells prepared above.

Briefly, 293F-IL4Rα cells were harvested from cell culture flasks, washed twice and resuspended in PBS containing 2% v/v Fetal Bovine Serum (FACS buffer). Then, $1\times10^5$ cells per well in 96 well-plates were incubated in 100 μL of the anti-IL4Rα antibodies or controls of various concentrations (starting at 80 nM with a 4-fold serial dilution) in FACS buffer for 40 minutes on ice. The plates were washed twice with FACS buffer, and added and incubated for 40 minutes at 4° C. in dark with 100 μl/well 1.67 nM biotin-labeled human IL4 protein (Sino biological inc., Cat #11846-HNAE). The plates were washed twice with FACS buffer, and then added and incubated for 40 minutes at 4° C. in dark with 100 μl/well R-Phycoerythrin Streptavidin (1:500 dilution in FACS buffer, Jackson Immunoresearch, Cat #016-110$^{-084}$). Cells were washed twice and resuspended in FACS buffer. Fluorescence was measured using a Becton Dickinson FACS Canto II-HTS equipment. Data was analyzed using Graphpad Prism software and $IC_{50}$ values were reported.

The results of the three assays were shown in Table 4 below and FIGS. 4A-4B, 5A-5B and 6A-6C.

Figure 4A:
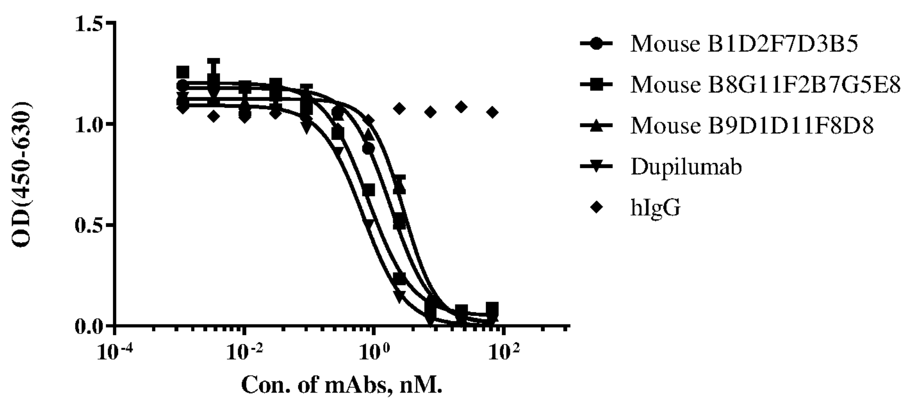
FIGS. 4A-4B show the blocking ability of mouse antibodies B1D2F7D3B5, B8G11F2B7G5E8 and B9D1D11F8D8 (A), C2C1A1A1 and C2B2F7B7 (B) on human IL4Rα-IL4 interaction.
Figure 4B:
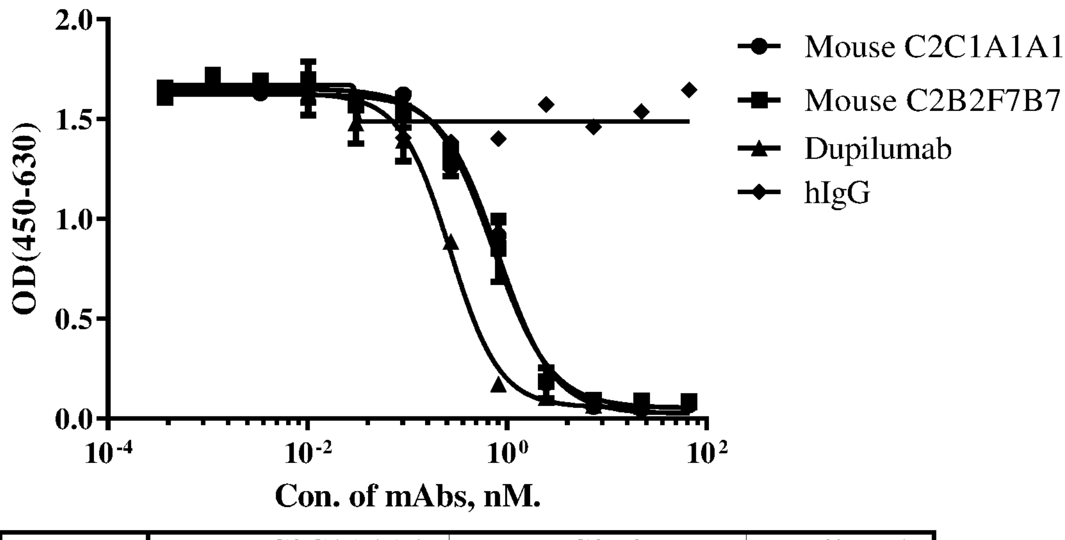

It can be seen from Table 4 and FIG. 4A-4B that all anti-IL4Rα antibodies of the disclosure were capable of blocking human IL4-human IL4Rα interaction with comparable blocking activity to the benchmark.

Figure 5A:
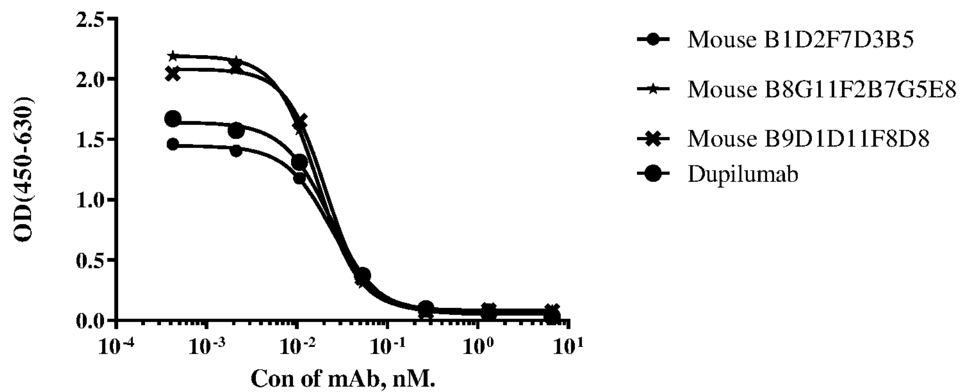
FIGS. 5A-5B show the ability of mouse antibodies B1D2F7D3B5, B8G11F2B7G5E8 and B9D1D11F8D8 (A), C2C1A1A1 and C2B2F7B7 (B) to block Benchmark-human IL4Rα binding.
Figure 5B:
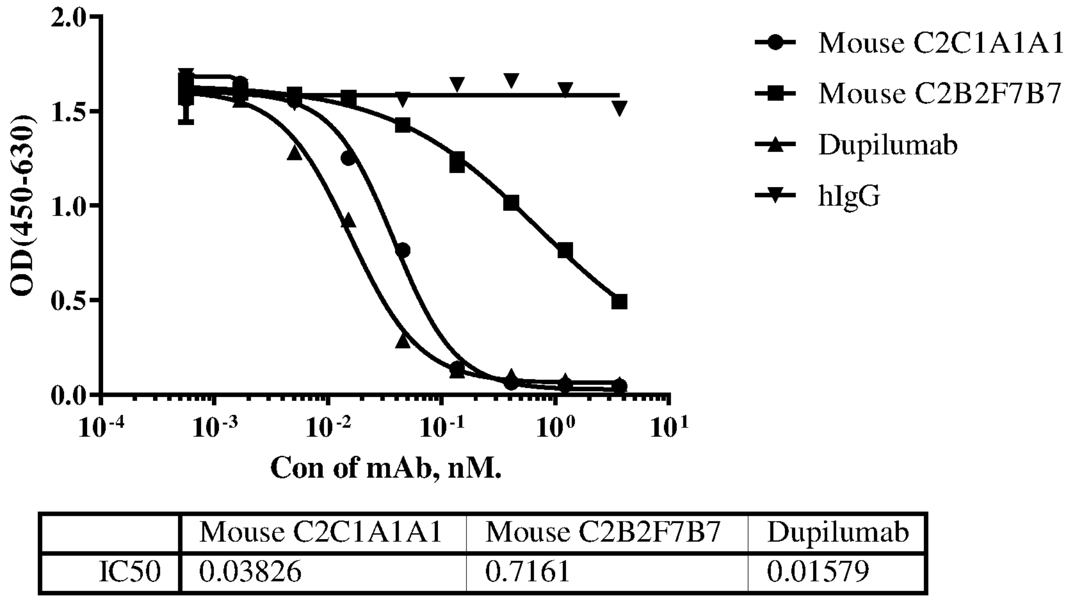

FIGS. 5A and 5B showed that some of the antibodies of the disclosure were able to block human IL4Rα-benchmark binding, suggesting that they might bind to the same or similar epitope as the benchmark did.

Figure 6A:
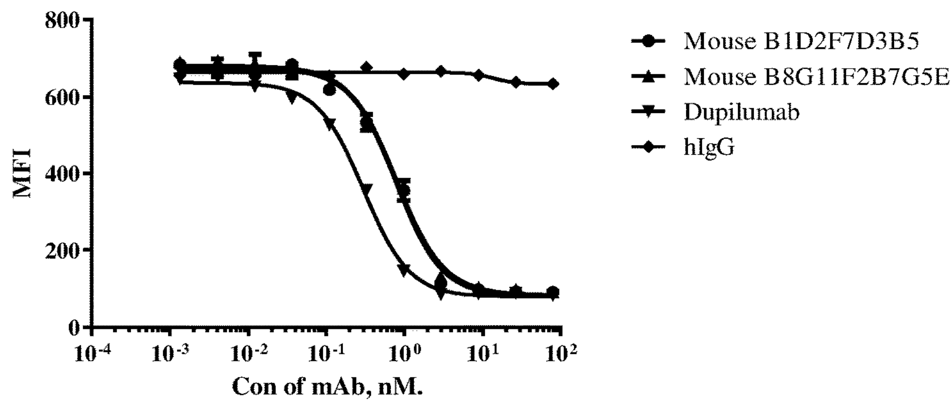
FIGS. 6A-6C show the blocking ability of mouse antibodies BID2F7D3B5 and B8G11F2B7G5E8 (A), B9D1D11F8D8 (B), C2C1A1A1 and C2B2F7B7 (C) on interaction of human IL4 with cell surface human IL4Rα.
Figure 6B:
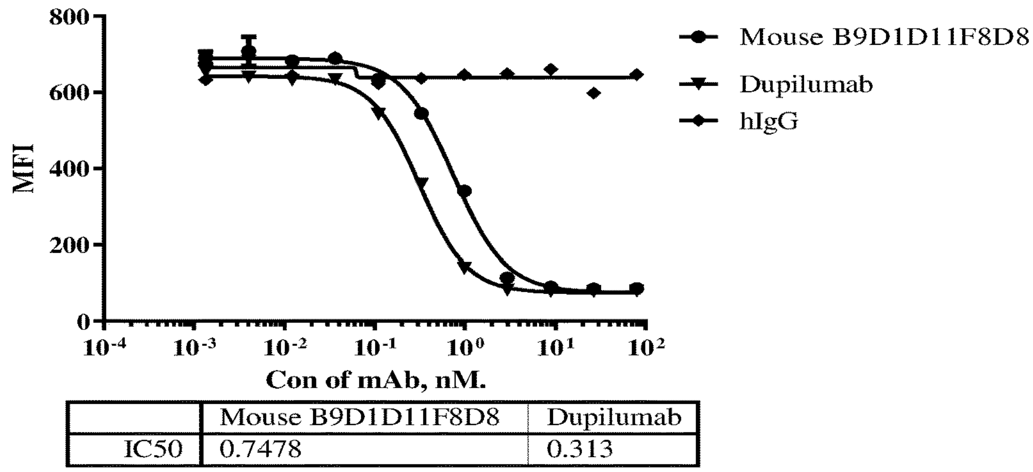
Figure 6C:
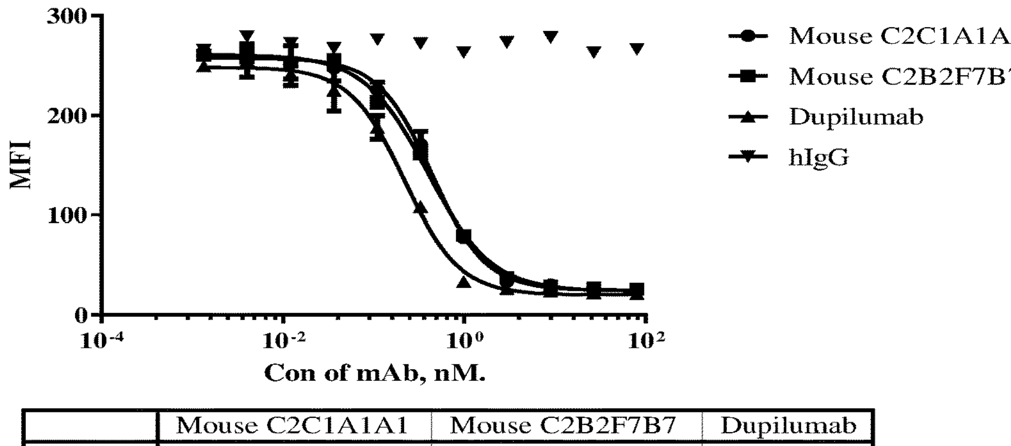

Further, as shown in Table 4 and FIG. 6A-6C that all anti-IL4Rα antibodies were able to block IL4 binding to cell surface IL4Rα, with very close blocking capacity to the benchmark despite of a bit higher $IC_{50}$ value.

TABLE 4

Anti-IL4Rα antibodies' blocking activity on benchmark-IL4Rα or IL4-IL4Rα binding

| | Competitive ELISA ($IC_{50}$, nM) | | Cell-based assay ($IC_{50}$, nM) |
|---|---|---|---|
| Mouse mAb | IL4-ILARα | IL4Rα-Benchmark | Cell-based ligand blocking FACS |
| B1D2F7D3B5 | 1.80 | 0.02 | 0.78 |
| B8G11F2B7G5E8 | 0.81 | 0.02 | 0.80 |
| B9D1D11F8D8 | 2.88 | 0.02 | 0.75 |
| C2C1A1A1 | 0.81 | 0.04 | 0.44 |
| C2B2F7B7 | 0.73 | 0.72 | 0.40 |
| Benchmark | 0.68 | 0.02 | 0.22 |

Example 5 Cell Based Functional Assay of Mouse Anti-IL4Rα Antibodies

IL4 and IL13 are capable of binding to IL4Rα and inducing phosphorylation of STAT6 in HEK293T-IL4Rα-STAT6-STAT6LUC-LB2 cells. The phosphorylation step is critical in IL4/IL13 signaling pathway.

The HEK293T-IL4Rα-STAT6-STAT6LUC-LB2 cells were prepared in house. Briefly, HEK293T cells (ATCC CRL-11268), naturally expressing IL13Rα1, were stably transfected with a pcDNA3.1-Puro (YouBio biological inc. Cat #VT9222) plasmid construct with nucleotide encoding human IL4Rα between BamHI and XhoI, a STAT6 plasmid (Sino biological inc. Cat #HG13190-NH) with nucleotide encoding human STAT6 between KpnI and XbaI, and a STAT6 Luciferase Reporter plasmid STAT6-Luc (Yeasen biological inc. Cat #11588ES03), and then a single cell clone LB2 was chosen for all subsequent functional assays.

The anti-IL4Rα antibodies of the disclosure were tested for the inhibitory effect on IL4 and IL13 induced STAT6 phosphorylation.

Briefly, HEK293T-IL4Rα-STAT6-STAT6LUC-LB2 cells at the log phase stage were seeded into 96-well plates in 100 μl medium (RPMI1640+10% FBS), $5\times10^5$ cells/well. Then, the plates were added with 50 μl serially diluted anti-IL4Rα antibodies or controls (including an in house made anti-CD22 antibody) (starting from 100 nM, 5-fold serial dilution), and incubated at 37° C. for 30 minutes. The plates were then added with 50 μl IL4 protein (600 μg/ml, Sino biological inc., Cat #11846-HNAE) or IL13 protein (50 ng/ml, Sino biological inc., Cat #10369-HNAC), and incubated at 37° C. for 20 minutes. The plates were centrifuged and washed two times using staining buffer (prepared in-house, DPBS+0.5% w/v BSA+2 mM EDTA), and then added with 50 μl/well fixation buffer (BD biosciences inc., Cat #5545655) and incubated for 30 minutes at 4° C. Cells were washed twice and incubated with permeabilization buffer (200 μl/well, BD biosciences inc., Cat #558050) for 30 minutes on ice. Plates were washed three times using staining buffer. The plates were then added with anti-pSTAT6 antibody (20-fold dilution of pSTAT6 stock solution, BD biosciences inc., Cat #562079) and left still for 60 minutes on ice. Plates were finally washed twice and resuspended in staining buffer. Fluorescence was measured using a Becton Dickinson FACS Canto II-HTS equipment. Data was analyzed using Graphpad Prism software and $IC_{50}$ values were reported.

Figure 7:
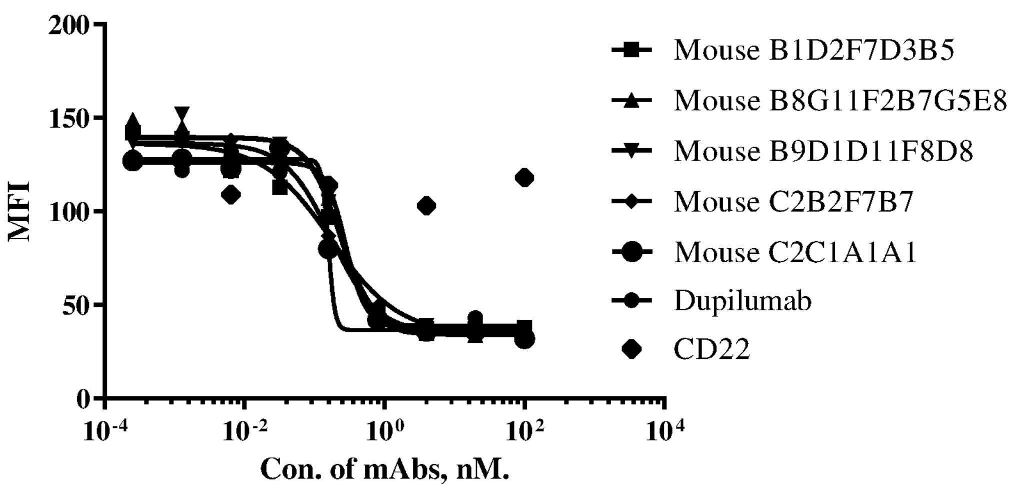
FIG. 7 shows the activity of mouse antibodies B1D2F7D3B5, B8G11F2B7G5E8, B9D1D11F8D8, C2C1A1A1 and C2B2F7B7 on inhibiting IL4-induced STAT6 phosphorylation in HEK293T-IL4Rα-STAT6-STAT6LUC-LB2 cells.
Figure 8:
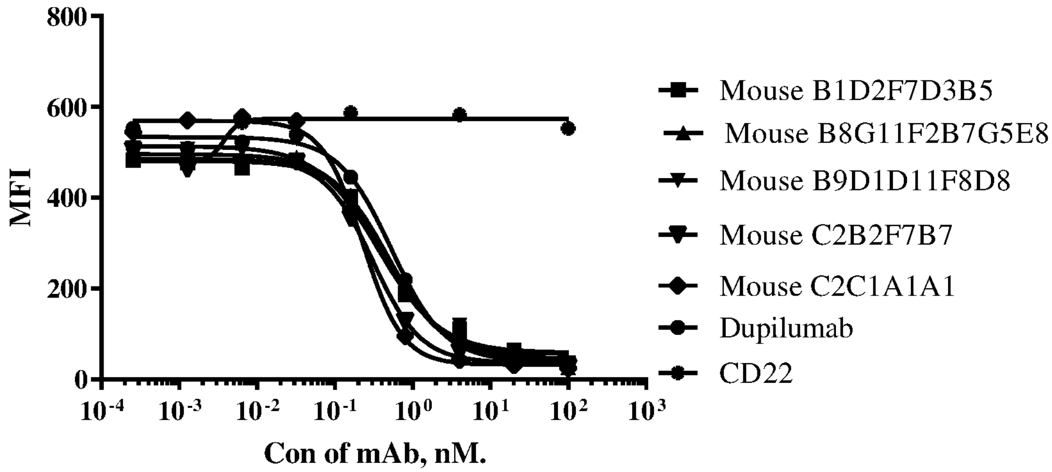
FIG. 8 shows the activity of mouse antibodies B1D2F7D3B5, B8G11F2B7G5E8, B9D1D11F8D8, C2C1A1A1 and C2B2F7B7 on inhibiting IL13-induced STAT6 phosphorylation in HEK293T-IL4Rα-STAT6-STAT6LUC-LB2 cells.
Figure 9:
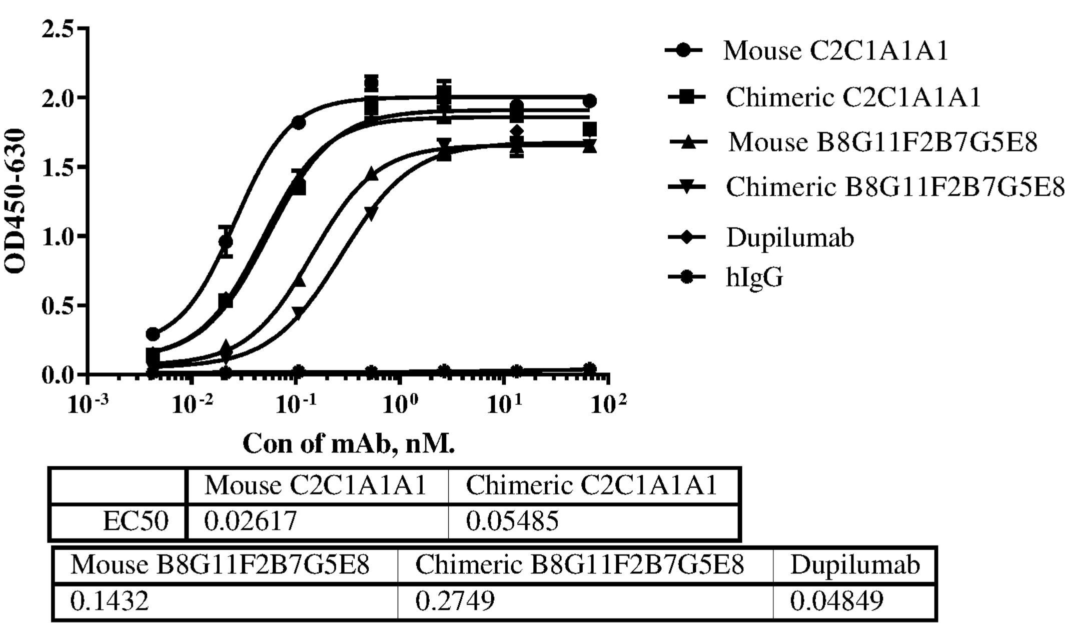
FIG. 9 shows the binding capacity of chimeric antibodies B8G11F2B7G5E8 and C2C1A1A1 to human IL4Rα.
Figure 10:
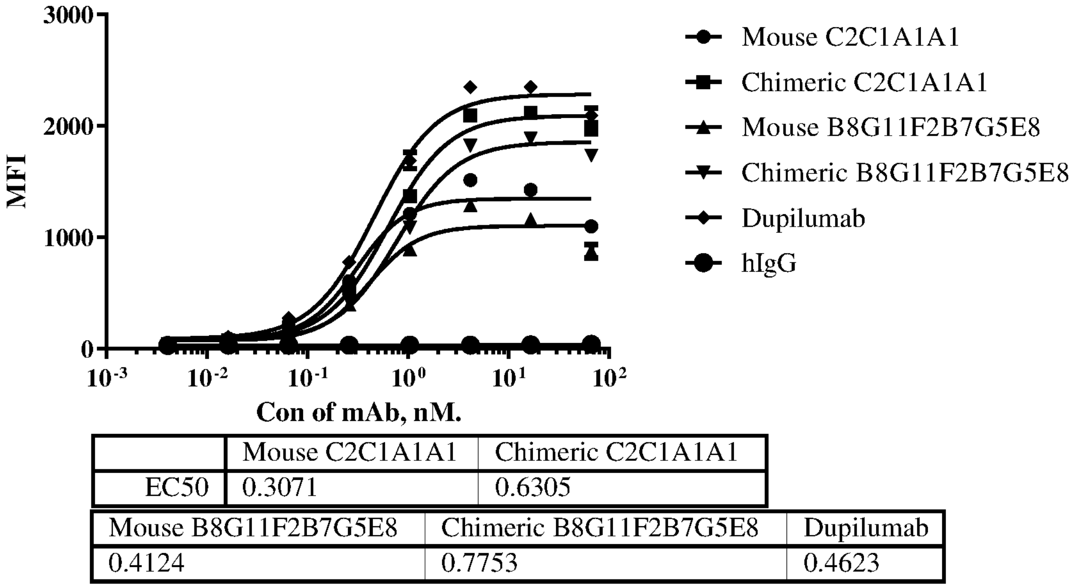
FIG. 10 shows the binding capacity of chimeric antibodies B8G11F2B7G5E8 and C2C1A1A1 to cell surface human IL4Rα.
Figure 11:
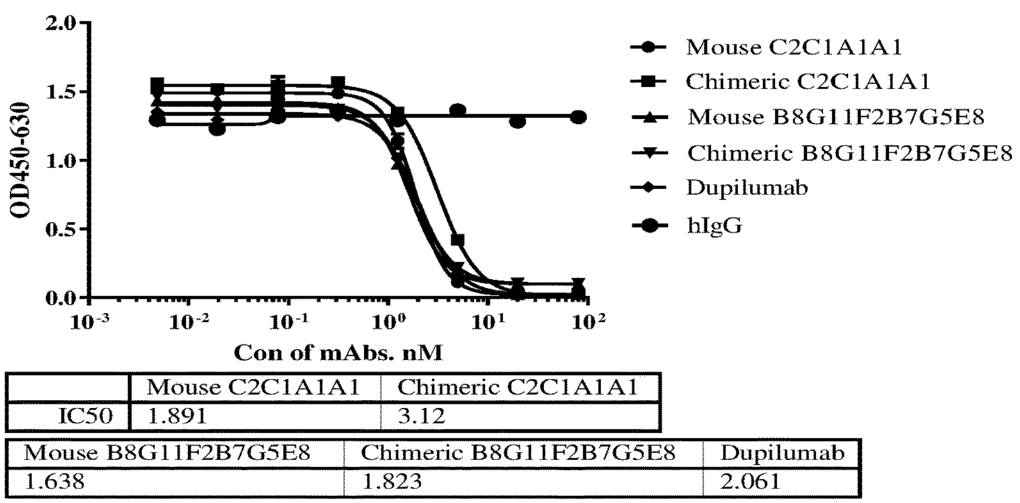
FIG. 11 shows the blocking ability of chimeric antibodies B8G11F2B7G5E8 and C2C1A1A1 on human IL4Rα-IL4 interaction.
Figure 12:
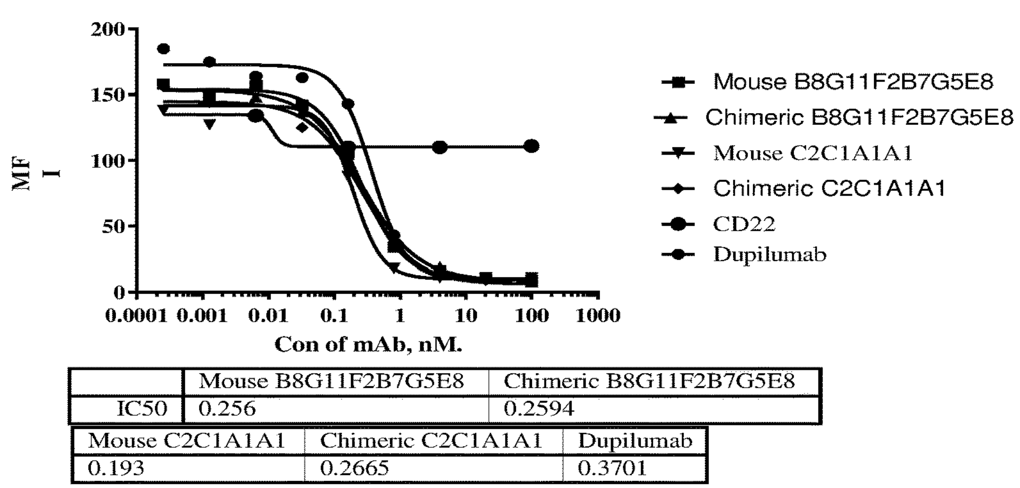
FIG. 12 shows the activity of chimeric antibodies B8G11F2B7G5E8 and C2C1A1A1 on inhibiting IL4-induced STAT6 phosphorylation in HEK293T-IL4Rα-STAT6-STAT6LUC-LB2 cells.
Figure 13:
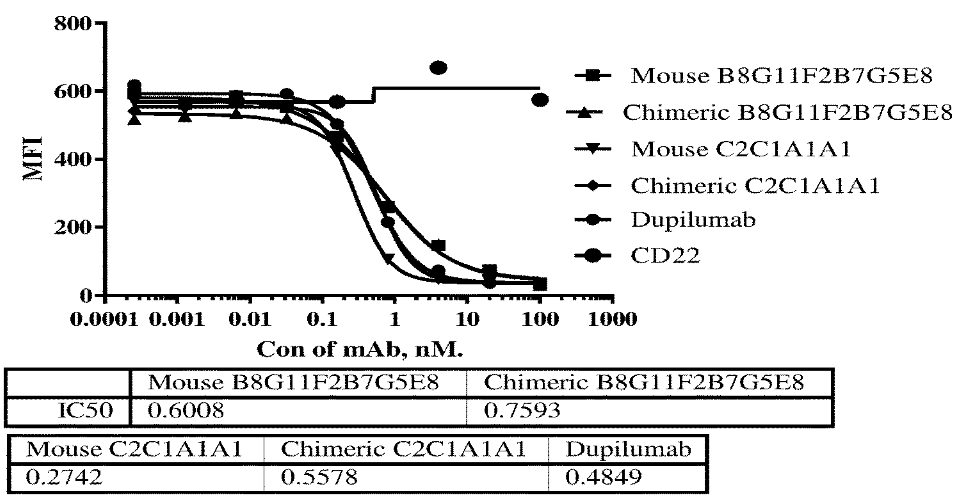
FIG. 13 shows the activity of chimeric antibodies B8G11F2B7G5E8 and C2C1A1A1 on inhibiting IL13-induced STAT6 phosphorylation in HEK293T-IL4Rα-STAT6-STAT6LUC-LB2 cells.

The results were shown in Table 5 below and FIGS. 7 and 8.

It can be seen that all anti-IL4Rα antibodies were able to block IL4 or IL13-induced STAT6 phosphorylation in HEK293T-IL4Rα-STAT6-STAT6LUC-LB2 cells, at comparable or higher blocking activity as compared to the benchmark.

TABLE 5

Anti-IL4Rα antibodies' functional assay results

| Mouse mAb ID# | Inhibition on IL4 induced STAT6 phosphorylation ($IC_{50}$, nM) | Inhibition on IL13 induced STAT6 phosphorylation ($IC_{50}$, nM) |
|---|---|---|
| B1D2F7D3B5 | 0.17 | 0.48 |
| B8G11F2B7G5E8 | 0.23 | 0.47 |
| B9D1D11F8D8 | 0.23 | 0.36 |
| C2C1A1A1 | 0.16 | 0.23 |
| C2B2F7B7 | 0.17 | 0.31 |
| Benchmark | 0.28 | 0.53 |

Example 6 Generation and Characterization of Chimeric Antibodies

The variable domains of the heavy and light chain of the anti-IL4Rα mouse mAbs were sequenced, and the sequence ID numbers were summarized in Table 1.

The variable domains of the heavy and light chain of the anti-IL4Rα mouse mAbs C2C1A1A1 and B8G11F2B7G5E8 were cloned in frame to human IgG4 heavy-chain (SEQ ID NO.: 55) and human kappa light-chain constant regions (SEQ ID NO.: 56), respectively, wherein the C terminus of variable region was linked to the N terminus of the respective constant region.

The vectors each containing a nucleotide encoding a heavy chain variable region linked to human IgG4 heavy-chain constant region, and the vectors each containing a nucleotide encoding a light chain variable region linked to human kappa light-chain constant region were transiently transfected into 50 ml of 293F suspension cell cultures in a ratio of 60% to 40% light to heavy chain construct, with 1 mg/mL PEI.

Cell supernatants were harvested after six days in shaking flasks, spun down to pellet cells, and filtered through 0.22 μm filters for immunoglobulin separation. The chimeric antibodies were purified by protein A affinity chromatography. Briefly, Protein A sepharose column (from bestchrom (Shanghai) Biosciences, Cat #AA0273) was washed 5 to 10 column volumes using PBS buffer. Cell supernatants were passed through the columns, and then the columns were washed using PBS buffer until the absorbance for protein reached the baseline. The columns were eluted with elution buffer (0.1 M Glycine-HCl, pH 2.7), and immediately collected into 1.5 ml tubes with neutralizing buffer (1 M Tris-HCl, pH 9.0). Fractions containing immunoglobulins were pooled and dialyzed in PBS overnight at 4° C.

The purified antibodies were tested in the capture ELISA, competitive ELISA, BIAcore affinity test, cell based binding FACS and cell-based functional assay following the protocols in the foregoing Examples with minor modifications described below.

For the capture ELISA, 96-well micro plates were coated with 2 μg/ml goat anti-human IgG (AffiniPure Goat Anti-Human IgG, Fcγ fragment specific, Jackson Immunoresearch, Cat #109-005-098) instead of goat anti-mouse IgG Fcγ fragment, 100 μl/well.

For the Indirect ELISA, Peroxidase AffiniPure $F(ab')_2$ Fragment Goat Anti-Human IgG, Fcγ Fragment Specific (Jackson Immunoresearch, Cat #109-036-098) was used instead of Peroxidase AffiniPure Goat Anti-Mouse IgG, Fcγ Fragment Specific, 100 μl/well.

For the BIAcore, goat anti-human IgG (GE healthcare, Cat #BR100839, Human Antibody Capture Kit) was covalently linked to a CM5 chip instead of goat anti-mouse IgG.

For the cell-based binding FACS, R-Phycoerythrin AffiniPure Goat Anti-human IgG Fcγ fragment specific (Jackson Immunoresearch, Cat #109-115-098) was used instead of R-Phycoerythrin AffiniPure $F(ab')_2$ Fragment Goat Anti-Mouse IgG (H+L), 1:1000 dilution in FACS buffer, 100 μl/well.

The results were shown in Table 6 and FIG. 9-13. The data showed that the chimeric antibodies had similar binding affinity/capacity and blocking activity to their parental mouse antibodies.

TABLE 6

Binding and functional activities of Chimeric Antibodies

| mAb ID# | Capture ELISA to human IL4R ($EC_{50}$, nM) | BIAcore Affinity to human IL4R ($K_D$, M) | Cell-based binding FACS ($EC_{50}$, nM) | IL4-IL4Rα blocking ELISA ($IC_{50}$, nM) | Cell-based functional assay: Inhibition on IL4 induced STAT6 phosphorylation ($IC_{50}$, nM) | Cell-based functional assay: Inhibition on IL13 induced STAT6 phosphorylation ($IC_{50}$, nM) |
|---|---|---|---|---|---|---|
| Mouse B8G11F2B7G5E8 | 0.14 | 2.976E−9 | 0.41 | 1.64 | 0.26 | 0.60 |
| Chimeric B8G11F2B7G5E8 | 0.27 | 2.987E−9 | 0.78 | 1.82 | 0.26 | 0.76 |
| Mouse C2C1A1A1 | 0.03 | 1.195E−10 | 0.31 | 1.89 | 0.19 | 0.27 |
| Chimeric C2C1A1A1 | 0.05 | 5.219E−10 | 0.63 | 3.12 | 0.27 | 0.56 |
| Benchmark | 0.05 | 4.656E−10 | 0.46 | 2.06 | 0.37 | 0.48 |

Example 7 Humanization of Anti-IL4Rα Monoclonal Antibodies B8G11F2B7G5E8 and C2C1A1A1

Mouse anti-IL4Rα antibodies B8G11F2B7G5E8 and C2C1A1A1 were humanized and further characterized. Humanization of the mouse antibodies were conducted using the well-established CDR-grafting method as described in detail below.

To select acceptor frameworks for humanization of mouse antibodies B8G11F2B7G5E8 and C2C1A1A1, the light and heavy chain variable region sequences of each mouse antibody were blasted against the human immunoglobulin gene database. The human germlines with the highest homology were selected as the acceptor frameworks for humanization. The mouse antibody heavy/light chain variable region CDRs were inserted into the selected frameworks, and the residue (s) in the frameworks was/were further backmutated to obtain more candidate heavy chain/light chain variable regions. A total of 13 exemplary humanized B8G11F2B7G5E8 antibodies, namely huB8G11F2B7G5E8-V1 to huB8G11F2B7G5E8-V11, huB8G11F2B7G5E8-V13 and huB8G11F2B7G5E8-V14, and 16 exemplary humanized C2C1A1A1 antibodies, namely huC2C1A1A1-V1 to huC2C1A1A1-V16, were obtained whose heavy/light chain variable region sequence ID numbers were in Table 1.

The vectors each containing a nucleotide encoding a humanized heavy chain variable region linked to human IgG4 heavy-chain constant region (SEQ ID NO: 55), and the vectors each containing a nucleotide encoding a humanized light chain variable region linked to human kappa light-chain constant region (SEQ ID NO: 56) were transiently transfected into 50 ml of 293F suspension cell cultures in a ratio of 60% to 40% light to heavy chain construct, with 1 mg/mL PEI.

Cell supernatants were harvested after six days in shaking flasks, spun down to pellet cells, and filtered through 0.22 μm filters for immunoglobulin separation. The antibodies were purified by protein A affinity chromatography. Briefly, Protein A sepharose column (from bestchrom (Shanghai) Biosciences, Cat #AA0273) was washed 5 to 10 column volumes using PBS buffer. Cell supernatants were passed through the columns, and then the columns were washed using PBS buffer until the absorbance for protein reached the baseline. The columns were eluted with elution buffer (0.1 M Glycine-HCl, pH 2.7), and immediately collected into 1.5 ml tubes with neutralizing buffer (1 M Tris-HCl, pH 9.0). Fractions containing immunoglobulins were pooled and dialyzed in PBS overnight at 4° C.

Example 8 Characterization of Humanized Antibodies

TABLE 7

Binding Affinity of Humanized B8G11F2B7G5E8 mAbs

| | Kinetics on BIAcore Human IL4Rα | | |
|---|---|---|---|
| mAb | $K_a$ (1/Ms) | $K_d$ (s−1) | $K_D$ (M) |
| Chimeric B8G11F2B7G5E8 | 5.29E+05 | 0.001426 | 2.69E−09 |
| huB8G11F2B7G5E8-V1 | 5.57E+05 | 0.002079 | 3.73E−09 |

TABLE 7-continued

Binding Affinity of Humanized B8G11F2B7G5E8 mAbs

| | Kinetics on BIAcore Human IL4Rα | | |
|---|---|---|---|
| mAb | $K_a$ (1/Ms) | $K_d$ (s−1) | $K_D$ (M) |
| huB8G11F2B7G5E8-V2 | 5.21E+05 | 0.001616 | 3.10E−09 |
| huB8G11F2B7G5E8-V3 | 5.58E+05 | 0.001991 | 3.57E−09 |
| huB8G11F2B7G5E8-V4 | 5.77E+05 | 0.001851 | 3.21E−09 |
| huB8G11F2B7G5E8-V5 | 5.84E+05 | 0.002414 | 4.13E−09 |
| huB8G11F2B7G5E8-V6 | 5.54E+05 | 0.002188 | 3.95E−09 |
| huB8G11F2B7G5E8-V7 | 5.92E+05 | 0.002219 | 3.75E−09 |
| huB8G11F2B7G5E8-V8 | 5.78E+05 | 0.002827 | 4.89E−09 |
| huB8G11F2B7G5E8-V9 | 6.21E+05 | 0.003305 | 5.32E−09 |
| huB8G11F2B7G5E8-V10 | 5.85E+05 | 0.002803 | 4.79E−09 |
| huB8G11F2B7G5E8-V11 | 1.65E+09 | 24.57 | 1.49E−08 |
| Benchmark | 7.42E+05 | 3.30E−04 | 4.44E−10 |
| Chimeric B8G11F2B7G5E8 | 3.06E+05 | 0.001124 | 3.68E−09 |
| huB8G11F2B7G5E8-V13 | 3.10E+05 | 0.0012 | 3.87E−09 |
| huB8G11F2B7G5E8-V14 | 3.06E+05 | 0.001129 | 3.69E−09 |

The binding affinity of the humanized antibodies to human IL4Rα were assessed by BIAcore technology following the protocols in the foregoing Examples. The $K_a$, $K_d$ and $K_D$ values were determined and summarized in Table 7 and 8.

TABLE 8

Binding Affinity of Humanized C2C1A1A1 mAbs

| | Kinetics on BIAcore Human IL4Rα | | | | | |
|---|---|---|---|---|---|---|
| mAb | Ka (1/Ms) | Kd (1/s) | $K_D$ (M) | Start (RU) | End (RU) | Dissociation % |
| Chimeric C2C1A1A1 | 3.29E+05 | <1.00E−05 | <3.04E−11 | 67.1 | 65.8 | −1.94% |
| Chimeric C2C1A1A1-containing supernatant | 3.64E+05 | 4.04E−05 | 1.11E−10 | 40 | 40.4 | 1.00% |
| huC2C1A1A1-V1 | 1.29E+05 | <1.00E−05 | <7.73E−11 | 43.9 | 44 | 0.23% |
| huC2C1A1A1-V2 | 2.26E+05 | <1.00E−05 | <4.42E−11 | 50.4 | 50.3 | −0.20% |
| huC2C1A1A1-V3 | 2.57E+05 | <1.00E−05 | <3.89E−11 | 48.6 | 48.3 | −0.62% |
| huC2C1A1A1-V4 | 4.55E+05 | <1.00E−05 | <2.20E−11 | 49.5 | 49.6 | 0.20% |
| huC2C1A1A1-V5 | 2.65E+06 | 7.50E−05 | 2.83E−11 | 65.8 | 64.3 | −2.28% |
| huC2C1A1A1-V6 | 3.83E+05 | <1.00E−05 | <2.61E−11 | 50.9 | 50.6 | −0.59% |
| huC2C1A1A1-V7 | 2.63E+05 | <1.00E−05 | <3.80E−11 | 60.5 | 60.1 | −0.66% |
| huC2C1A1A1-V8 | 2.78E+05 | <1.00E−05 | <3.60E−11 | 65.2 | 64.4 | −1.23% |
| huC2C1A1A1-V9 | 1.97E+05 | <1.00E−05 | <5.07E−11 | 41.2 | 41.1 | −0.24% |
| huC2C1A1A1-V10 | 3.29E+05 | <1.00E−05 | <3.04E−11 | 64.9 | 63.9 | −1.54% |
| huC2C1A1A1-V11 | 3.30E+05 | <1.00E−05 | <3.03E−11 | 54.2 | 53.7 | −0.92% |
| huC2C1A1A1-V12 | 3.02E+05 | 1.42E−05 | 4.70E−11 | 53.1 | 52.1 | −1.88% |
| huC2C1A1A1-V13 | 1.193E+05 | <1.00E−05 | <8.38E−11 | 36.4 | 36.7 | 0.82% |
| huC2C1A1A1-V14 | 1.53E+05 | <1.00E−05 | <6.54E−11 | 50.1 | 50.5 | 0.80% |
| huC2C1A1A1-V15 | 2.30E+05 | <1.00E−05 | <4.35E−11 | 69 | 69.2 | 0.29% |
| huC2C1A1A1-V16 | 2.96E+05 | <1.00E−05 | <3.38E−11 | 47.3 | 47.1 | −0.42% |
| Benchmark | 3.33E+05 | 6.25E−05 | 1.88E−10 | 71.9 | 70 | −2.64% |

Dissociation % = (End (RU) − Start (RU))/Start (RU)

The data indicated that the humanized antibodies had similar human IL4Rα binding affinity to the chimeric antibody, and all the humanized huC2C1A1A1 antibodies showed higher human IL4Rα binding affinity than the benchmark.

The humanized antibodies huB8G11F2B7G5E8-V2, huB8G11F2B7G5E8-V4, huB8G11F2B7G5E8-V14, huC2C1A1A1-V14 and huC2C1A1A1-V15 were further tested in Biacore, capature ELISA, indirect ELISA, cell-based binding FACS, competitive ELISA and cell-based functional assay, following the protocols in the foregoing Examples with minor modifications described below.

For the capture ELISA, 96-well micro plates were coated with 2 μg/ml goat anti-human IgG (AffiniPure Goat Anti-Human IgG, Fcγ fragment specific, Jackson Immunoresearch, Cat #109-005-098) instead of goat anti-mouse IgG Fcγ fragment, 100 μl/well.

For the Indirect ELISA, Peroxidase AffiniPure F(ab')$_2$ Fragment Goat Anti-Human IgG, Fcγ Fragment Specific (Jackson Immunoresearch, Cat #109-036-098) was used instead of Peroxidase AffiniPure Goat Anti-Mouse IgG, Fcγ Fragment Specific, 100 μl/well.

For the BIAcore, goat anti-human IgG (GE healthcare, Cat #BR100838, Human Antibody Capture Kit) was covalently linked to a CM5 chip instead of goat anti-mouse IgG.

For the cell-based binding FACS, R-Phycoerythrin AffiniPure Goat Anti-human IgG Fcγ fragment specific (Jackson Immunoresearch, Cat #109-115-098) was used instead of R-Phycoerythrin AffiniPure F(ab')$_2$ Fragment Goat Anti-Mouse IgG (H+L), 1:1000 dilution in FACS buffer, 100 μl/well.

The humanized antibodies huB8G11F2B7G5E8-V14 and huC2C1A1A1-V15 were also tested for the thermal stability. Briefly, a protein thermal shift assay was used to determine Tm (melting temperature) using a GloMelt™ Thermal Shift Protein Stability Kit (Biotium, Cat #33022-T, lot #: 181214). Briefly, the GloMelt™ dye was allowed to thaw and reach room temperature. The vial containing the dye was vortexed and centrifuged. Then, 10× dye was prepared by adding 5 μL 200× dye to 95 μL PBS. 2 μL 10× dye and 10 μg humanized antibodies were added, and PBS was added to a total reaction volume of 20 μL. The tubes containing the dye and antibodies were briefly spun and placed in real-time PCR thermocycler (Roche, LightCycler 480 II) set up with a melt curve program having the parameters in Table 9.

TABLE 9

Parameters for Melt Curve Program

| Profile step | Temperature | Ramp rate | Holding Time |
|---|---|---|---|
| Initial hold | 25° C. | NA | 30 s |
| Melt curve | 25-99° C. | 0.1° C./s | NA |

Figure 14A:
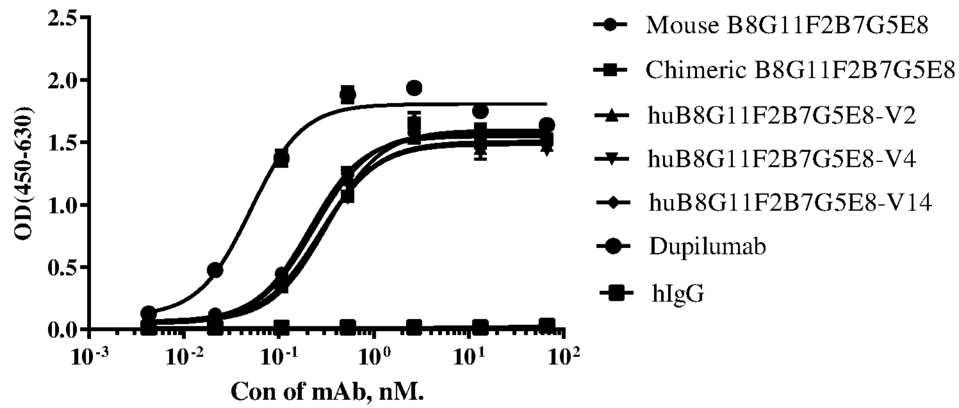
FIGS. 14A-14B show the binding capacity of humanized antibodies huB8G11F2B7G5E8-V2, huB8G11F2B7G5E8-V4 and huB8G11F2B7G5E8-V14 (A), huC2C1A1A1-V14 and huC2C1A1A1-V15 (B) to human IL4Rα.
Figure 14B:
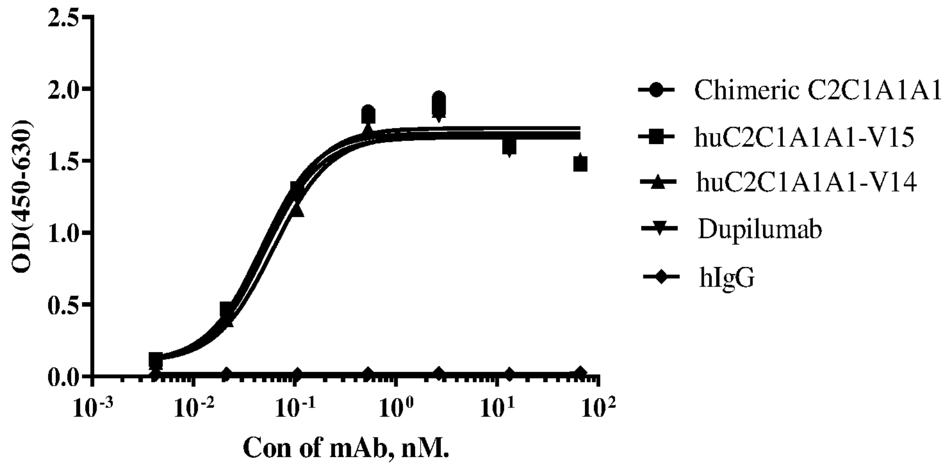
Figure 15A:
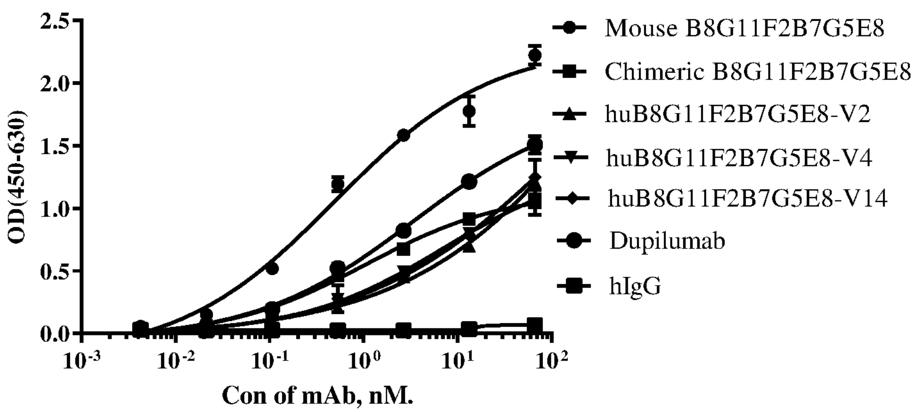
FIGS. 15A-15B show the binding capacity of humanized antibodies huB8G11F2B7G5E8-V2, huB8G11F2B7G5E8-V4 and huB8G11F2B7G5E8-V14 (A), huC2C1A1A1-V14 and huC2C1A1A1-V15 (B) to cynomolgus IL4Rα.
Figure 15B:
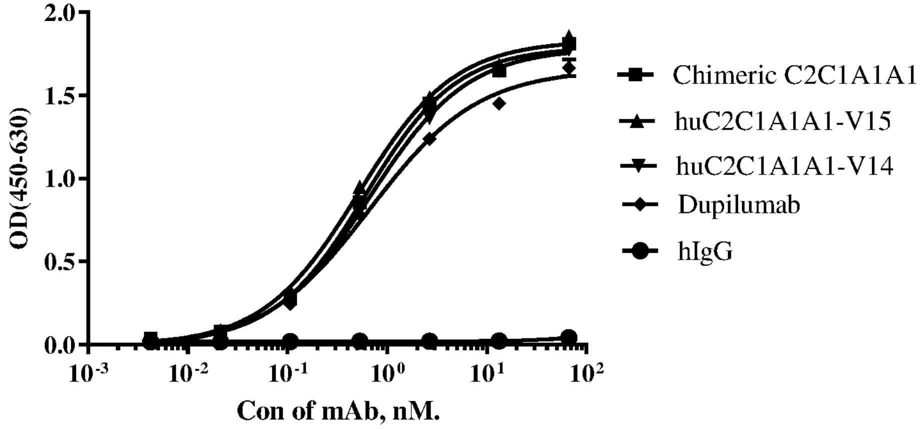
Figure 16A:
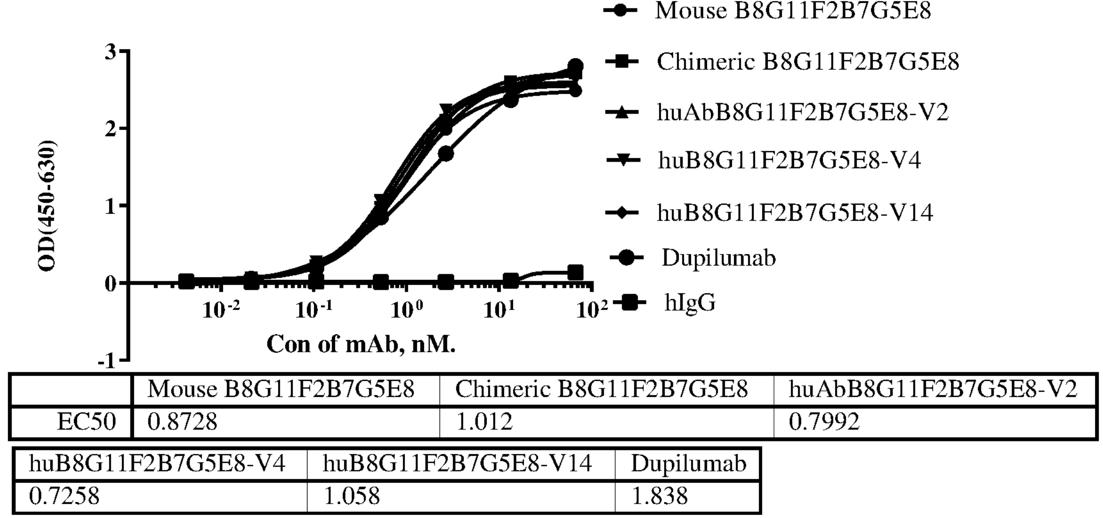
FIGS. 16A-16B show the binding capacity of humanized antibodies huB8G11F2B7G5E8-V2, huB8G11F2B7G5E8-V4 and huB8G11F2B7G5E8-V14 (A), huC2C1A1A1-V14 and huC2C1A1A1-V15 (B) to cal-IL4Rα.
Figure 16B:
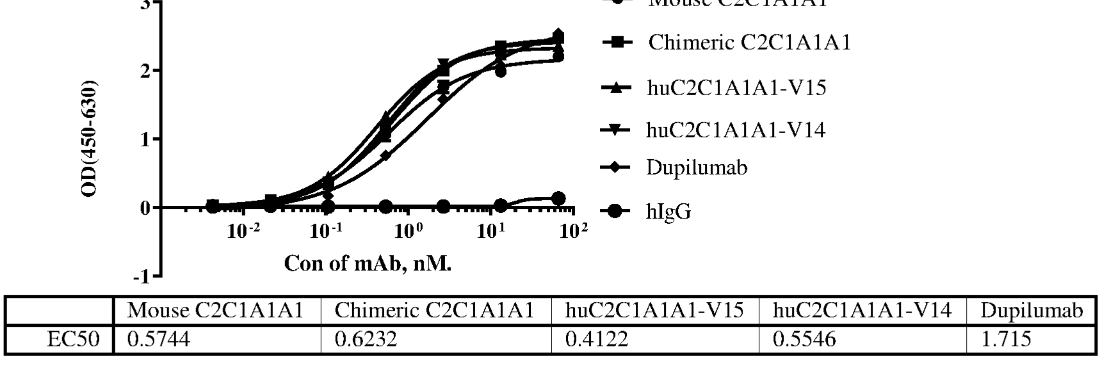
Figure 17A:
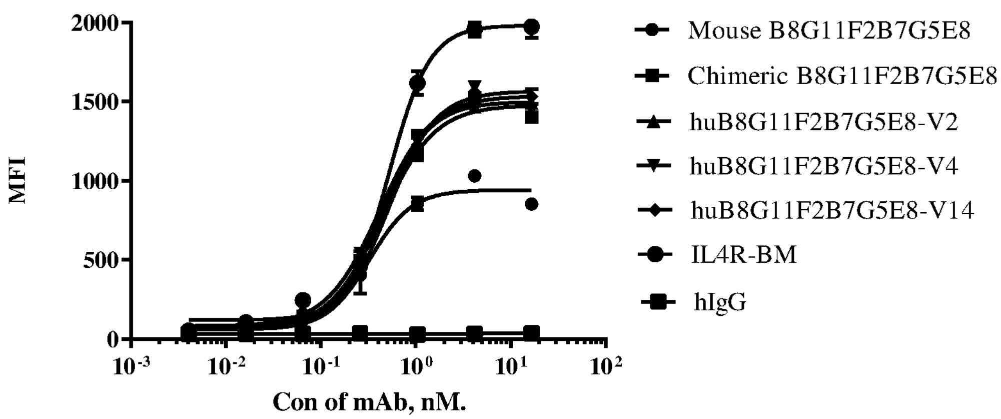
FIGS. 17A-17B show the binding capacity of humanized antibodies huB8G11F2B7G5E8-V2, huB8G11F2B7G5E8-V4 and huB8G11F2B7G5E8-V14 (A), huC2C1A1A1-V14 and huC2C1A1A1-V15 (B) to cell surface human IL4Rα.
Figure 17B:
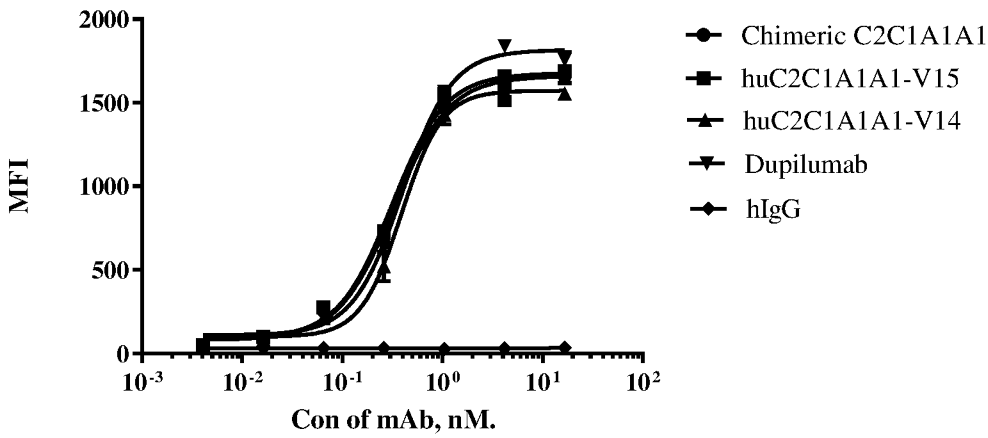
Figure 18A:
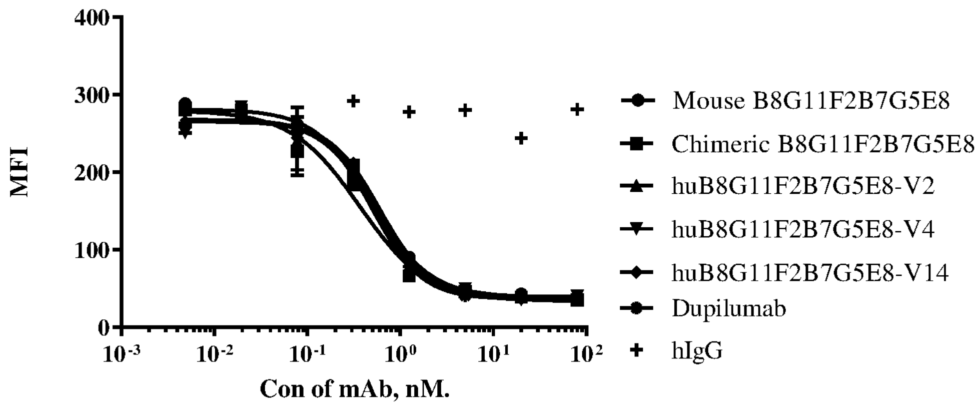
FIGS. 18A-18B show the blocking ability of humanized antibodies huB8G11F2B7G5E8-V2, huB8G11F2B7G5E8-V4 and huB8G11F2B7G5E8-V14 (A), huC2C1A1A1-V14 and huC2C1A1A1-V15 (B) on interaction of human IL4 with 293F cells expressing human IL4Rα.
Figure 18B:
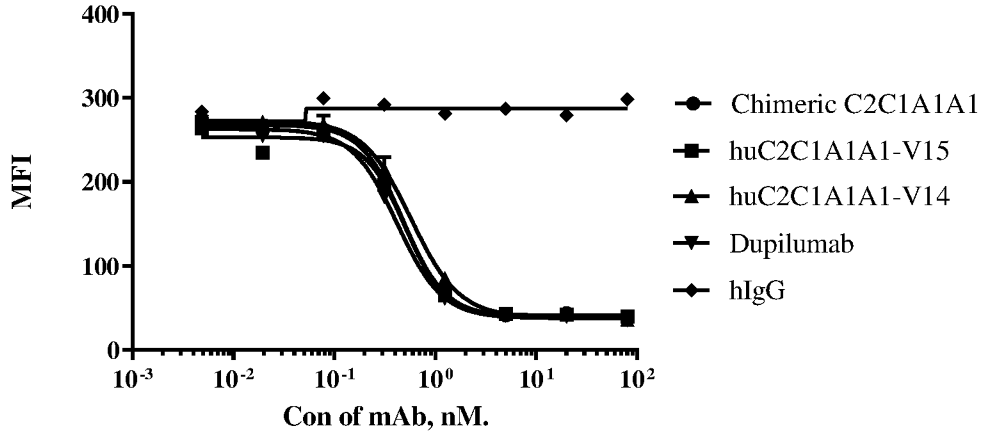
Figure 19A:
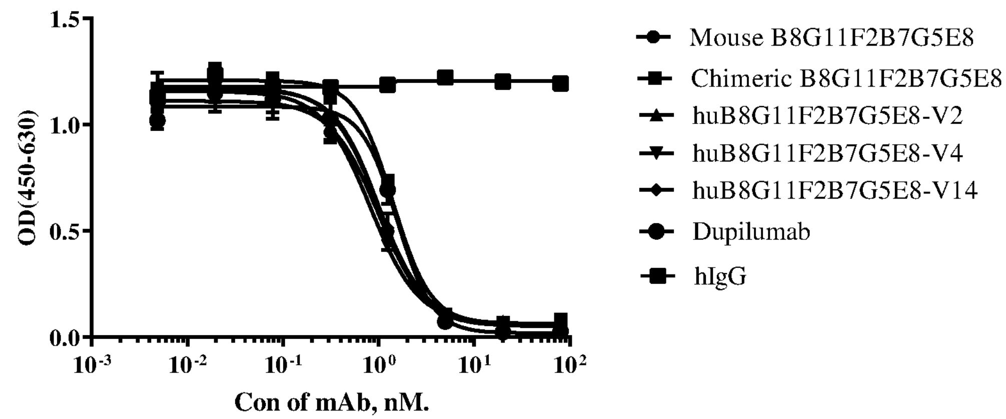
FIGS. 19A-19B show the blocking ability of humanized antibodies huB8G11F2B7G5E8-V2, huB8G11F2B7G5E8-V4 and huB8G11F2B7G5E8-V14 (A), huC2C1A1A1-V14 and huC2C1A1A1-V15 (B) on human IL4Rα-IL4 interaction.
Figure 19B:
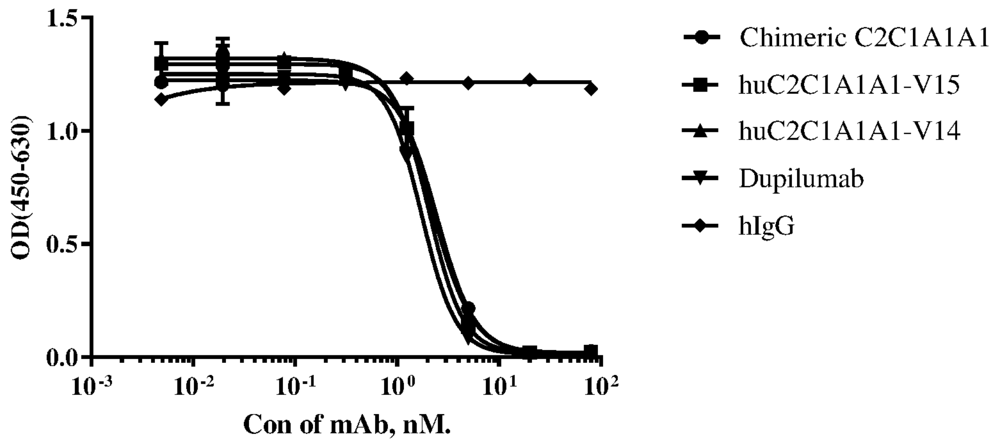
Figure 20A:
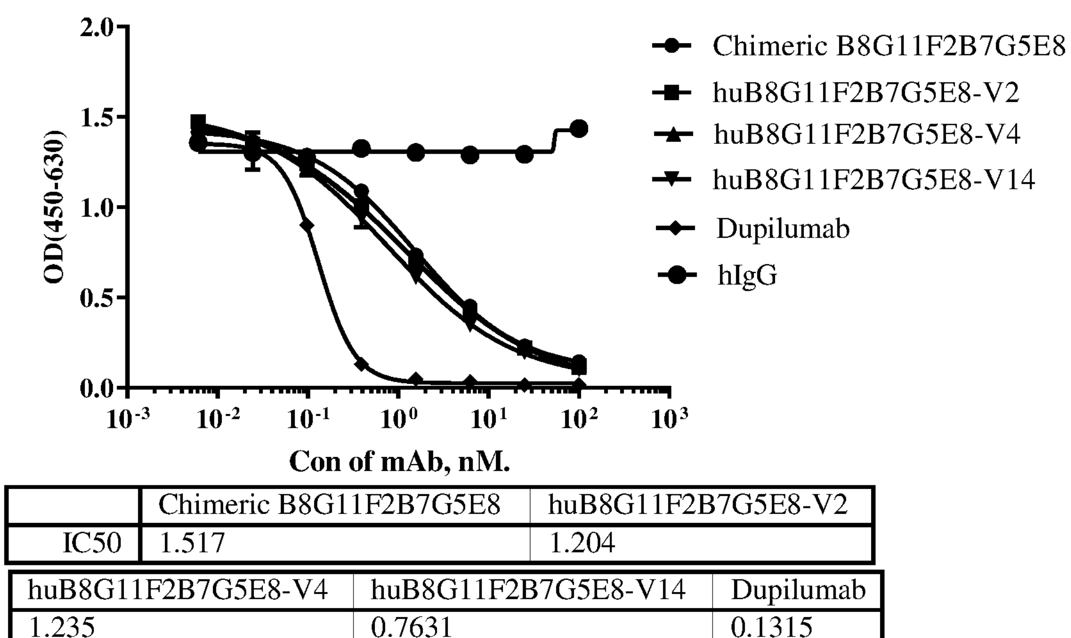
FIGS. 20A-20B show the ability of humanized antibodies huB8G11F2B7G5E8-V2, huB8G11F2B7G5E8-V4 and huB8G11F2B7G5E8-V14 (A), huC2C1A1A1-V14 and huC2C1A1A1-V15 (B) to block Benchmark-human IL4Rα binding.
Figure 20B:
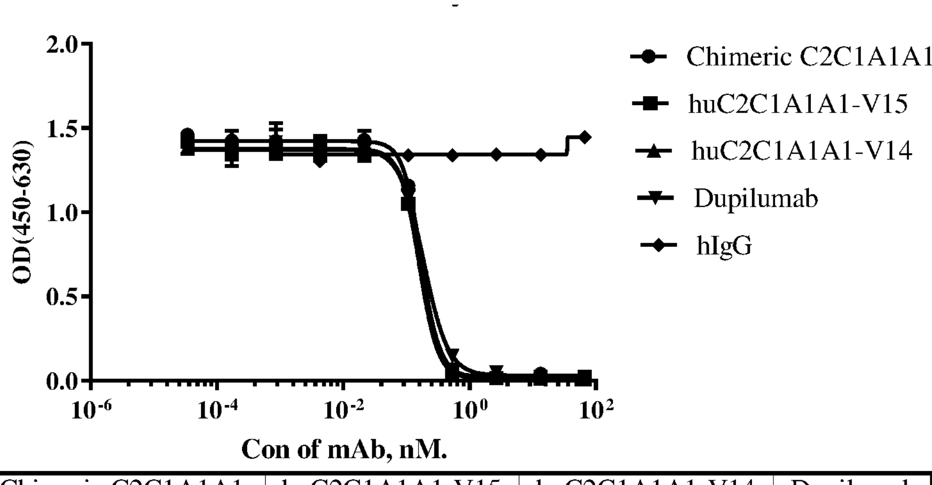
Figure 21:
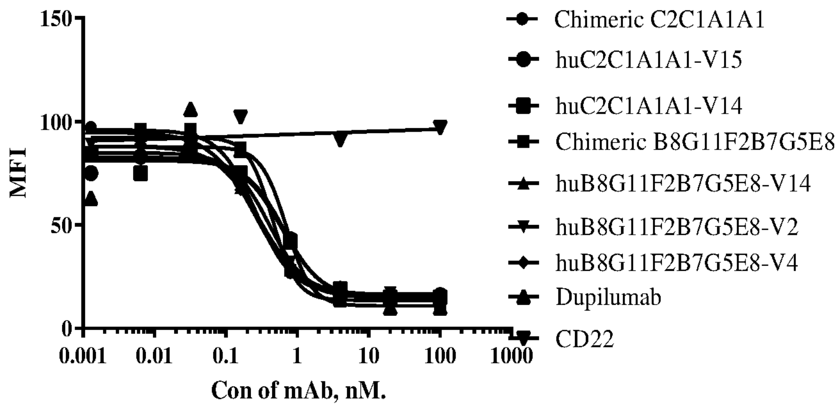
FIG. 21 shows the activity of humanized antibodies huB8G11F2B7G5E8-V2, huB8G11F2B7G5E8-V4 and huB8G11F2B7G5E8-V14 (A), huC2C1A1A1-V14 and huC2C1A1A1-V15 (B) on inhibiting IL4-induced STAT6 phosphorylation in HEK293T-IL4Rα-STAT6-STAT6LUC-LB2 cells.
Figure 22:
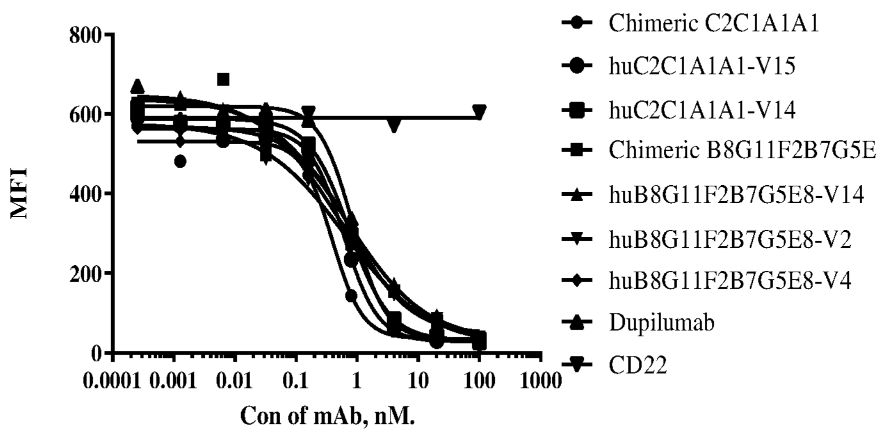
FIG. 22 shows the activity of humanized antibodies huB8G11F2B7G5E8-V2, huB8G11F2B7G5E8-V4 and huB8G11F2B7G5E8-V14 (A), huC2C1A1A1-V14 and huC2C1A1A1-V15 (B) on inhibiting IL13-induced STAT6 phosphorylation in HEK293T-IL4Rα-STAT6-STAT6LUC-LB2 cells.

The results were shown in Table $10^{-1}$ to $10^{-3}$ and FIGS. 14A-14B to 22.

TABLE 10-1

Binding and Functional activity of Humanized mAbs

| | Binding assay Human IL4Rα-his | | | Cyno-IL4Rα-his | |
|---|---|---|---|---|---|
| mAb ID# | Capture ELISA ($EC_{50}$, nM) | Biacore ($K_D$, M) | Cell Binding FACS ($EC_{50}$, nM) | Biacore ($K_D$, M) | Indirect ELISA ($EC_{50}$, nM) |
| chimeric C2C1A1A1 | 0.05 | 3.88E−10 | 0.33 | Weak | 0.60 |
| huC2C1A1A1-V15 | 0.05 | 4.47E−10 | 0.31 | Weak | 0.52 |
| huC2C1A1A1-V14 | 0.06 | 6.42E−10 | 0.39 | Weak | 0.68 |
| Benchmark | 0.05 | 7.46E−10 | 0.40 | No binding | 0.67 |
| mouse B8G11F2B7G5E8 | 0.21 | * | 0.33 | * | 0.50 |
| Chimeric B8G11F2B7G5E8 | 0.32 | 3.23E−09 | 0.44 | Weak | 1.06 |
| huB8G11F2B7G5E8-V14 | 0.24 | 3.88E−09 | 0.52 | Weak | 137.4 |
| huB8G11F2B7G5E8-V2 | 0.27 | 4.10E−09 | 0.43 | Weak | 914.1 |
| huB8G11F2B7G5E8-V4 | 0.27 | 5.50E−09 | 0.41 | Weak | 7.12 |
| Benchmark | 0.05 | 7.46E−10 | 0.53 | No binding | 3.34 |

*Not tested yet.

TABLE 10-2

Binding and Functional activity of Humanized mAbs

| | Binding assay Cal-IL4Rα-his | | Competitive ELISA IL4-IL4Rα | Competitive ELISA Benchmark | IL4-IL4Rα |
|---|---|---|---|---|---|
| mAb ID# | Biacore ($K_D$, M) | Indirect ELISA ($EC_{50}$, nM) | blocking ELISA ($IC_{50}$, nM) | blocking ELISA ($IC_{50}$, nM) | blocking FACS ($IC_{50}$, nM) |
| Chimeric C2C1A1A1 | Weak | 0.62 | 2.46 | 0.17 | 0.48 |
| huC2C1A1A1-V15 | Weak | 0.41 | 2.03 | 0.16 | 0.50 |
| huC2C1A1A1-V14 | Weak | 0.55 | 2.17 | 0.17 | 0.58 |
| Benchmark | No binding | 1.72 | 1.74 | 0.19 | 0.42 |
| Mouse B8G11F2B7G5E8 | * | 0.87 | 1.00 | * | 0.50 |
| Chimeric B8G11F2B7G5E8 | Weak | 1.01 | 1.42 | 1.52 | 0.36 |
| huB8G11F2B7G5E8-V14 | Weak | 1.06 | 1.02 | 0.76 | 0.60 |
| huB8G11F2B7G5E8-V2 | Weak | 0.80 | 1.00 | 1.20 | 0.54 |

TABLE 10-2-continued

Binding and Functional activity of Humanized mAbs

| mAb ID# | Binding assay Cal-IL4Rα-his Biacore ($K_D$, M) | Indirect ELISA ($EC_{50}$, nM) | Competitive ELISA IL4-IL4Rα blocking ELISA ($IC_{50}$, nM) | Benchmark blocking ELISA ($IC_{50}$, nM) | IL4-IL4Rα blocking FACS ($IC_{50}$, nM) |
|---|---|---|---|---|---|
| huB8G11F2B7G5E8-V4 | Weak | 0.73 | 0.82 | 1.24 | 0.51 |
| Benchmark | No binding | 1.84 | 1.56 | 0.13 | 0.51 |

* Not tested yet.

TABLE 10-3

Binding and Functional activity of Humanized mAbs

| mAb ID# | Cell-based functional assay ($IC_{50}$, nM) Inhibition on IL4 induced STAT6 phosphorylation | Inhibition on IL13 induced STAT6 phosphorylation | Tm (melting temperature) ° C. Tm1 | Tm2 |
|---|---|---|---|---|
| chC2C1A1A1 | 0.26 | 0.39 | * | * |
| huC2C1A1A1-V15 | 0.61 | 0.60 | NA | 72.0 |
| huC2C1A1A1-V14 | 0.64 | 0.73 | 65.5 | 74.0 |
| Benchmark | 0.70 | 0.84 | * | * |
| mAb B8G11F2B7G5E8 | * | * | * | * |
| chB8G11F2B7G5E8 | 0.45 | 0.50 | * | * |
| huB8G11F2B7G5E8-V14 | 0.26 | 0.66 | 65.5 | 80.5 |
| huB8G11F2B7G5E8-V2 | 0.40 | 0.63 | 65.0 | 80.0 |
| huB8G11F2B7G5E8-V4 | 0.30 | 0.81 | 65.0 | 80.0 |
| Benchmark | 0.70 | 0.84 | * | * |

*Not tested yet.

According to the data, the humanized C2C1A1A1 antibodies showed comparable, if not better, binding affinity/activity to human IL4Rα and IL4Rα-IL4/IL13 blocking capacity when compared to the benchmark. While the humanized B8G11F2B7G5E8 antibodies obviously had better blocking capacity on IL4/IL13-IL13Rα1-IL4Rα interaction.

While the disclosure has been described above in connection with one or more embodiments, it should be understood that the disclosure is not limited to those embodiments, and the description is intended to cover all alternatives, modifications, and equivalents, as may be included within the spirit and scope of the appended claims. All referenced cited herein are further incorporated by reference in their entirety.

The invention claimed is:

1. An isolated monoclonal antibody or an antigen-binding portion thereof, binding to interleukin 4 receptor subunit alpha (IL4Rα), comprising a heavy chain variable region and a light chain variable region each comprising a CDR1 region, a CDR2 region and a CDR3 region, wherein the heavy chain variable region CDR1, CDR2 and CDR3, and the light chain variable region CDR1, CDR2 and CDR3 comprise amino acid sequences of SEQ ID NOs: 1, 5, 10, 15, 22 and 26, respectively.

2. The isolated monoclonal antibody or the antigen-binding portion thereof of claim 1, wherein the heavy chain variable region comprises an amino acid sequence having at least 85%, 86%, 87%, 88%, 89%, 90%, 91%, 92%, 93%, 94%, 95%, 96%, 97%, 98%, 99% or 100% identity to SEQ ID NOs: 32, 33 (X1=W, X2=S; X1=L, X2=A; or X1=W, X2=A), or 34.

3. The isolated monoclonal antibody or the antigen-binding portion thereof of claim 1, wherein the light chain variable region comprises an amino acid sequence having at least 85%, 86%, 87%, 88%, 89%, 90%, 91%, 92%, 93%, 94%, 95%, 96%, 97%, 98%, 99% or 100% identity to SEQ ID NOs: 35, 36 (X1=L, X2=I; X1=F, X2=V; or X1=F, X2=I), or 37.

4. The isolated monoclonal antibody or the antigen-binding portion thereof of claim 1, wherein the heavy chain variable region and the light chain variable region comprise amino acid sequences of (1) SEQ ID NOs: 32 and 35, respectively; (2) SEQ ID NOs: 33 (X1=W, X2=S) and 36 (X1=L, X2=I; X1=F, X2=V; or X1=F, X2=I), respectively; (3) SEQ ID NOs: 33 (X1=W, X2=S) and 37, respectively; (4) SEQ ID NOs: 34 and 36 (X1=L, X2=I; X1=F, X2=V; or X1=F, X2=I), respectively; (5) SEQ ID NOs: 34 and 37, respectively; (6) SEQ ID NOs: 33 (X1=L, X2=A) and 36 (X1=L, X2=I; X1=F, X2=V; or X1=F, X2=I), respectively; (7) SEQ ID NOs: 33 (X1=L, X2=A) and 37, respectively; (8) SEQ ID NOs: 33 (X1=W, X2=A) and 36 (X1=L, X2=I; X1=F, X2=V; or X1=F, X2=I), respectively; or (9) SEQ ID NOs: 33 (X1=W, X2=A) and 37, respectively.

5. The isolated monoclonal antibody or the antigen-binding portion thereof of claim 4, comprising a heavy chain constant region having an amino acid sequence of SEQ ID NO: 55, linked to the heavy chain variable region, and a light chain constant region having an amino acid sequence of SEQ ID NO: 56, linked to the light chain variable region.

6. The isolated monoclonal antibody or the antigen-binding portion thereof of claim 1, which (a) binds human IL4Rα; (b) binds monkey IL4Rα; (c) blocks IL4Rα-IL4 interaction; and (d) blocks IL4Rα-IL13-IL13Rα1 interaction.

7. The isolated monoclonal antibody or the antigen-binding portion thereof of claim 1, which is a mouse, chimeric or humanized antibody.

8. The isolated monoclonal antibody or the antigen-binding portion thereof of claim 1, which is an IgG1, IgG2 or IgG4 isotype.

9. A nucleotide encoding the isolated monoclonal antibody or the antigen-binding portion thereof of claim 1.

10. An expression vector comprising the nucleotide of claim 9.

11. A host cell comprising the nucleotide of claim 9.

12. A pharmaceutical composition comprising the isolated monoclonal antibody or the antigen-binding portion thereof of claim 1, and a pharmaceutically acceptable carrier.

13. The pharmaceutical composition of claim 12, further comprising an anti-allergic agent or an anti-tumor agent.

14. The pharmaceutical composition of claim 13, wherein the anti-allergic agent is an antihistamine agent, corticosteroid, an agonist of beta-adrenergic receptors, an agent targeting cyc-LTs, or an agent targeting IgE.

15. A method for treating an allergic disease, comprising administering to the subject a therapeutically effective amount of the pharmaceutical composition of claim 12.

16. The method of claim 15, wherein the allergic disease is atopic dermatitis, anaphylaxis, allergic rhinitis, or allergic asthma.

17. A method for treating a tumor associated with increased STAT6 activation in a subject, comprising administering to the subject a therapeutically effective amount of the pharmaceutical composition of claim 12.

18. The method of claim 17, wherein the tumor is a solid tumor.

19. The isolated monoclonal antibody or the antigen-binding portion thereof of claim 1, wherein the heavy chain variable region and the light chain variable region comprise amino acid sequences of SEQ ID NOs: 33 (X1=W, X2=A) and 36 (X1=F, X2=V), respectively.

20. The isolated monoclonal antibody or the antigen-binding portion thereof of claim 19, comprising a heavy chain constant region having an amino acid sequence of SEQ ID NO: 55, linked to the heavy chain variable region, and a light chain constant region having an amino acid sequence of SEQ ID NO: 56, linked to the light chain variable region.

21. The isolated monoclonal antibody or the antigen-binding portion thereof of claim 1, wherein the antigen-binding fragment comprises an scFv, an Fab fragment, or an $F(ab')_2$ fragment.

22. A pharmaceutical composition comprising the isolated monoclonal antibody or the antigen-binding portion thereof of claim 20, and a pharmaceutically acceptable carrier.

* * * * *

SEQUENCE LISTING

```
<160> NUMBER OF SEQ ID NOS: 72

<210> SEQ ID NO 1
<211> LENGTH: 5
<212> TYPE: PRT
<213> ORGANISM: Mus sp.

<400> SEQUENCE: 1

Thr Tyr Gly Met Ser
1               5


<210> SEQ ID NO 2
<211> LENGTH: 5
<212> TYPE: PRT
<213> ORGANISM: Mus sp.

<400> SEQUENCE: 2

Asp Thr Tyr Met His
1               5


<210> SEQ ID NO 3
<211> LENGTH: 5
<212> TYPE: PRT
<213> ORGANISM: Mus sp.

<400> SEQUENCE: 3
```

Ser Tyr Ala Met Ser
1 5

<210> SEQ ID NO 4
<211> LENGTH: 5
<212> TYPE: PRT
<213> ORGANISM: Mus sp.

<400> SEQUENCE: 4

Asn Tyr Ala Met Ser
1 5

<210> SEQ ID NO 5
<211> LENGTH: 17
<212> TYPE: PRT
<213> ORGANISM: Mus sp.

<400> SEQUENCE: 5

Thr Ile Asn Ser Asn Gly Gly Ser Thr Ser Tyr Pro Asp Ser Val Lys
1 5 10 15

Gly

<210> SEQ ID NO 6
<211> LENGTH: 17
<212> TYPE: PRT
<213> ORGANISM: Mus sp.

<400> SEQUENCE: 6

Thr Ile Asn Ser Asn Gly Gly Ser Thr Asn Tyr Pro Asp Ser Val Lys
1 5 10 15

Gly

<210> SEQ ID NO 7
<211> LENGTH: 17
<212> TYPE: PRT
<213> ORGANISM: Mus sp.

<400> SEQUENCE: 7

Arg Ile Asp Pro Thr Asn Gly Tyr Thr Ile Tyr Ala Ser Lys Phe Gln
1 5 10 15

Gly

<210> SEQ ID NO 8
<211> LENGTH: 17
<212> TYPE: PRT
<213> ORGANISM: Mus sp.

<400> SEQUENCE: 8

Gly Ile Arg Ser Gly Gly Ser Tyr Thr Tyr Tyr Pro Asp Thr Val Lys
1 5 10 15

Gly

<210> SEQ ID NO 9
<211> LENGTH: 16
<212> TYPE: PRT
<213> ORGANISM: Mus sp.

<400> SEQUENCE: 9

Ser Ile Ser Ser Gly Asp Ser Thr Tyr Tyr Leu Asp Ser Val Lys Gly
1 5 10 15

<210> SEQ ID NO 10

<211> LENGTH: 10
<212> TYPE: PRT
<213> ORGANISM: Mus sp.

<400> SEQUENCE: 10

Phe Phe Arg Phe Arg Asn Ala Met Asp Tyr
1               5                   10

<210> SEQ ID NO 11
<211> LENGTH: 10
<212> TYPE: PRT
<213> ORGANISM: Mus sp.

<400> SEQUENCE: 11

Phe Phe Arg Ile Arg Asn Ala Met Asp Tyr
1               5                   10

<210> SEQ ID NO 12
<211> LENGTH: 7
<212> TYPE: PRT
<213> ORGANISM: Mus sp.

<400> SEQUENCE: 12

Arg Arg Pro Trp Phe Ala Tyr
1               5

<210> SEQ ID NO 13
<211> LENGTH: 11
<212> TYPE: PRT
<213> ORGANISM: Mus sp.

<400> SEQUENCE: 13

Gly Asp Lys Leu Arg Pro Tyr His Phe Asp Tyr
1               5                   10

<210> SEQ ID NO 14
<211> LENGTH: 7
<212> TYPE: PRT
<213> ORGANISM: Mus sp.

<400> SEQUENCE: 14

Ser Gly Gly Ser Ala Pro Tyr
1               5

<210> SEQ ID NO 15
<211> LENGTH: 11
<212> TYPE: PRT
<213> ORGANISM: Mus sp.

<400> SEQUENCE: 15

Arg Thr Ser Glu Asn Ile Tyr Ser Tyr Leu Ala
1               5                   10

<210> SEQ ID NO 16
<211> LENGTH: 11
<212> TYPE: PRT
<213> ORGANISM: Mus sp.

<400> SEQUENCE: 16

Arg Ala Ser Glu Asn Ile Tyr Ser Tyr Leu Ala
1               5                   10

<210> SEQ ID NO 17
<211> LENGTH: 16
<212> TYPE: PRT

<213> ORGANISM: Mus sp.

<400> SEQUENCE: 17

Arg Ser Ser Gln Ser Ile Val His Ser Asn Gly Asn Thr Tyr Leu Glu
1 5 10 15

<210> SEQ ID NO 18
<211> LENGTH: 11
<212> TYPE: PRT
<213> ORGANISM: Mus sp.

<400> SEQUENCE: 18

Lys Ala Ser Gln Asp Val Thr Thr Ala Val Ala
1 5 10

<210> SEQ ID NO 19
<211> LENGTH: 11
<212> TYPE: PRT
<213> ORGANISM: Mus sp.

<400> SEQUENCE: 19

Lys Ala Ser Gln Asp Val Ser Thr Ala Val Val
1 5 10

<210> SEQ ID NO 20
<211> LENGTH: 10
<212> TYPE: PRT
<213> ORGANISM: Mus sp.

<400> SEQUENCE: 20

Ser Ala Ser Ser Ser Val Asn Tyr Met Tyr
1 5 10

<210> SEQ ID NO 21
<211> LENGTH: 10
<212> TYPE: PRT
<213> ORGANISM: Mus sp.

<400> SEQUENCE: 21

Ser Ala Ser Ser Ser Val Ser Tyr Met Tyr
1 5 10

<210> SEQ ID NO 22
<211> LENGTH: 7
<212> TYPE: PRT
<213> ORGANISM: Mus sp.

<400> SEQUENCE: 22

Asn Ala Lys Thr Leu Ala Glu
1 5

<210> SEQ ID NO 23
<211> LENGTH: 7
<212> TYPE: PRT
<213> ORGANISM: Mus sp.

<400> SEQUENCE: 23

Lys Val Thr Asn Arg Phe Ser
1 5

<210> SEQ ID NO 24
<211> LENGTH: 7
<212> TYPE: PRT
<213> ORGANISM: Mus sp.

```
<400> SEQUENCE: 24

Ser Ala Ser Tyr Arg Tyr Thr
1               5


<210> SEQ ID NO 25
<211> LENGTH: 7
<212> TYPE: PRT
<213> ORGANISM: Mus sp.

<400> SEQUENCE: 25

Arg Thr Ser Asn Leu Ala Ser
1               5


<210> SEQ ID NO 26
<211> LENGTH: 10
<212> TYPE: PRT
<213> ORGANISM: Mus sp.

<400> SEQUENCE: 26

Gln His Tyr Tyr Gly Pro Pro Thr Trp Thr
1               5                   10


<210> SEQ ID NO 27
<211> LENGTH: 10
<212> TYPE: PRT
<213> ORGANISM: Mus sp.

<400> SEQUENCE: 27

Gln His Tyr Tyr Gly Thr Pro Thr Trp Thr
1               5                   10


<210> SEQ ID NO 28
<211> LENGTH: 9
<212> TYPE: PRT
<213> ORGANISM: Mus sp.

<400> SEQUENCE: 28

Phe Gln Gly Ser His Val Pro Tyr Thr
1               5


<210> SEQ ID NO 29
<211> LENGTH: 9
<212> TYPE: PRT
<213> ORGANISM: Mus sp.

<400> SEQUENCE: 29

Gln Gln His Tyr Ser Asp Pro Tyr Thr
1               5


<210> SEQ ID NO 30
<211> LENGTH: 9
<212> TYPE: PRT
<213> ORGANISM: Mus sp.

<400> SEQUENCE: 30

Gln Gln His Tyr Ser Ala Pro Tyr Thr
1               5


<210> SEQ ID NO 31
<211> LENGTH: 9
<212> TYPE: PRT
<213> ORGANISM: Mus sp.

<400> SEQUENCE: 31
```

```
Gln Gln Tyr His Ser Phe Pro Leu Thr
1               5


<210> SEQ ID NO 32
<211> LENGTH: 119
<212> TYPE: PRT
<213> ORGANISM: Mus sp.

<400> SEQUENCE: 32

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr
            20                  25                  30

Gly Met Ser Trp Val Arg Gln Thr Pro Asp Lys Arg Leu Glu Leu Val
        35                  40                  45

Ala Thr Ile Asn Ser Asn Gly Gly Ser Thr Ser Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Phe Tyr Cys
                85                  90                  95

Ala Arg Phe Phe Arg Phe Arg Asn Ala Met Asp Tyr Trp Gly Gln Gly
            100                 105                 110

Thr Ser Val Thr Val Ser Ser
        115


<210> SEQ ID NO 33
<211> LENGTH: 119
<212> TYPE: PRT
<213> ORGANISM: Artificial Sequence
<220> FEATURE:
<223> OTHER INFORMATION: VH for huC2C1A1A1-V1 - huC2C1A1A1-V4 and
      huC2C1A1A1-V9 - huC2C1A1A1-V16
<220> FEATURE:
<221> NAME/KEY: UNSURE
<222> LOCATION: (47)..(47)
<223> OTHER INFORMATION: X= W or L
<220> FEATURE:
<221> NAME/KEY: UNSURE
<222> LOCATION: (49)..(49)
<223> OTHER INFORMATION: X= S or A

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Met Ser Trp Val Arg Gln Ala Pro Gly Lys Gly Leu Val Xaa Val
        35                  40                  45

Xaa Thr Ile Asn Ser Asn Gly Gly Ser Thr Ser Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Phe Arg Phe Arg Asn Ala Met Asp Tyr Trp Gly Gln Gly
            100                 105                 110

Thr Leu Val Thr Val Ser Ser
        115
```

```
<210> SEQ ID NO 34
<211> LENGTH: 119
<212> TYPE: PRT
<213> ORGANISM: Artificial Sequence
<220> FEATURE:
<223> OTHER INFORMATION: VH for huC2C1A1A1-V5-huC2C1A1A1-V8

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Met Ser Trp Val Arg Gln Ser Pro Asp Lys Arg Leu Glu Trp Val
        35                  40                  45

Ser Thr Ile Asn Ser Asn Gly Gly Ser Thr Ser Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Arg Ser Leu Arg Ala Glu Asp Thr Ala Val Tyr Tyr Cys
                85                  90                  95

Ala Arg Phe Phe Arg Phe Arg Asn Ala Met Asp Tyr Trp Gly Gln Gly
            100                 105                 110

Thr Leu Val Thr Val Ser Ser
        115


<210> SEQ ID NO 35
<211> LENGTH: 108
<212> TYPE: PRT
<213> ORGANISM: Mus sp.

<400> SEQUENCE: 35

Asp Ile Gln Met Thr Gln Ser Pro Ala Ser Leu Ser Ala Ser Val Gly
1               5                   10                  15

Glu Thr Val Thr Ile Thr Cys Arg Thr Ser Glu Asn Ile Tyr Ser Tyr
            20                  25                  30

Leu Ala Trp Tyr Gln Gln Lys Gln Gly Lys Ser Pro Gln Phe Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Asn Ile Asn Ser Leu Gln Ser
65                  70                  75                  80

Glu Asp Phe Gly Ser Tyr Tyr Cys Gln His Tyr Tyr Gly Pro Pro Thr
                85                  90                  95

Trp Thr Phe Gly Gly Gly Thr Lys Leu Glu Ile Lys
            100                 105


<210> SEQ ID NO 36
<211> LENGTH: 108
<212> TYPE: PRT
<213> ORGANISM: Artificial Sequence
<220> FEATURE:
<223> OTHER INFORMATION: VL for huC2C1A1A1-V1, huC2C1A1A1-V3-huC2C1A1A1-
      V5, huC2C1A1A1-V7 - huC2C1A1A1-V9, huC2C1A1A1-V11 - huC2C1A1A1-
      V13, huC2C1A1A1-V15 and huC2C1A1A1-V16
<220> FEATURE:
<221> NAME/KEY: UNSURE
<222> LOCATION: (46)..(46)
<223> OTHER INFORMATION: X= L or F
<220> FEATURE:
<221> NAME/KEY: UNSURE
<222> LOCATION: (48)..(48)
<223> OTHER INFORMATION: X= I or V
```

<400> SEQUENCE: 36

```
Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Ile Tyr Ser Tyr
            20                  25                  30

Leu Ala Trp Tyr Gln Gln Lys Pro Gly Lys Ala Pro Lys Xaa Leu Xaa
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Tyr Tyr Gly Pro Pro Thr
                85                  90                  95

Trp Thr Phe Gly Gln Gly Thr Lys Val Glu Ile Lys
            100                 105
```

<210> SEQ ID NO 37
<211> LENGTH: 108
<212> TYPE: PRT
<213> ORGANISM: Artificial Sequence
<220> FEATURE:
<223> OTHER INFORMATION: VL for huC2C1A1A1-V2,huC2C1A1A1-V6,huC2C1A1A1-V10 and huC2C1A1A1-V14

<400> SEQUENCE: 37

```
Asp Ile Gln Met Thr Gln Ser Pro Ser Ser Leu Ser Ala Ser Val Gly
1               5                   10                  15

Gln Arg Val Thr Ile Thr Cys Arg Thr Ser Glu Asn Ile Tyr Ser Tyr
            20                  25                  30

Leu Ala Trp Tyr Gln Gln Lys Gln Gly Lys Pro Pro Arg Phe Leu Ile
        35                  40                  45

Tyr Asn Ala Lys Thr Leu Ala Glu Gly Val Pro Ser Arg Phe Ser Gly
    50                  55                  60

Ser Gly Ser Gly Thr Glu Phe Thr Leu Thr Ile Thr Ser Leu Gln Ala
65                  70                  75                  80

Glu Asp Phe Gly Val Tyr Tyr Cys Gln His Tyr Tyr Gly Pro Pro Thr
                85                  90                  95

Trp Thr Phe Gly Pro Gly Thr Lys Leu Glu Ile Lys
            100                 105
```

<210> SEQ ID NO 38
<211> LENGTH: 119
<212> TYPE: PRT
<213> ORGANISM: Mus sp.

<400> SEQUENCE: 38

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr
            20                  25                  30

Gly Met Ser Trp Val Arg Gln Thr Pro Asp Lys Arg Leu Glu Leu Val
        35                  40                  45

Ala Thr Ile Asn Ser Asn Gly Gly Ser Thr Asn Tyr Pro Asp Ser Val
    50                  55                  60

Lys Gly Arg Phe Thr Ile Ser Arg Asp Asn Ala Lys Asn Thr Leu Tyr
65                  70                  75                  80
```

```
Leu Gln Met Ser Ser Leu Lys Ser Glu Asp Thr Ala Met Tyr Tyr Cys
            85                  90                  95

Ala Arg Phe Phe Arg Ile Arg Asn Ala Met Asp Tyr Trp Gly Gln Gly
            100                 105                 110

Thr Ser Val Thr Val Ser Ser
        115


<210> SEQ ID NO 39
<211> LENGTH: 108
<212> TYPE: PRT
<213> ORGANISM: Mus sp.

<400> SEQUENCE: 39

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Phe Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His Tyr Tyr Gly Thr Pro Thr
                85                  90                  95

Trp Thr Phe Gly Gly Gly Thr Lys Leu Glu Ile Lys
            100                 105


<210> SEQ ID NO 40
<211> LENGTH: 116
<212> TYPE: PRT
<213> ORGANISM: Mus sp.

<400> SEQUENCE: 40

Glu Val Gln Leu Gln Gln Ser Gly Ala Asp Leu Val Arg Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Val
        35                  40                  45

Gly Arg Ile Asp Pro Thr Asn Gly Tyr Thr Ile Tyr Ala Ser Lys Phe
    50                  55                  60

Gln Gly Lys Ala Thr Ile Thr Ala Asp Thr Ser Ser Asn Thr Ala Tyr
65                  70                  75                  80

Met Gln Leu Ser Ser Leu Thr Ser Gly Asp Thr Ala Val Tyr His Cys
                85                  90                  95

Val Ser Arg Arg Pro Trp Phe Ala Tyr Trp Gly Gln Gly Thr Leu Val
            100                 105                 110

Thr Val Ser Ala
        115


<210> SEQ ID NO 41
<211> LENGTH: 116
<212> TYPE: PRT
<213> ORGANISM: Artificial Sequence
<220> FEATURE:
<223> OTHER INFORMATION: VH for huB8G11F2B7G5E8-V1 - huB8G11F2B7G5E8-V4,
      huB8G11F2B7G5E8-V9 and huB8G11F2B7G5E8-V14
<220> FEATURE:
```

```
<221> NAME/KEY: UNSURE
<222> LOCATION: (24)..(24)
<223> OTHER INFORMATION: X= A or V
<220> FEATURE:
<221> NAME/KEY: UNSURE
<222> LOCATION: (38)..(38)
<223> OTHER INFORMATION: X= K or Q
<220> FEATURE:
<221> NAME/KEY: UNSURE
<222> LOCATION: (48)..(48)
<223> OTHER INFORMATION: X= V or M
<220> FEATURE:
<221> NAME/KEY: UNSURE
<222> LOCATION: (95)..(95)
<223> OTHER INFORMATION: X= H or Y

<400> SEQUENCE: 41

Glu Val Gln Leu Val Gln Ser Gly Ala Glu Val Lys Lys Pro Gly Ala
1               5                   10                  15

Thr Val Lys Ile Ser Cys Lys Xaa Ser Gly Phe Asn Ile Lys Asp Thr
            20                  25                  30

Tyr Met His Trp Val Xaa Gln Ala Pro Gly Lys Gly Leu Glu Trp Xaa
        35                  40                  45

Gly Arg Ile Asp Pro Thr Asn Gly Tyr Thr Ile Tyr Ala Ser Lys Phe
    50                  55                  60

Gln Gly Lys Ala Thr Ile Thr Ala Asp Thr Ser Ser Asn Thr Ala Tyr
65                  70                  75                  80

Met Glu Leu Ser Ser Leu Arg Ser Glu Asp Thr Ala Val Tyr Xaa Cys
                85                  90                  95

Val Ser Arg Arg Pro Trp Phe Ala Tyr Trp Gly Gln Gly Thr Leu Val
            100                 105                 110

Thr Val Ser Ser
        115


<210> SEQ ID NO 42
<211> LENGTH: 116
<212> TYPE: PRT
<213> ORGANISM: Artificial Sequence
<220> FEATURE:
<223> OTHER INFORMATION: VH for huB8G11F2B7G5E8-V5 - huB8G11F2B7G5E8-V8
      and huB8G11F2B7G5E8-V10
<220> FEATURE:
<221> NAME/KEY: UNSURE
<222> LOCATION: (67)..(67)
<223> OTHER INFORMATION: X= R or K
<220> FEATURE:
<221> NAME/KEY: UNSURE
<222> LOCATION: (68)..(68)
<223> OTHER INFORMATION: X= A or V
<220> FEATURE:
<221> NAME/KEY: UNSURE
<222> LOCATION: (76)..(76)
<223> OTHER INFORMATION: X= S or T
<220> FEATURE:
<221> NAME/KEY: UNSURE
<222> LOCATION: (77)..(77)
<223> OTHER INFORMATION: X= N or D

<400> SEQUENCE: 42

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Asn Ile Lys Asp Thr
            20                  25                  30

Tyr Met His Trp Val Lys Gln Ala Pro Gly Lys Gly Leu Glu Trp Val
        35                  40                  45

Gly Arg Ile Asp Pro Thr Asn Gly Tyr Thr Ile Tyr Ala Ser Lys Phe
```

```
    50                  55                  60

Gln Gly Xaa Xaa Thr Ile Thr Ala Asp Thr Ser Xaa Xaa Thr Ala Tyr
65                  70                  75                  80

Met Glu Leu Ser Ser Leu Arg Ser Glu Asp Thr Ala Val Tyr His Cys
                85                  90                  95

Val Ser Arg Arg Pro Trp Phe Ala Tyr Trp Gly Gln Gly Thr Leu Val
            100                 105                 110

Thr Val Ser Ser
        115


<210> SEQ ID NO 43
<211> LENGTH: 116
<212> TYPE: PRT
<213> ORGANISM: Artificial Sequence
<220> FEATURE:
<223> OTHER INFORMATION: VH for huB8G11F2B7G5E8-V11

<400> SEQUENCE: 43

Glu Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Lys Asp Thr
            20                  25                  30

Tyr Met His Trp Val Gln Gln Ala Pro Gly Lys Gly Leu Glu Trp Met
        35                  40                  45

Gly Leu Ile Asp Pro Thr Asn Gly Tyr Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Val Ser Arg Arg Pro Trp Phe Ala Tyr Trp Gly Gln Gly Thr Leu Val
            100                 105                 110

Thr Val Ser Ser
        115


<210> SEQ ID NO 44
<211> LENGTH: 116
<212> TYPE: PRT
<213> ORGANISM: Artificial Sequence
<220> FEATURE:
<223> OTHER INFORMATION: VH for huB8G11F2B7G5E8-V13

<400> SEQUENCE: 44

Gln Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Val
        35                  40                  45

Gly Arg Ile Asp Pro Thr Asn Gly Tyr Thr Ile Tyr Ala Ser Lys Phe
    50                  55                  60

Gln Gly Lys Ala Thr Ile Thr Ala Asp Thr Ser Ser Asn Thr Ala Tyr
65                  70                  75                  80

Met Gln Leu Ser Ser Leu Thr Ser Glu Asp Thr Ala Val Tyr His Cys
                85                  90                  95

Val Ser Arg Arg Pro Trp Phe Ala Tyr Trp Gly Gln Gly Thr Thr Leu
            100                 105                 110
```

```
Thr Val Ser Ser
        115


<210> SEQ ID NO 45
<211> LENGTH: 112
<212> TYPE: PRT
<213> ORGANISM: Mus sp.

<400> SEQUENCE: 45

Asp Ile Leu Met Thr Gln Thr Pro Leu Ser Leu Pro Val Ser Leu Gly
1               5                   10                  15

Ala Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Thr Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Tyr Cys Phe Gln Gly
                85                  90                  95

Ser His Val Pro Tyr Thr Phe Gly Gly Gly Thr Lys Leu Glu Ile Lys
            100                 105                 110


<210> SEQ ID NO 46
<211> LENGTH: 112
<212> TYPE: PRT
<213> ORGANISM: Artificial Sequence
<220> FEATURE:
<223> OTHER INFORMATION: VL for huB8G11F2B7G5E8-V1 - huB8G11F2B7G5E8-
      V11, huB8G11F2B7G5E8-V13 and huB8G11F2B7G5E8-V14

<400> SEQUENCE: 46

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Thr Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gln Gly Thr Lys Leu Glu Ile Lys
            100                 105                 110


<210> SEQ ID NO 47
<211> LENGTH: 120
<212> TYPE: PRT
<213> ORGANISM: Mus sp.

<400> SEQUENCE: 47

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
```

```
        35                  40                  45

Ala Gly Ile Arg Ser Gly Gly Ser Tyr Thr Tyr Tyr Pro Asp Thr Val
    50                  55                  60

Lys Gly Arg Phe Thr Ile Ser Arg Asp Asn Ala Arg Asn Thr Leu Tyr
65                  70                  75                  80

Leu Gln Met Asn Ser Leu Arg Ser Glu Asp Thr Ala Ile Tyr Tyr Cys
                85                  90                  95

Ala Arg Gly Asp Lys Leu Arg Pro Tyr His Phe Asp Tyr Trp Gly Gln
            100                 105                 110

Gly Thr Thr Leu Thr Val Ser Ser
        115                 120


<210> SEQ ID NO 48
<211> LENGTH: 107
<212> TYPE: PRT
<213> ORGANISM: Mus sp.

<400> SEQUENCE: 48

Asp Ile Val Met Thr Gln Ser His Lys Phe Met Ser Thr Ser Val Gly
1               5                   10                  15

Asp Lys Val Ser Ile Thr Cys Lys Ala Ser Gln Asp Val Thr Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Ala Gly
    50                  55                  60

Ser Gly Ser Gly Thr Asp Phe Thr Val Thr Ile Ser Thr Val Gln Ala
65                  70                  75                  80

Glu Asp Leu Ala Val Tyr Tyr Cys Gln Gln His Tyr Ser Asp Pro Tyr
                85                  90                  95

Thr Phe Gly Gly Gly Thr Lys Leu Glu Ile Lys
            100                 105


<210> SEQ ID NO 49
<211> LENGTH: 120
<212> TYPE: PRT
<213> ORGANISM: Mus sp.

<400> SEQUENCE: 49

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Gly Ile Arg Ser Gly Gly Ser Tyr Thr Tyr Tyr Pro Asp Thr Val
    50                  55                  60

Lys Gly Arg Phe Thr Ile Ser Arg Asp Asn Ala Arg Asn Thr Leu Tyr
65                  70                  75                  80

Leu Gln Met Ser Ser Leu Arg Ser Glu Asp Thr Ala Ile Tyr Tyr Cys
                85                  90                  95

Ala Arg Gly Asp Lys Leu Arg Pro Tyr His Phe Asp Tyr Trp Gly Gln
            100                 105                 110

Gly Thr Thr Leu Thr Val Ser Ser
        115                 120
```

<210> SEQ ID NO 50
<211> LENGTH: 107
<212> TYPE: PRT
<213> ORGANISM: Mus sp.

<400> SEQUENCE: 50

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Val Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ile Thr Val Gln Ala
65                  70                  75                  80

Glu Asp Leu Ala Val Tyr Tyr Cys Gln Gln His Tyr Ser Ala Pro Tyr
                85                  90                  95

Thr Phe Gly Gly Gly Thr Gln Leu Glu Ile Lys
            100                 105
```

<210> SEQ ID NO 51
<211> LENGTH: 115
<212> TYPE: PRT
<213> ORGANISM: Mus sp.

<400> SEQUENCE: 51

```
Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Ser Ile Ser Ser Gly Asp Ser Thr Tyr Tyr Leu Asp Ser Val Lys
    50                  55                  60

Gly Arg Phe Thr Ile Ser Arg Asp Asn Ala Arg Asn Ile Leu Tyr Leu
65                  70                  75                  80

Gln Val Ser Ser Leu Arg Ser Glu Asp Thr Ala Met Tyr Tyr Cys Glu
                85                  90                  95

Arg Ser Gly Gly Ser Ala Pro Tyr Trp Gly Gln Gly Thr Leu Val Thr
            100                 105                 110

Val Ser Ala
        115
```

<210> SEQ ID NO 52
<211> LENGTH: 106
<212> TYPE: PRT
<213> ORGANISM: Mus sp.

<400> SEQUENCE: 52

```
Gln Ile Val Leu Thr Gln Ser Pro Ala Ile Met Ser Ala Ser Pro Gly
1               5                   10                  15

Asp Met Val Thr Ile Ser Cys Ser Ala Ser Ser Ser Val Asn Tyr Met
            20                  25                  30

Tyr Trp Tyr Gln Gln Lys Pro Gly Ser Ser Pro Lys Pro Trp Ile Tyr
        35                  40                  45

Arg Thr Ser Asn Leu Ala Ser Gly Val Pro Ala Arg Phe Ser Gly Ser
    50                  55                  60
```

```
Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Tyr His Ser Phe Pro Leu Thr
                85                  90                  95

Phe Gly Ala Gly Thr Lys Leu Glu Leu Lys
            100                 105


<210> SEQ ID NO 53
<211> LENGTH: 115
<212> TYPE: PRT
<213> ORGANISM: Mus sp.

<400> SEQUENCE: 53

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Ser Ile Ser Ser Gly Asp Ser Thr Tyr Tyr Leu Asp Ser Val Lys
    50                  55                  60

Gly Arg Phe Thr Ile Ser Arg Asp Asn Ala Met Asn Ile Leu Tyr Leu
65                  70                  75                  80

Gln Met Ser Ser Leu Arg Ser Glu Asp Thr Ala Val Tyr Tyr Cys Glu
                85                  90                  95

Arg Ser Gly Gly Ser Ala Pro Tyr Trp Gly Gln Gly Thr Leu Val Ser
            100                 105                 110

Val Ser Ala
        115


<210> SEQ ID NO 54
<211> LENGTH: 106
<212> TYPE: PRT
<213> ORGANISM: Mus sp.

<400> SEQUENCE: 54

Gln Ile Val Leu Thr Gln Ser Pro Ala Ile Met Ser Ala Ser Pro Gly
1               5                   10                  15

Glu Met Val Thr Ile Ser Cys Ser Ala Ser Ser Ser Val Ser Tyr Met
            20                  25                  30

Tyr Trp Tyr Gln Gln Lys Pro Gly Ser Ser Pro Lys Pro Trp Ile Tyr
        35                  40                  45

Arg Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Tyr His Ser Phe Pro Leu Thr
                85                  90                  95

Phe Gly Ala Gly Thr Lys Leu Glu Leu Lys
            100                 105


<210> SEQ ID NO 55
<211> LENGTH: 327
<212> TYPE: PRT
<213> ORGANISM: Artificial Sequence
<220> FEATURE:
<223> OTHER INFORMATION: Heavy chain constant region for chimeric and
      humanized antibodies
```

<400> SEQUENCE: 55

Ala Ser Thr Lys Gly Pro Ser Val Phe Pro Leu Ala Pro Cys Ser Arg
1 5 10 15

Ser Thr Ser Glu Ser Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Lys Thr
65 70 75 80

Tyr Thr Cys Asn Val Asp His Lys Pro Ser Asn Thr Lys Val Asp Lys
85 90 95

Arg Val Glu Ser Lys Tyr Gly Pro Pro Cys Pro Pro Cys Pro Ala Pro
100 105 110

Glu Phe Leu Gly Gly Pro Ser Val Phe Leu Phe Pro Pro Lys Pro Lys
115 120 125

Asp Thr Leu Met Ile Ser Arg Thr Pro Glu Val Thr Cys Val Val Val
130 135 140

Asp Val Ser Gln Glu Asp Pro Glu Val Gln Phe Asn Trp Tyr Val Asp
145 150 155 160

Gly Val Glu Val His Asn Ala Lys Thr Lys Pro Arg Glu Glu Gln Phe
165 170 175

Asn Ser Thr Tyr Arg Val Val Ser Val Leu Thr Val Leu His Gln Asp
180 185 190

Trp Leu Asn Gly Lys Glu Tyr Lys Cys Lys Val Ser Asn Lys Gly Leu
195 200 205

Pro Ser Ser Ile Glu Lys Thr Ile Ser Lys Ala Lys Gly Gln Pro Arg
210 215 220

Glu Pro Gln Val Tyr Thr Leu Pro Pro Ser Gln Glu Glu Met Thr Lys
225 230 235 240

Asn Gln Val Ser Leu Thr Cys Leu Val Lys Gly Phe Tyr Pro Ser Asp
245 250 255

Ile Ala Val Glu Trp Glu Ser Asn Gly Gln Pro Glu Asn Asn Tyr Lys
260 265 270

Thr Thr Pro Pro Val Leu Asp Ser Asp Gly Ser Phe Phe Leu Tyr Ser
275 280 285

Arg Leu Thr Val Asp Lys Ser Arg Trp Gln Glu Gly Asn Val Phe Ser
290 295 300

Cys Ser Val Met His Glu Ala Leu His Asn His Tyr Thr Gln Lys Ser
305 310 315 320

Leu Ser Leu Ser Leu Gly Lys
325

<210> SEQ ID NO 56
<211> LENGTH: 107
<212> TYPE: PRT
<213> ORGANISM: Artificial Sequence
<220> FEATURE:
<223> OTHER INFORMATION: Light chain constant region for chimeric and humanized antibodies

<400> SEQUENCE: 56

Arg Thr Val Ala Ala Pro Ser Val Phe Ile Phe Pro Pro Ser Asp Glu
1 5 10 15

```
Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 57
<211> LENGTH: 242
<212> TYPE: PRT
<213> ORGANISM: Artificial Sequence
<220> FEATURE:
<223> OTHER INFORMATION: Human IL4Ralpha-his

<400> SEQUENCE: 57

Met Gly Trp Leu Cys Ser Gly Leu Leu Phe Pro Val Ser Cys Leu Val
1               5                   10                  15

Leu Leu Gln Val Ala Ser Ser Gly Asn Met Lys Val Leu Gln Glu Pro
            20                  25                  30

Thr Cys Val Ser Asp Tyr Met Ser Ile Ser Thr Cys Glu Trp Lys Met
        35                  40                  45

Asn Gly Pro Thr Asn Cys Ser Thr Glu Leu Arg Leu Leu Tyr Gln Leu
    50                  55                  60

Val Phe Leu Leu Ser Glu Ala His Thr Cys Ile Pro Glu Asn Asn Gly
65                  70                  75                  80

Gly Ala Gly Cys Val Cys His Leu Leu Met Asp Asp Val Val Ser Ala
                85                  90                  95

Asp Asn Tyr Thr Leu Asp Leu Trp Ala Gly Gln Gln Leu Leu Trp Lys
            100                 105                 110

Gly Ser Phe Lys Pro Ser Glu His Val Lys Pro Arg Ala Pro Gly Asn
        115                 120                 125

Leu Thr Val His Thr Asn Val Ser Asp Thr Leu Leu Leu Thr Trp Ser
    130                 135                 140

Asn Pro Tyr Pro Pro Asp Asn Tyr Leu Tyr Asn His Leu Thr Tyr Ala
145                 150                 155                 160

Val Asn Ile Trp Ser Glu Asn Asp Pro Ala Asp Phe Arg Ile Tyr Asn
                165                 170                 175

Val Thr Tyr Leu Glu Pro Ser Leu Arg Ile Ala Ala Ser Thr Leu Lys
            180                 185                 190

Ser Gly Ile Ser Tyr Arg Ala Arg Val Arg Ala Trp Ala Gln Cys Tyr
        195                 200                 205

Asn Thr Thr Trp Ser Glu Trp Ser Pro Ser Thr Lys Trp His Asn Ser
    210                 215                 220

Tyr Arg Glu Pro Phe Glu Gln His His His His His His His His His
225                 230                 235                 240

His His


<210> SEQ ID NO 58
<211> LENGTH: 242
```

<212> TYPE: PRT
<213> ORGANISM: Artificial Sequence
<220> FEATURE:
<223> OTHER INFORMATION: Cal-IL4Ralpha-his

<400> SEQUENCE: 58

```
Met Gly Trp Leu Cys Ser Gly Leu Leu Phe Pro Val Ser Tyr Leu Val
1               5                   10                  15

Leu Leu Gln Val Ala Gly Ser Gly Ser Met Lys Val Leu Gln Glu Pro
            20                  25                  30

Thr Cys Val Ser Asp Tyr Ile Ser Leu Ser Thr Cys Glu Trp Lys Met
        35                  40                  45

Gly Gly Pro Thr Asn Cys Ser Ala Glu Leu Arg Leu Val Tyr Gln Leu
    50                  55                  60

Val Phe Leu Ile Ser Glu Thr Asn Met Cys Val Pro Glu Asn Asn Gly
65                  70                  75                  80

Ala Ala Gly Cys Val Cys His Leu Phe Met Glu Asp Met Val Gly Ala
                85                  90                  95

Asp Asn Tyr Thr Leu Asp Leu Trp Ala Gly Gln Gln Leu Leu Trp Lys
            100                 105                 110

Gly Ser Phe Lys Pro Ser Glu His Val Lys Pro Lys Ala Pro Glu Asn
        115                 120                 125

Leu Thr Val Tyr Thr Asn Val Ser Glu Thr Leu Leu Leu Thr Trp Ser
    130                 135                 140

Asn Pro Tyr Pro Pro Asp Asn Tyr Leu Tyr Glu Lys Leu Thr Tyr Ala
145                 150                 155                 160

Val Asn Ile Trp Asn Glu Asn Asp Pro Thr Asp Ser Arg Ile Tyr Asp
                165                 170                 175

Val Thr Tyr Gln Glu Pro Thr Leu Arg Ile Ala Ala Ser Thr Leu Lys
            180                 185                 190

Ser Gly Val Ser Tyr Arg Ala Arg Val Arg Ala Trp Ala Gln Ser Tyr
        195                 200                 205

Asn Ser Thr Trp Ser Glu Trp Ser Pro Ser Thr Lys Trp Tyr Asn Ala
    210                 215                 220

Tyr Lys Glu Pro Phe Glu Lys His His His His His His His His His
225                 230                 235                 240

His His
```

<210> SEQ ID NO 59
<211> LENGTH: 357
<212> TYPE: DNA
<213> ORGANISM: Artificial Sequence
<220> FEATURE:
<223> OTHER INFORMATION: VH for mouse C2C1A1A1

<400> SEQUENCE: 59

```
gaggtgcagc tggtggagtc tgggggaggc ttagtgcagc ctggagggtc cctgaaactc     60

tcctgtgcag cctctggatt cactttcagt acttatggca tgtcttgggt tcgccagact    120

ccagacaaga ggctggagtt ggtcgcaacc attaatagta atggtggtag taccagttat    180

ccagacagtg tgaagggccg attcaccatc tccagagaca atgccaagaa caccctgtac    240

ctgcaaatga gcagtctgaa gtctgaggac acagccatgt tttactgtgc aagatttttc    300

cgctttagga atgctatgga ctactggggt caaggaacct cagtcaccgt ctcctca       357
```

<210> SEQ ID NO 60
<211> LENGTH: 357

<212> TYPE: DNA
<213> ORGANISM: Artificial Sequence
<220> FEATURE:
<223> OTHER INFORMATION: VH for chimeric C2C1A1A1

<400> SEQUENCE: 60
gaggtgcagc tggtggagag cggcggcgga ctggtgcagc ctggaggatc cctgaagctg 60
tcctgcgccg cctccggctt caccttctcc acatacggca tgtcctgggt gagacagacc 120
cctgataaga gactggagct ggtggccacc atcaacagca acggcggcag caccagctac 180
cccgacagcg tgaagggcag attcaccatc tccagagaca acgccaagaa caccctgtac 240
ctgcagatgt ccagcctgaa gagcgaggat acagccatgt tctactgtgc caggttcttt 300
aggttcagaa atgccatgga ctactggggc cagggcacct ccgtgacagt gagcagc 357

<210> SEQ ID NO 61
<211> LENGTH: 357
<212> TYPE: DNA
<213> ORGANISM: Artificial Sequence
<220> FEATURE:
<223> OTHER INFORMATION: VH for huC2C1A1A1-V13-huC2C1A1A1-V16

<400> SEQUENCE: 61
gaggtgcagc tggtggagtc cggaggagga ctggtgcagc ccggcggctc tctgagactg 60
agctgcgctg cctccggctt cacctttagc acctacggca tgagctgggt gagacaagcc 120
cccggcaaag gactggtgtg ggtggctacc atcaacagca acggcggctc cacaagctac 180
cccgacagcg tgaagggaag attcaccatc tctagagaca acgccaagaa cacactgtat 240
ctgcagatga actctctgag agccgaagac accgctgtgt actactgcgc tagattcttt 300
agatttagaa acgccatgga ctactggggc caaggcacac tggtgacagt gtcctcc 357

<210> SEQ ID NO 62
<211> LENGTH: 324
<212> TYPE: DNA
<213> ORGANISM: Artificial Sequence
<220> FEATURE:
<223> OTHER INFORMATION: VL for mouse C2C1A1A1

<400> SEQUENCE: 62
gacatccaga tgactcagtc tccagcctcc ctatctgcat ctgtgggaga aactgtcacc 60
atcacatgtc gaacaagtga gaatatttac agttatttag catggtatca gcagaaacag 120
ggaaaatctc ctcagttcct ggtctataat gcaaaaacct tagcagaagg tgtgccatca 180
aggttcagtg gcagtggatc aggcacacag ttttctctga atatcaacag cctgcagtct 240
gaagattttg ggagttatta ctgtcaacat tattatggtc ctcccacgtg gacgttcggt 300
ggaggcacca agctggaaat caaa 324

<210> SEQ ID NO 63
<211> LENGTH: 324
<212> TYPE: DNA
<213> ORGANISM: Artificial Sequence
<220> FEATURE:
<223> OTHER INFORMATION: VL for chimeric C2C1A1A1

<400> SEQUENCE: 63
gacatccaga tgacacagag ccccgccagc ctgtccgcct ccgttggaga gaccgtgacc 60
atcacctgta ggacctccga gaatatctac agctacctgg cctggtatca acagaagcag 120
ggcaagtccc ctcagtttct ggtgtacaac gccaagaccc tggccgaggg cgtgccctct 180

```
aggttctccg gctccggcag cggcacccag ttcagcctga atatcaacag cctgcagagc    240

gaggactttg gcagctacta ctgtcagcac tactacggcc ctcccacctg gacatttggc    300

ggcggcacaa agctggagat caag                                            324


<210> SEQ ID NO 64
<211> LENGTH: 324
<212> TYPE: DNA
<213> ORGANISM: Artificial Sequence
<220> FEATURE:
<223> OTHER INFORMATION: VL for huC2C1A1A1-V3, huC2C1A1A1-V7,
      huC2C1A1A1-V11 and huC2C1A1A1-V15

<400> SEQUENCE: 64

gacatccaga tgacccagag ccctagctct ctgagcgctt ccgtgggaga tagagtgacc     60

atcacatgca gaacctccga gaacatctac agctatctgg cttggtatca gcagaagccc    120

ggcaaggccc ccaagttcct ggtgtacaac gccaagacac tggctgaggg cgtgcctagc    180

agattcagcg gctccggcag cggcacagac tttacactga caatcagctc tctgcaaccc    240

gaggacttcg ccacctacta ctgccagcac tactatggcc cccctacatg gacctttggc    300

caaggcacca aggtggagat caag                                            324


<210> SEQ ID NO 65
<211> LENGTH: 348
<212> TYPE: DNA
<213> ORGANISM: Artificial Sequence
<220> FEATURE:
<223> OTHER INFORMATION: VH for mouse B8G11F2B7G5E8

<400> SEQUENCE: 65

gaggttcagc tgcagcagtc tggggcagat cttgtgaggc caggggcctc agtcaagttg     60

tcctgcacag cttctggctt caacattaaa gacacctata tgcactgggt gaagcagagg    120

cctgaacagg gcctggagtg ggttggaagg attgatccta cgaatggtta tactatatat    180

gcctcaaagt tccagggcaa ggccactata acagcagaca catcatccaa cacagcctac    240

atgcagctca gcagcctgac atctggggac actgccgtct atcattgtgt tagtcggagg    300

ccctggtttg cttactgggg ccaagggact ctggtcactg tctctgca                  348


<210> SEQ ID NO 66
<211> LENGTH: 348
<212> TYPE: DNA
<213> ORGANISM: Artificial Sequence
<220> FEATURE:
<223> OTHER INFORMATION: VH for chimeric B8G11F2B7G5E8

<400> SEQUENCE: 66

gaggtgcagc tgcagcagtc cggcgccgac ctggtgaggc caggagcttc cgtgaagctg     60

agctgcacag ccagcggctt caacatcaag gacacataca tgcactgggt gaagcagagg    120

cccgagcagg gcctggagtg ggtgggaaga atcgacccca ccaacggcta caccatctac    180

gcctccaagt tccagggcaa ggccaccatc acagccgata cctcctccaa cacagcctac    240

atgcagctgt ccagcctgac aagcggcgat accgccgtgt accactgcgt gtccagaagg    300

ccttggttcg cctactgggg ccagggcacc ctggtgacag tgtccgcc                  348


<210> SEQ ID NO 67
<211> LENGTH: 348
<212> TYPE: DNA
<213> ORGANISM: Artificial Sequence
<220> FEATURE:
```

<223> OTHER INFORMATION: VH for huB8G11F2B7G5E8-V14

<400> SEQUENCE: 67

```
gaggtgcagc tggtgcagag cggcgctgag gtgaagaagc ccggcgccac cgtgaagatc     60

agctgcaagg tgagcggctt caacatcaag gacacctaca tgcactgggt gaagcaagcc    120

cccggcaaag gactggagtg gatgggaaga atcgacccca ccaacggcta caccatctac    180

gccagcaagt tccaaggcaa ggccaccatc accgccgaca cctccagcaa taccgcctac    240

atggagctga gctctctgag aagcgaggac accgccgtgt accactgtgt gagcagaaga    300

ccttggttcg cctactgggg ccaaggcaca ctggtgaccg tgagcagc                 348
```

<210> SEQ ID NO 68
<211> LENGTH: 336
<212> TYPE: DNA
<213> ORGANISM: Artificial Sequence
<220> FEATURE:
<223> OTHER INFORMATION: VL for mouse B8G11F2B7G5E8

<400> SEQUENCE: 68

```
gatattttga tgacccaaac tccactctcc ctgcctgtca gtcttggagc tcaagcctcc     60

atctcttgca gatcaagtca gagcattgta catagtaatg gaaacaccta tttagaatgg    120

tacctgcaga aaccaggcca gtctccaaag ctcctgatct acaaagttac caatcgattt    180

tctggggtcc cagataggtt cagtggcagt ggatcaggga cagatttcac actcaagatc    240

agcagagtgg aggctgagga tctgggaatt tattactgct ttcaaggttc acatgttccg    300

tacacgttcg gaggggggac caagctggaa ataaaa                              336
```

<210> SEQ ID NO 69
<211> LENGTH: 336
<212> TYPE: DNA
<213> ORGANISM: Artificial Sequence
<220> FEATURE:
<223> OTHER INFORMATION: VL for chimeric B8G11F2B7G5E8

<400> SEQUENCE: 69

```
gacatcctga tgacacagac accccctgtcc ctgcctgtgt ccctgggcgc tcaggcctcc     60

atctcctgta ggagcagcca gtccatcgtg cacagcaatg gcaacaccta cctggagtgg    120

tacttgcaga agcctggcca gagccccaag ctgctgatct acaaggtgac caacagattc    180

agcggcgtgc ccgataggtt cagcggctcc ggcagcggca ccgatttcac actgaagatc    240

tccagggtgg aggccgagga cctgggcatc tactactgct tccagggctc ccacgtgcct    300

tacacctttg gcggcggcac aaagctggag atcaag                              336
```

<210> SEQ ID NO 70
<211> LENGTH: 336
<212> TYPE: DNA
<213> ORGANISM: Artificial Sequence
<220> FEATURE:
<223> OTHER INFORMATION: VL for huB8G11F2B7G5E8-V1 - huB8G11F2B7G5E8-
      V11, huB8G11F2B7G5E8-V13 and huB8G11F2B7G5E8-V14

<400> SEQUENCE: 70

```
gacatcgtga tgacccagac ccctctgagc ctgtccgtga cacccggcca gcctgccagc     60

atcagctgta ggagctccca gtccatcgtg cactccaatg gcaatacata cctggagtgg    120

tacttgcaga agcccggcca gtcccctcag ctgctgatct acaaggtgac caatagattc    180

tccggcgtgc ccgataggtt ctccggcagc ggctccggca cagacttcac actgaagatc    240
```

```
agcagagtgg aggccgagga cgtgggcgtg tactactgct tccagggctc ccacgtgccc    300

tacaccttcg gccagggcac caagctggag atcaag                              336


<210> SEQ ID NO 71
<211> LENGTH: 984
<212> TYPE: DNA
<213> ORGANISM: Artificial Sequence
<220> FEATURE:
<223> OTHER INFORMATION: Heavy chain constant region for chimeric and
      humanized antibodies

<400> SEQUENCE: 71

gccagcacaa agggcccttc cgtgtttccc ctggcccct gcagcaggag cacctctgag      60

tccaccgccg ccctgggctg tctggtgaag gactactttc ccgagcccgt gaccgtgagc    120

tggaattccg gcgccctgac atccggcgtg cacaccttcc ccgccgtgct gcagtcctcc    180

ggcctgtaca gcctgagctc cgtggtgaca gtgccttcct cctccctggg caccaagacc    240

tacacatgta atgtggatca caagcccagc aacacaaagg tggataagag agtggagtcc    300

aagtacggcc ctccttgccc tccctgtcct gccccagagt tcctgggcgg cccctctgtg    360

ttcctgttcc cccctaagcc caaggacaca ctgatgatct ccaggacccc tgaggtgacc    420

tgcgtggtgg tggacgtgag ccaggaggac cctgaggtgc agttcaattg gtacgtggat    480

ggcgtggagg tgcacaatgc caagacaaag cccagagagg agcagtttaa ttccacatac    540

agggtggtgt ccgtgctgac cgtgctgcac caggattggc tgaacggcaa ggagtacaag    600

tgtaaggtga gcaacaaggg cctgccttcc tccatcgaga agacaatcag caaggccaag    660

ggccagccta gggagcccca ggtgtacaca ctgcctccca gccaggagga gatgaccaag    720

aaccaggtga gcctgacctg cctggtgaag ggcttctacc ctagcgacat cgccgtggag    780

tgggagtcca acggccagcc cgagaataac tacaagacaa cacccccgt gctggattcc    840

gatggcagct tctttctgta ctccaggctg accgtggata agagcaggtg gcaggagggc    900

aatgtgttca gctgctccgt gatgcacgag gccctgcaca atcactacac ccagaagagc    960

ctgtccctga gcctgggcaa gtga                                           984


<210> SEQ ID NO 72
<211> LENGTH: 324
<212> TYPE: DNA
<213> ORGANISM: Artificial Sequence
<220> FEATURE:
<223> OTHER INFORMATION: Light chain constant region for chimeric and
      humanized antibodies

<400> SEQUENCE: 72

cgtacggtgg cggcgccatc tgtcttcatc ttcccgccat ctgatgagca gttgaaatct     60

ggaactgcct ctgttgtgtg cctgctgaat aacttctatc ccagagaggc caaagtacag    120

tggaaggtgg ataacgccct ccaatcgggt aactcccagg agagtgtcac agagcaggac    180

agcaaggaca gcacctacag cctcagcagc accctgacgc tgagcaaagc agactacgag    240

aaacacaaag tctacgcctg cgaagtcacc catcagggcc tgagctcgcc cgtcacaaag    300

agcttcaaca ggggagagtg ttga                                           324
```